(12) United States Patent
Miyoshino et al.

(10) Patent No.: US 10,740,589 B2
(45) Date of Patent: Aug. 11, 2020

(54) SKIN INFORMATION PROCESSING METHOD, SKIN INFORMATION PROCESSING DEVICE, AND NON-TRANSITORY COMPUTER-READABLE MEDIUM

(71) Applicants: KABUSHIKI KAISHA DDS, Nagoya-shi, Aichi (JP); Kenji Miyoshino, Nagoya (JP)

(72) Inventors: Kenji Miyoshino, Nagoya (JP); Tatsuki Yoshimine, Nagoya (JP); Yuhei Niwa, Nagoya (JP); Kenta Okumura, Nagoya (JP)

(73) Assignee: KABUSHIKI KAISHA DDS, Nagoya-shi (JP)

( * ) Notice: Subject to any disclaimer, the term of this patent is extended or adjusted under 35 U.S.C. 154(b) by 0 days.

(21) Appl. No.: 16/383,733

(22) Filed: Apr. 15, 2019

(65) Prior Publication Data
US 2019/0236330 A1    Aug. 1, 2019

Related U.S. Application Data

(63) Continuation of application No. PCT/JP2017/039417, filed on Oct. 31, 2017.

(30) Foreign Application Priority Data

Oct. 31, 2016  (JP) ................................. 2016-213899

(51) Int. Cl.
*G06K 9/00* (2006.01)
*A61B 5/1171* (2016.01)
(Continued)

(52) U.S. Cl.
CPC ........ *G06K 9/00067* (2013.01); *A61B 5/1171* (2016.02); *G06K 9/001* (2013.01);
(Continued)

(58) Field of Classification Search
CPC ............. G06K 9/0006; G06K 9/00013; G06K 9/00067; G06K 9/00073; G06K 9/0008; G06K 9/00093; G06K 9/001
See application file for complete search history.

(56) References Cited

U.S. PATENT DOCUMENTS

| 5,426,708 A | 6/1995 | Hamada et al. |
| 2004/0062425 A1 | 4/2004 | Uchida |

(Continued)

FOREIGN PATENT DOCUMENTS

| JP | H02-153478 A | 6/1990 |
| JP | 2000-132692 A | 5/2000 |

(Continued)

OTHER PUBLICATIONS

U.S. Appl. No. 16/383,758, filed Apr. 15, 2019 in the name of Kenji Miyoshino et al.

(Continued)

*Primary Examiner* — Koosha Sharifi-Tafreshi
(74) *Attorney, Agent, or Firm* — Oliff PLC

(57) ABSTRACT

A skin information processing method for a skin information processing device that includes a storage portion includes include acquiring an image, and determining a base point that represents a sweat pore on a ridge of skin, from the acquired image and acquiring position information corresponding to a position of the base point on the image. The skin information processing method includes acquiring sample information indicating changes in color information around the determined base point, generating, as frequency information, information associating frequency components of the acquired sample information with the position information. The skin information processing method includes causing the storage portion to store information including the generated frequency information and the position infor- (Continued)

mation of the base point, as information used in skin authentication.

12 Claims, 35 Drawing Sheets

(51) Int. Cl.
*G06T 7/00* (2017.01)
*G07C 9/25* (2020.01)
*G07C 9/26* (2020.01)

(52) U.S. Cl.
CPC ............... *G06T 7/00* (2013.01); *G07C 9/257* (2020.01); *G07C 9/26* (2020.01)

(56) References Cited

U.S. PATENT DOCUMENTS

| | | |
|---|---|---|
| 2007/0003114 A1 | 1/2007 | Hendriks et al. |
| 2009/0310831 A1* | 12/2009 | Zhang ............... G06K 9/00073 382/125 |
| 2012/0148087 A1 | 6/2012 | Xu et al. |

FOREIGN PATENT DOCUMENTS

| | | |
|---|---|---|
| JP | 3057590 B2 | 6/2000 |
| JP | 2004-118677 A | 4/2004 |
| JP | 2007-504524 A | 3/2007 |
| JP | 2012-129991 A | 7/2012 |
| JP | 2016-40682 A | 3/2016 |
| JP | 2016-40683 A | 3/2016 |

OTHER PUBLICATIONS

U.S. Appl. No. 16/370,044, filed Mar. 29, 2019 in the name of Kenji Miyoshino et al.
Nov. 8, 2016 International Search Report issued in International Patent Application No. PCT/JP2016/080019.
Dec. 19, 2017 International Search Report issued in International Patent Application No. PCT/JP2017/039416.
Dec. 19, 2017 International Search Report issued in International Patent Application No. PCT/JP2017/039417.
Anil K. Jain et al. "Pores and Ridges: High-Resolution Fingerprint Matching Using Level 3 Features". IEEE Transactions on Pattern Analysis and Machine Intelligence, vol. 29, No. 1, Jan. 2007, pp. 15-27.

* cited by examiner

FIG. 7

| BASE POINT ID | POSITION INFORMATION | FREQUENCY INFORMATION |
|---|---|---|
| P1 | (X1, Y1) | FJ1 |
| P2 | (X2, Y2) | FJ2 |
| P3 | (X3, Y3) | FJ3 |
| P4 | (X4, Y4) | FJ4 |
| P5 | (X5, Y5) | FJ5 |
| ⋮ | ⋮ | ⋮ |

98

| | RIDGE ID | BASE POINT ID | POSITION INFORMATION | RELATIVE ANGLE | DISTANCE | FREQUENCY INFORMATION |
|---|---|---|---|---|---|---|
| R1 { | L1 | P1 | (X1, Y1) | 0 | – | FJ11 |
| | | P2 | (X2, Y2) | AN2 | D1 | FJ21, FJ22 |
| | | P3 | (X3, Y3) | – | D2 | FJ32 |
| | | ⋮ | ⋮ | ⋮ | ⋮ | ⋮ |
| R6 { | L6 | P27 | (X27, Y27) | 0 | – | FJ261 |
| | | P28 | (X28, Y28) | AN28 | D27 | FJ271, FJ272 |
| | | P29 | (X29, Y29) | AN29 | D28 | FJ281, FJ282 |
| | | ⋮ | ⋮ | ⋮ | ⋮ | ⋮ |

FIG. 24

Table 92:

| RIDGE ID | | BASE POINT ID | POSITION INFORMATION | RELATIVE ANGLE | DISTANCE |
|---|---|---|---|---|---|
| V1 | Z1 | Q1 | (x1, y1) | 0 | – |
| | | Q2 | (x2, y2) | An2 | d1 |
| | | Q3 | (x3, y3) | An3 | d2 |
| | | Q4 | (x4, y4) | An4 | d3 |
| | | Q5 | (x5, y5) | An5 | d4 |
| | | Q6 | (x6, y6) | – | d5 |
| ⋮ | ⋮ | ⋮ | ⋮ | ⋮ | ⋮ |
| V5 | Z5 | Q24 | (x24, y24) | 0 | – |
| | | Q25 | (x25, y25) | An25 | d24 |
| | | Q26 | (x26, y26) | An26 | d25 |
| | | Q27 | (x27, y27) | – | d26 |

⇩

Table 93:

| RIDGE ID | | BASE POINT ID | BASE POINT ID | RELATIVE ANGLE | DISTANCE |
|---|---|---|---|---|---|
| v1 | z1 | Q6 | (x6, y6) | – | d5 |
| | | Q5 | (x5, y5) | –An5 | d4 |
| | | Q4 | (x4, y4) | –An4 | d3 |
| | | Q3 | (x3, y3) | –An3 | d2 |
| | | Q2 | (x2, y2) | –An2 | d1 |
| | | Q1 | (x1, y1) | 0 | – |
| ⋮ | ⋮ | ⋮ | ⋮ | ⋮ | ⋮ |
| v5 | z5 | Q27 | (x27, y27) | – | d26 |
| | | Q26 | (x26, y26) | –An26 | d25 |
| | | Q25 | (x25, y25) | –An25 | d24 |
| | | Q24 | (x24, x24) | 0 | d23 |

FIG. 29 ↙ 74

| COLLATION RIDGE ID | COLLATION BASE POINT ID | REGISTRATION RIDGE ID | REGISTRATION BASE POINT ID | SIMILARITY DEGREE W | REGISTRATION RIDGE ID | REGISTRATION BASE POINT ID | SIMILARITY DEGREE W |
|---|---|---|---|---|---|---|---|
| Z1 | Q1<br>Q2<br>Q3<br>Q4<br>Q5<br>Q6 | L2 | P4<br>P5<br>P6<br>P7<br>P8<br>P9 | W121 | — | — | — |
| Z2 | Q7<br>Q8<br>Q9<br>Q10<br>Q11<br>Q12 | L3 | P11<br>P12<br>P13<br>P14<br>P15<br>P16 | W231 | — | — | — |
| Z3 | Q7<br>Q8<br>Q9<br>Q15<br>Q16<br>Q17 | L4 | P11<br>P12<br>P13<br>P17<br>P18<br>P19 | W341 | — | — | — |
| Z4 | Q19<br>Q20<br>Q21<br>Q22<br>Q23 | L5 | P21<br>P22<br>P23<br>P24<br>P25 | W451 | — | — | — |
| Z5 | Q24<br>Q25<br>Q26<br>Q27 | L6 | P27<br>P28<br>P29<br>P30 | W561 | L5 | P20<br>P21<br>P22<br>P23 | W551 |

SKIN INFORMATION PROCESSING METHOD, SKIN INFORMATION PROCESSING DEVICE, AND NON-TRANSITORY COMPUTER-READABLE MEDIUM

CROSS REFERENCE TO RELATED APPLICATION

This application is a Continuation Application of International Application No. PCT/JP2017/039417, filed Oct. 31, 2017, which claims priority from Japanese Patent Application No. 2016-213899, filed on Oct. 31, 2016. This disclosure of the foregoing application is hereby incorporated by reference in its entirety.

BACKGROUND

The present disclosure relates to a skin information processing method, a skin information processing device, and a non-transitory computer-readable medium that are configured to analyze an image and generate collation information used for collation of biometric information.

Recently, various types of fingerprint authentication devices that can be installed in mobile devices, such as a smart phone and a notebook personal computer, have been proposed. For example, a known personal identification device that uses, as collation information used for collation, information obtained by performing frequency spectrum conversion on a fingerprint image. Thus, the personal identification device is unlikely to be affected by disturbance, such as inclination of a finger with respect to a fingerprint sensor.

SUMMARY

In accordance with miniaturization of a fingerprint sensor that is installed in a mobile device, an image of an acquired finger print becomes smaller than in related art. When a user performs an input operation of a fingerprint, in many cases, the user causes a finger of the hand that is holding the mobile device to touch the fingerprint sensor installed in the mobile device. In this case, since the user has to move the finger in an unnatural direction, the input operation of the fingerprint tends to become unstable. More specifically, an image acquired under conditions in which a position and an angle are different from those at the time of registration tends to be acquired. Accordingly, even when the size of the image is smaller than in the related art, a technology is required that generates collation information that is unlikely to be affected by acquisition conditions of biometric information.

Various embodiments of the broad principles derived herein provide a skin information processing method, a skin information processing device, and a non-transitory computer-readable medium that are capable of generating collation information that is unlikely to be affected by acquisition conditions of biometric information even when a size of an image representing the biometric information is smaller than in related art.

Embodiments provide a skin information processing method for a skin information processing device including a storage portion includes acquiring an image, determining a base point that represents a sweat pore on a ridge of skin, from the acquired image and acquiring position information corresponding to a position of the base point on the image, acquiring sample information indicating changes in color information around the determined base point, generating, as frequency information, information associating frequency components of the acquired sample information with the position information, and causing the storage portion to store information including the generated frequency information and the position information of the base point, as information used in skin authentication.

Embodiments also provide a skin information processing device that includes a processor, and a memory. The memory is configured to store computer-readable instructions that, when executed by the processor, instruct the processor to perform processes. The processes include acquiring an image, determining a base point that represents a sweat pore on a ridge of skin, from the acquired image and acquiring position information corresponding to a position of the base point on the image, acquiring sample information indicating changes in color information around the determined base point, generating, as frequency information, information associating frequency components of the acquired sample information with the position information, and causing the storage portion to store information including the generated frequency information and the position information of the base point, as information used in skin authentication.

Embodiments further provide a non-transitory computer-readable medium that stores computer-readable instructions that are executed by a processor provided in a skin information processing device including a storage portion, the computer-readable instructions, when executed, instructing the processor to perform processes. The processes include acquiring an image, determining a base point that represents a sweat pore on a ridge of skin, from the acquired image and acquiring position information corresponding to a position of the base point on the image, acquiring sample information indicating changes in color information around the determined base point, generating, as frequency information, information associating frequency components of the acquired sample information with the position information, and causing the storage portion to store information including the generated frequency information and the position information of the base point, as information used in skin authentication.

BRIEF DESCRIPTION OF THE DRAWINGS

Embodiments of the disclosure will be described below in detail with reference to the accompanying drawings in which:

FIG. 7 is an explanatory diagram of frequency information generated on the basis of the image;

FIG. 24 is an explanatory diagram of the ridge information;

FIG. 29 is an explanatory diagram of the pair range candidates selected by the pair range candidate selection processing shown in FIG. 26;

DETAILED DESCRIPTION OF EMBODIMENTS

An embodiment of the present disclosure will be explained with reference to the drawings. Specific numerical values exemplified in the embodiment below are examples, and the present disclosure is not limited to these numerical values. In the explanation below, image data is simply referred to as an "image."

A skin information processing device 10 that is common to first and second embodiments will be explained with reference to FIG. 1. The skin information processing device 10 is an electronic device is configured to generate, from skin information, collation information used for collation. The skin information is selected from among various types of biometric information represented by an image obtained by capturing hairless skin, such as a finger, a palm, a sole of a foot and the like. The skin information of a present embodiment is information relating to a fingerprint and sweat pores. The skin information processing device 10 is configured to analyze the image obtained by photographing a finger, generate collation information for collation that is necessary for the collation using the skin information, and determine a correspondence between the generated collation information for collation and the collation information for registration stored in the DB 28.

Figure 1:
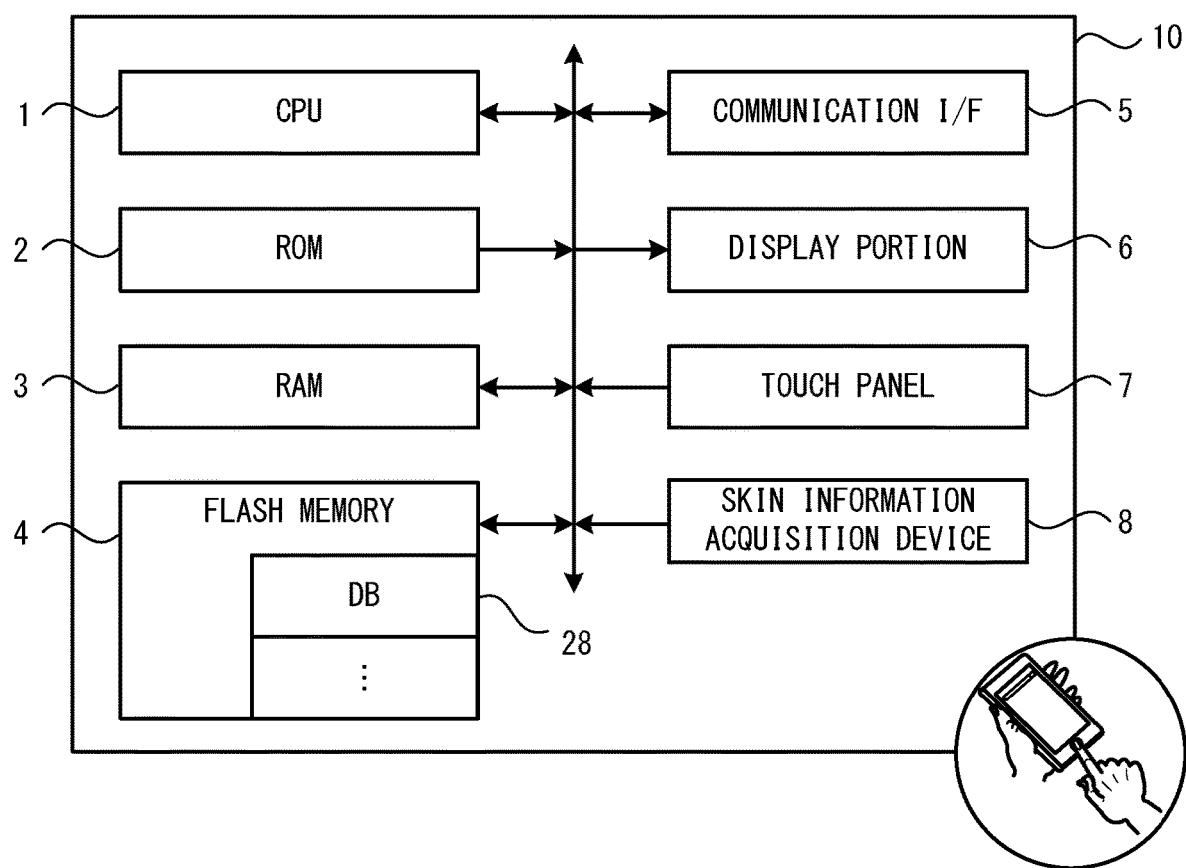
FIG. 1 is a block diagram of a skin information processing device.

As shown in FIG. 1, the skin information processing device 10 is provided with a CPU 1, a ROM 2, a RAM 3, the flash memory 4, a communication I/F 5, a display portion 6, a touch panel 7 and a skin information acquisition device 8. The CPU 1 is a processor that performs control of the skin information processing device 10. The CPU 1 is electrically connected to the ROM 2, the RAM 3, the flash memory 4, the communication I/F 5, the display portion 6, the touch panel 7 and the skin information acquisition device 8. The ROM 2 stores a BIOS, a boot program and initial setting values. The RAM 3 stores various temporary data. The flash memory 4 stores a program that is executed by the CPU 1 to control the skin information processing device 10, an operating system (OS) and the DB 28. The communication I/F 5 is a controller to perform communication with an external device. The display portion 6 is a liquid crystal display. The touch panel 7 is provided on the surface of the display portion 6. The skin information acquisition device 8 acquires a captured image of skin. The skin information acquisition device 8 of the present embodiment is an area-type optical sensor or a microscope, and shows color information per pixel using 256 gray-scale values. The color information is information indicating color. In order to acquire an image in which it is possible to ascertain the sweat pores, the resolution of the image is preferably 800 dots per inch (dpi) or greater. The resolution of the skin information processing device 10 of the present embodiment is 2000 dpi, for example.

Figure 2:
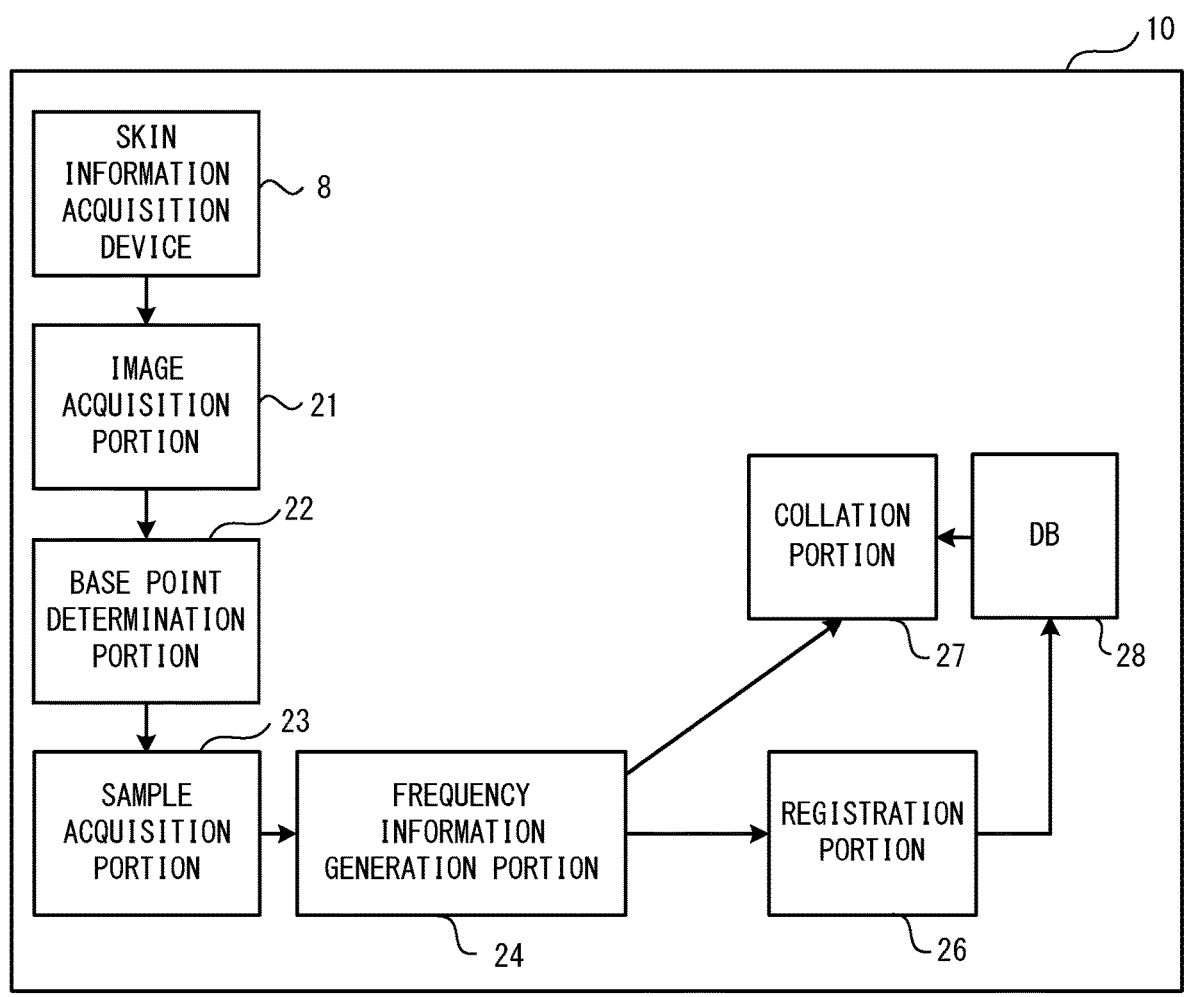
FIG. 2 is a functional block diagram of the skin information processing device.

Ridge information storage processing that is performed in the skin information processing device 10 of the first embodiment will be explained with reference to FIG. 2 to FIG. 7, using a specific example shown in FIG. 4. As shown in FIG. 2, the skin information processing device 10 includes the skin information acquisition device 8, an image acquisition portion 21, a base point determination portion 22, an sample acquisition portion 23, a frequency information generation portion 24, a registration portion 26, a collation portion 27 and the DB 28, and processing that corresponds to a functional block of each of them is performed by the CPU 1 (refer to FIG. 1).

Figure 3:
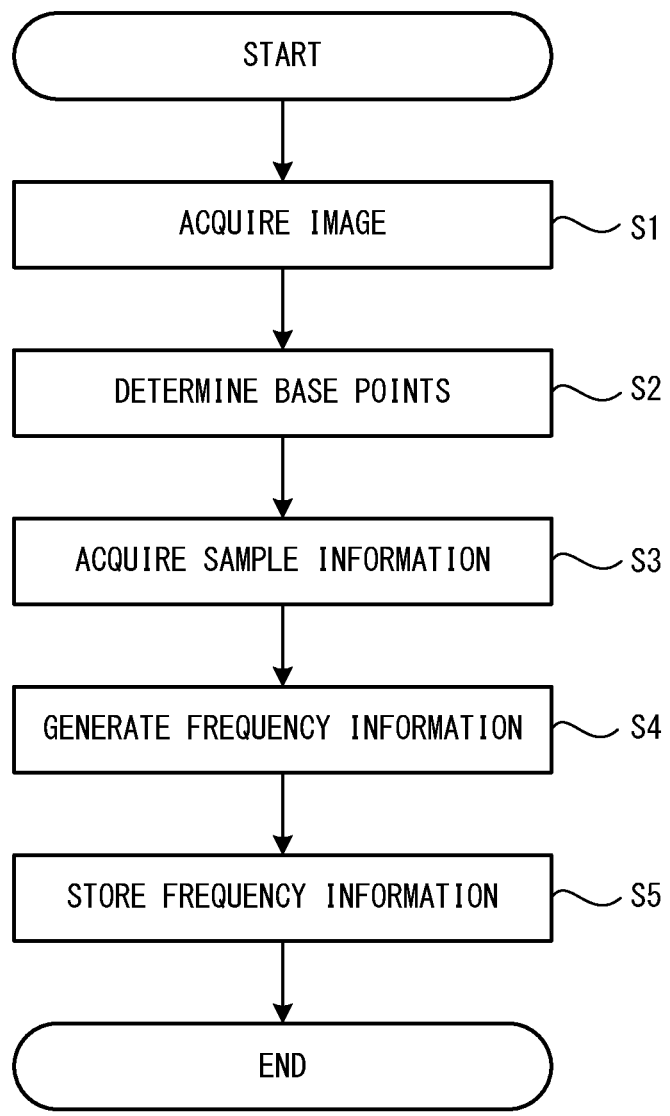
FIG. 3 is a flowchart of frequency information storage processing of a first embodiment.
Figure 4:
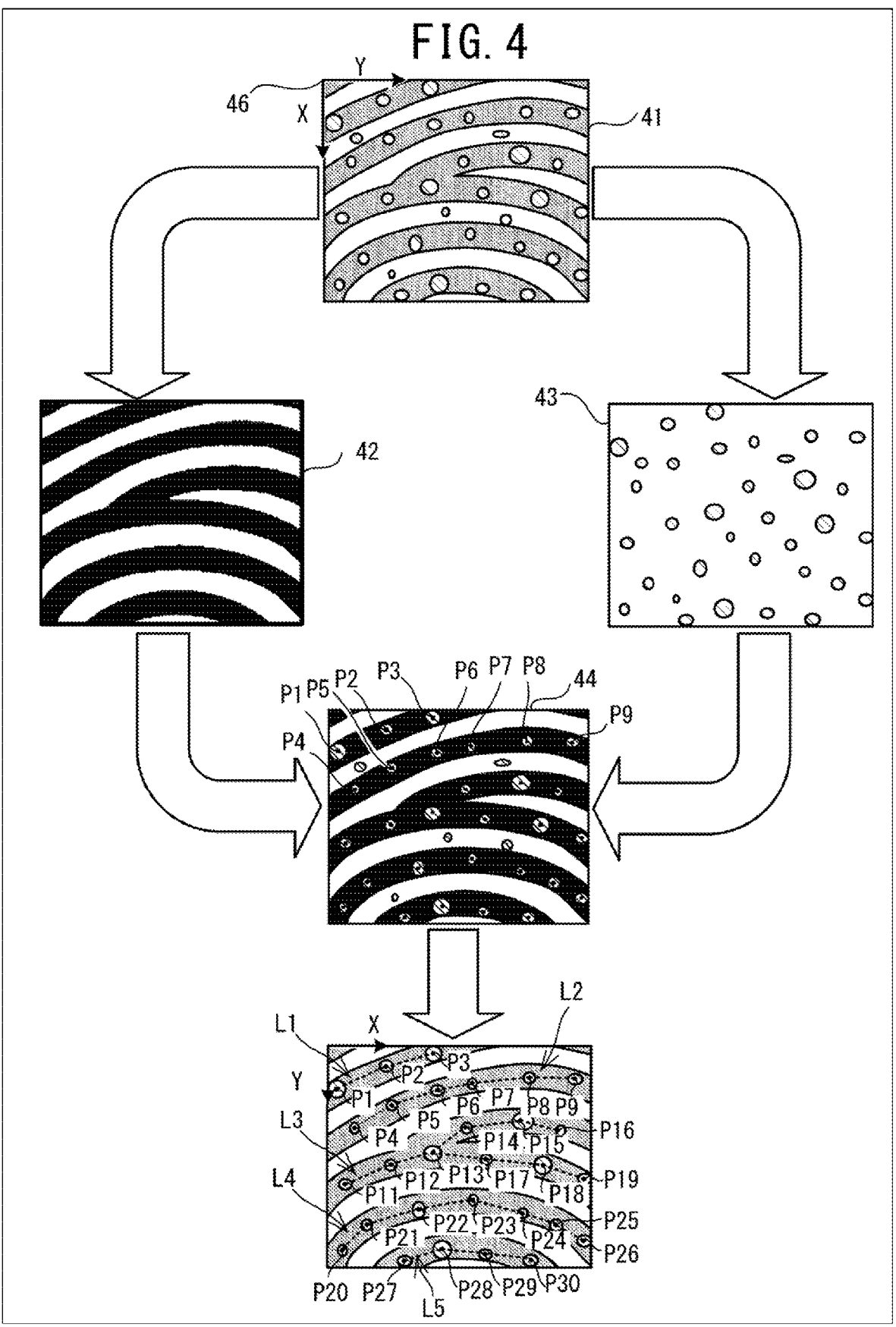
FIG. 4 is an explanatory diagram of a process to generate frequency information on the basis of an image.

As shown in FIG. 3, the skin information acquisition device 8 outputs an image to the image acquisition portion 21. The image acquisition portion 21 acquires the image output from the skin information acquisition device 8 (step S1). In the specific example, the skin information acquisition device 8 acquires an image 41. The resolution of the image 41 is 2000 dpi, for example, and the image 41 is an image schematically showing a part of a rectangular image of 480 pixels in the X direction (the left-right direction) and 800 pixels in the Y direction (the up-down direction). The base point determination portion 22 determines a base point representing a sweat pore on a ridge, from the image 41 acquired at step S1, and acquires position information corresponding to a position of the base point on the image (step S2). For example, the base point determination portion 22 determines an area centroid of an identified sweat pore to be the base point representing the sweat pore. The position information of the base point is represented, for example, by two-dimensional coordinates of an image coordinate system. It is assumed that the two-dimensional coordinates of the image coordinate system of the present embodiment are coordinates that are set in units of pixels, on the basis of positions of pixels in the image. In the image 41, the two-dimensional coordinates of the image coordinate system are set as represented by X and Y. The CPU 1 causes the position of a pixel on the top left of the image 41 to be an origin point of a two-dimensional coordinate 46 of the image coordinate system. The position of a pixel that is separated from the origin point of the two-dimensional coordinate 46 by x pixels in the X positive direction, and by y pixels in the Y positive direction, is represented by coordinates (x, y).

The base point determination portion 22 determines the base point using the following procedure, for example. As shown in FIG. 4, the base point determination portion 22 generates, from the image 41 acquired at step S1, an image 42 representing ridges, and an image 43 representing circular graphics that include sweat pores. The image 42 can be acquired, for example, by performing binarization processing on the image 41. In other examples, the image 42 can be obtained by applying the image 41 to a plurality of image processing filters that are used in processing of a minutia method. Within the image 42, black sections represent ridges, and white sections represent sections of troughs between the ridges. The image 43 can be obtained by applying the image 41 to an image processing filter that can extract a section of a particular range of gray values. The sweat pores are disposed on the ridges. The base point determination portion 22 compares the image 42 and the image 43 and identifies the circular sections disposed on the ridges indicated by the black sections as the sweat pores. The base point determination portion 22 determines the area centroid of the identified sweat pore to be the base point representing the sweat pore. In the processing at step S2, for example, a plurality of the base points are extracted, including base points P1 to P9 of an image 44.

The sample acquisition portion 23 acquires samples (step S3). The sample is information that associates the color information corresponding to a reference point with second position information corresponding to a position of the reference point on the image. The reference points are points surrounding the base point determined at step S2. For example, the CPU 1 sets the reference points as points on the circumference of a circle whose center is the base point P, in accordance with predetermined conditions. In accordance with the predetermined conditions, taking a starting point T1 as a reference, the CPU 1 sets 128 reference points Tm (m is an integer from 1 to 128) in order at equal intervals in the clockwise direction, on the circumference of a circle having a predetermined radius and centering on the selected base point P1. When the reference points Tm have coordinates in units of sub-pixels, the color information is acquired using known bilinear interpolation or bicubic interpolation. The CPU 1 acquires samples 95 that associate color information Cm corresponding to the reference points Tm with the second position information. The samples 95 are associated with first position information that indicates the position of the base point P1 on the image. It is sufficient that the first position information is information that defines the position of the base point P1 on the image. For example, the first position information may be absolute coordinates (for example, coordinates of the image coordinate system), relative coordinates, an acquisition order, or the like. The first position information of the present example is represented by the coordinates of the image coordinate system. It is sufficient that the second position information is information that defines the positions of the reference points Tm in relation to the base point P1. For example, the second position information may be absolute coordinates (for example, coordinates of the image coordinate system), relative coordinates, an angle in relation to a reference, or the like. When the order of acquisition of the reference points is determined with respect to a point used as the reference (the starting point, for example), the second position information may be the order of acquisition of the reference points. In the present example, the order of acquisition of the reference points Tm is acquired as the second position information. The order of acquisition of the reference points T1 to T128 is 1 to 128, respectively. The plurality of samples 95 are samples acquired for each of the plurality of reference points Tm whose positions are different from each other. The CPU 1 uses, as sample data 96, information that associates the plurality of samples 95 acquired for the single starting point T1 with the first position information.

Figure 5:
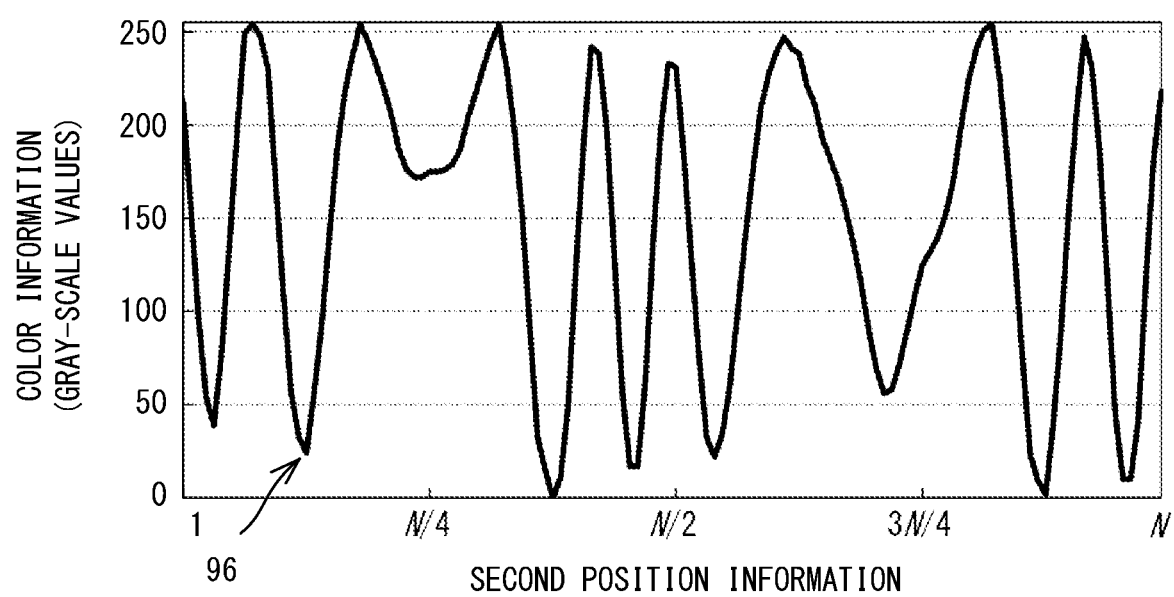
FIG. 5 is a graph showing changes in color information with respect to second position information, on the basis of a plurality of pieces of sample data.
Figure 6:
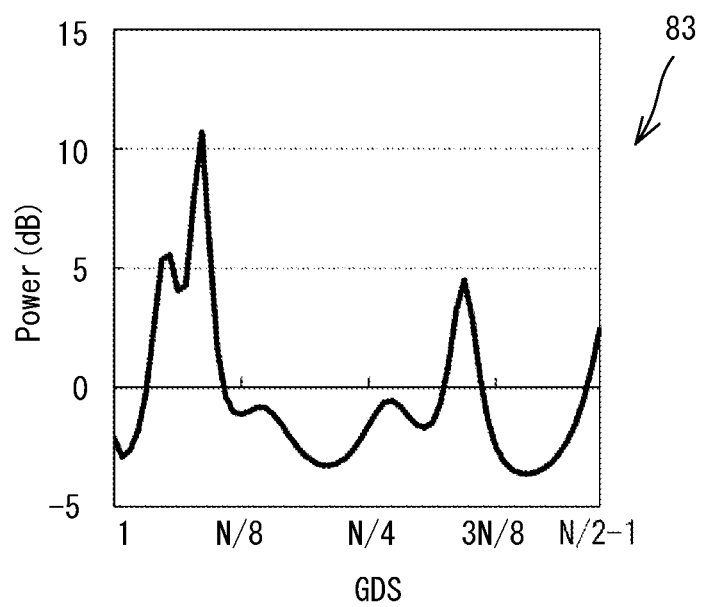
FIG. 6 is a graph showing frequency information generated for the plurality of pieces of sample data.

The frequency information generation portion 24 calculates frequency components of changes in the color information with respect to the second position information for the plurality of samples 95 (the sample data 96) acquired at step S116, and generates frequency information FJ (step S4). The frequency components are, for example, a known LPC spectrum, an LPC cepstrum, a group delay spectrum, and the like. The frequency components are, for example, the group delay spectrum (GDS), and are defined as the frequency derivative of a phase spectrum in a power transfer function. As shown in FIG. 5 and FIG. 6, a GDS 83 calculated on the basis of the sample data 96 separates and emphasizes individual peaks of the frequency spectrum of the sample data 96. As shown in a list 83 in FIG. 7, the frequency information FJ is associated with a base point ID and the position information of the base point.

The registration portion 26 associates the frequency information FJ generated at step S4 with the base points and stores the associated information in the DB 28 as the collation information for registration used in skin authentication (step S5). As shown in the list 84, the registration portion 26 stores the base point ID, the position information of the base point, and the frequency information FJ in association with each other. The collation portion 27 collates the collation information for collation with the collation information for registration stored in the DB 28, and performs the skin authentication. The skin information processing device 10 ends the processing.

1. Processing at Registration

The skin information processing performed by the skin information processing device 10 according to the second embodiment will be explained with reference to FIG. 8 to FIG. 34, taking a case of registering the collation information as an example. The skin information processing is started when a user inputs a start command. The start command includes a command relating to whether the collation information acquired from the image is to be registered in the DB 28 as the collation information for registration, or whether the similarity degree of the collation information with the collation information for registration registered in the DB 28 is to be calculated. When the CPU 1 of the skin information processing device 10 detects the input of the start command for the skin information processing, the CPU 1 reads out, to the RAM 3, a skin information processing program for performing the skin information processing stored in the flash memory 4, and performs each step of the processing (to be described below) in accordance with instructions included in the skin information processing program. In a present embodiment, feedback processing is performed that prompts re-input until biometric information is acquired that satisfies a condition (the sharpness of the image, for example) for extracting the feature points. The skin information acquired by the skin information processing satisfies a condition for extracting collation information from the skin information using an algorithm. Information and data acquired and generated in the course of the processing are stored in the RAM 3 as appropriate. Various setting values necessary to the processing are stored in advance in the flash memory 4. Hereinafter, step is abbreviated to "S".

Figure 8:
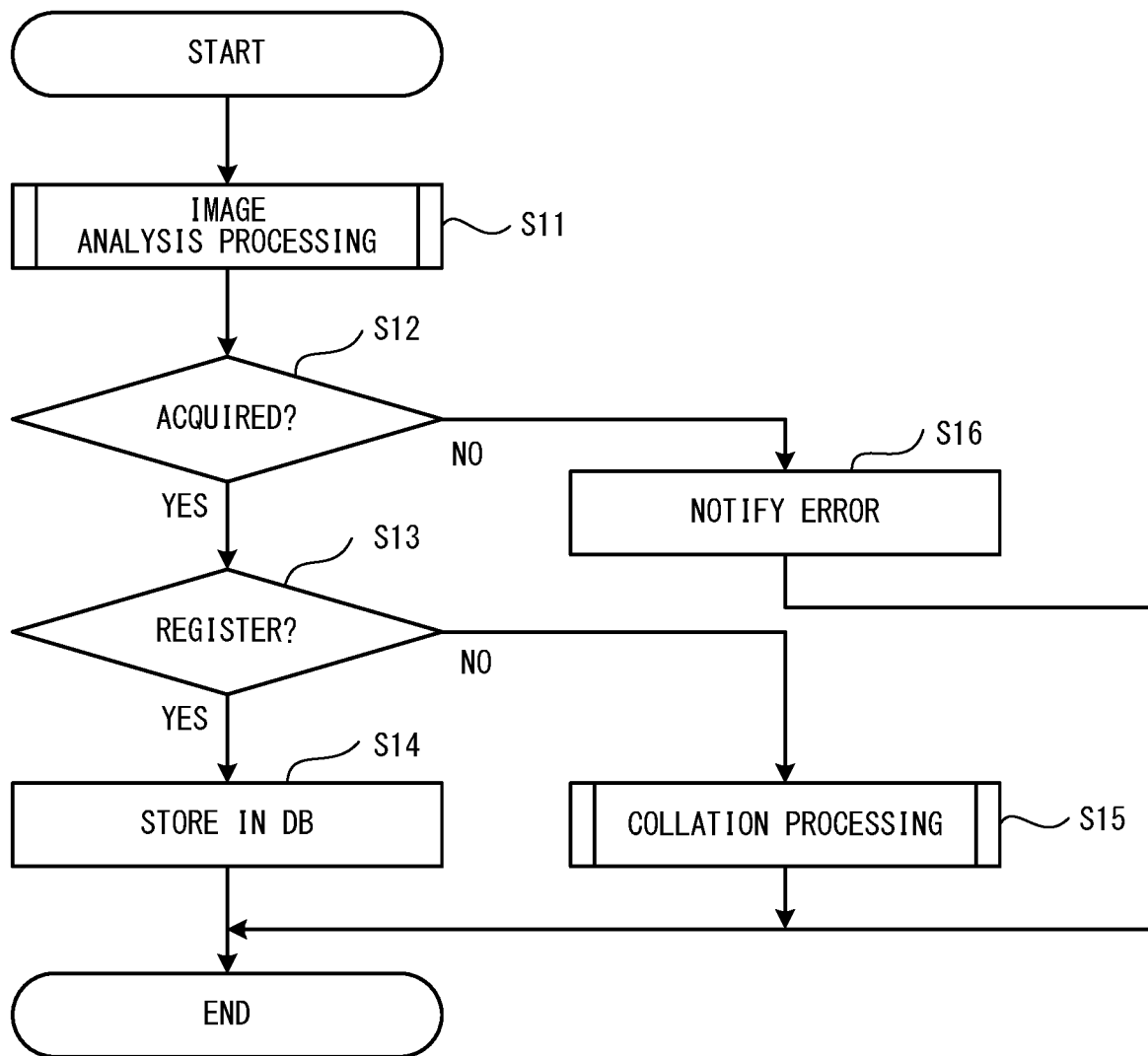
FIG. 8 is a flowchart of skin information processing of a second embodiment.

As shown in FIG. 8, the CPU 1 performs image analysis processing (S11). The image analysis processing will be explained with reference to FIG. 9. When contact of a finger is detected, the skin information acquisition device 8 outputs, to the CPU 1, a signal that can identify an image in which the fingerprint and the sweat pores are captured. The CPU 1 receives the output signal from the skin information acquisition device 8. The CPU 1 acquires the image on the basis of the received signal (S21). At S21, for example, the image 41 shown in FIG. 4 is acquired. Two-dimensional coordinates of an image coordinate system expressed by X and Y are set in the image 41. The CPU 1 performs binarization processing on the image 41 acquired at S21, and acquires the image 42 representing the ridges (S22). The CPU 1 determines the base points (S23). For example, the CPU 1 applies the image 41 to an image processing filter that can extract a section of a particular range of gray values and acquires the image 43, compares the image 42 with the image 43, and identifies the circular sections disposed on the ridges indicated by the black sections as the sweat pores. The CPU 1 determines the area centroid of the identified sweat pore to be the base point representing the sweat pore, and acquires position information of the determined base point. The position information of the present embodiment is formed of pixel unit coordinates of the image coordinate system. The CPU 1 may take the size and shape etc. of the circular section into account, as necessary, and determine whether or not to determine the circular section to be the sweat pore. The CPU 1 determines whether or not the numbers of base points determined at S23 is larger than zero (S24). When the number of base points acquired at S23 is zero (no at S24), the CPU 1 ends the image analysis processing and returns the processing to the skin information processing shown in FIG. 8. When the number of base points acquired at S23 is greater than zero (yes at S24), the CPU 1 performs connection information generation processing.

Figure 10:
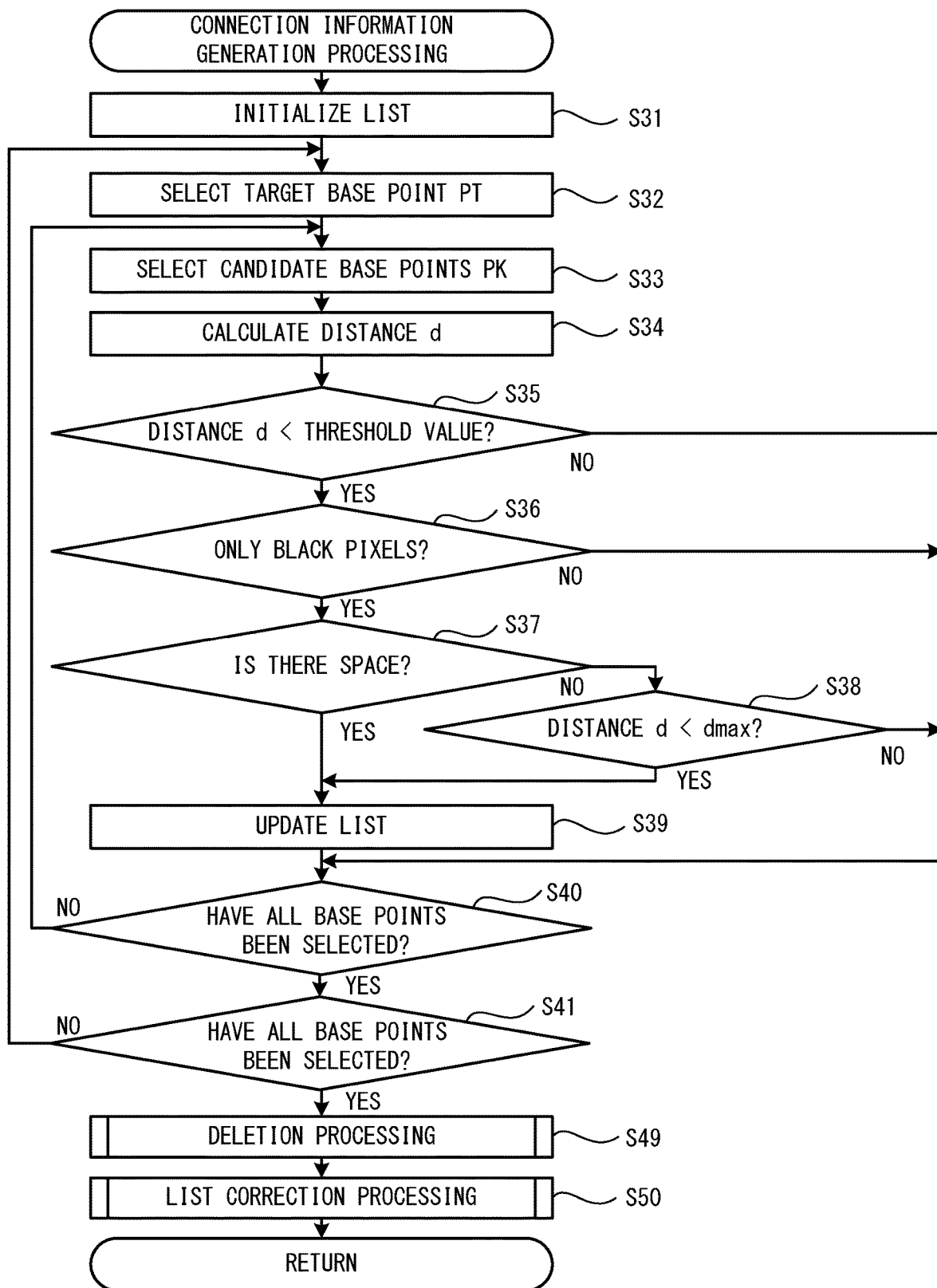
FIG. 10 is a flowchart of connection information generation processing performed in the image analysis processing shown in FIG. 9.

As shown in FIG. 10, in the connection information generation processing, the CPU 1 initializes a list (S31). The list stores the connection information. When it is assumed that each of the plurality of base points determined in the processing at S23 is a target base point PT, the connection information is information that associates position information of the target base point PT with position information of a connection base point PB. The connection base point PB is a base point that is disposed on the same continuous ridge as the target base point PT, and that precedes or follows the target base point PT in the arrangement order on the same continuous ridge. The CPU 1 selects, as the target base point PT, one of the plurality of base points determined in the processing at S23 (S32). For example, the base point P1 in the image 44 shown in FIG. 4 is selected as the target base point PT. The CPU 1 selects a single candidate base point PK as a candidate for the connection base point PB (S33). For example, the CPU 1 acquires, as the candidate base points PK, the base points in order of closeness (based on a Euclidean distance, for example) from the target base point PT, from among the plurality of base points determined in the processing at S23, for example. The CPU 1 selects the base point P4 as the candidate base point PK, for example. The CPU 1 calculates a distance d between the target base point PT selected in the processing at S32 and the candidate base point PK selected in the processing at S33 (S34). The distance d is a Euclidean distance calculated on the basis of the position information of the target base point PT and the position information of the candidate base point PK, for example.

The CPU 1 determines whether the distance d calculated at S34 is smaller than a threshold value (S35). The threshold value is set as appropriate while taking into account the distribution of the sweat pores on the skin. When the distance d is not smaller than the threshold value (no at S35), the CPU 1 performs processing at S40 to be described later. When the distance d is smaller than the threshold value (yes at S35), the CPU 1 refers to the image 42 and determines whether or not only black pixels are present between the target base point PT and the candidate base point PK (S36). For example, white pixels are present between the target base point P1 and the candidate base point P4 (no at S36). In this case, the CPU 1 determines that the target base point PT and the candidate base point PK are not disposed on the same continuous ridge. Thus, the CPU 1 determines whether, in the processing at S33, the base point other than the target base point PT has been selected as the candidate base point PK from among the plurality of base points determined in the processing at S23 (S40). When there is the base point that has not been selected as the candidate base point PK in the processing at S33 (no at S40), the CPU 1 selects the next candidate base point PK (S33). For example, when P2 is selected as the candidate base point PK, the calculated distance d is smaller than the threshold value (yes at S35), and the CPU 1 determines that only black pixels are present between the base point P1 and the base point P2 (yes at S36). The CPU 1 determines whether there is a space in the list for the target base point PT (S37). In the present embodiment, a predetermined number of the connection base points PB can be set for each one of the target base points PT, and an upper limit is set for the number of the connection base points PB that can be registered in the list. Taking into account the number of bifurcations of the ridge, the predetermined number is 4, for example.

When there is no space in the list (no at S37), the CPU 1 determines whether the distance d calculated at S34 is smaller than a value dmax (S38). dmax is a maximum value of the distance d stored in the list. When the distance d is not smaller than dmax (no at S38), the CPU 1 performs the processing at S40. When the distance d is smaller than dmax (yes at S38), within the list for the target base points PT, the candidate base point PK that is dmax is deleted, the candidate base point PK selected at S33 is added to the list in place of the deleted candidate base point PK, and the list is updated (S39). In the processing at S37, when there is space in the list for the target base points PT (yes at S37), the CPU 1 adds the candidate base point PK selected at S33 to the list for the target base points PT (S39). When, among the plurality of base points determined in the processing at S23, there are the base points other than the target base point PT that have not been selected as the candidate base point PK in the processing at S33 (no at S40), the CPU 1 returns the processing to S33. At S39 that is repeatedly performed, as shown by a list 81 in FIG. 11, for the base point P1, the base points P2 and P3 are stored in the list. When all the base points other than the target base point PT have been selected as the candidate base point PK (yes at S40), the CPU 1 determines whether all the base points have been selected as the target base point PT in the processing at S32 (S41). When there is the base point that has not been selected as the target base point PT (no at S41), the CPU 1 returns the processing to S32. When all of the base points have been selected as the target base point PT (yes at S41), the CPU 1 performs deletion processing (S49). In the deletion processing, processing is performed to delete from the list the base points that do not precede or follow the target base point PT in the arrangement order of the ridges.

Figure 12:
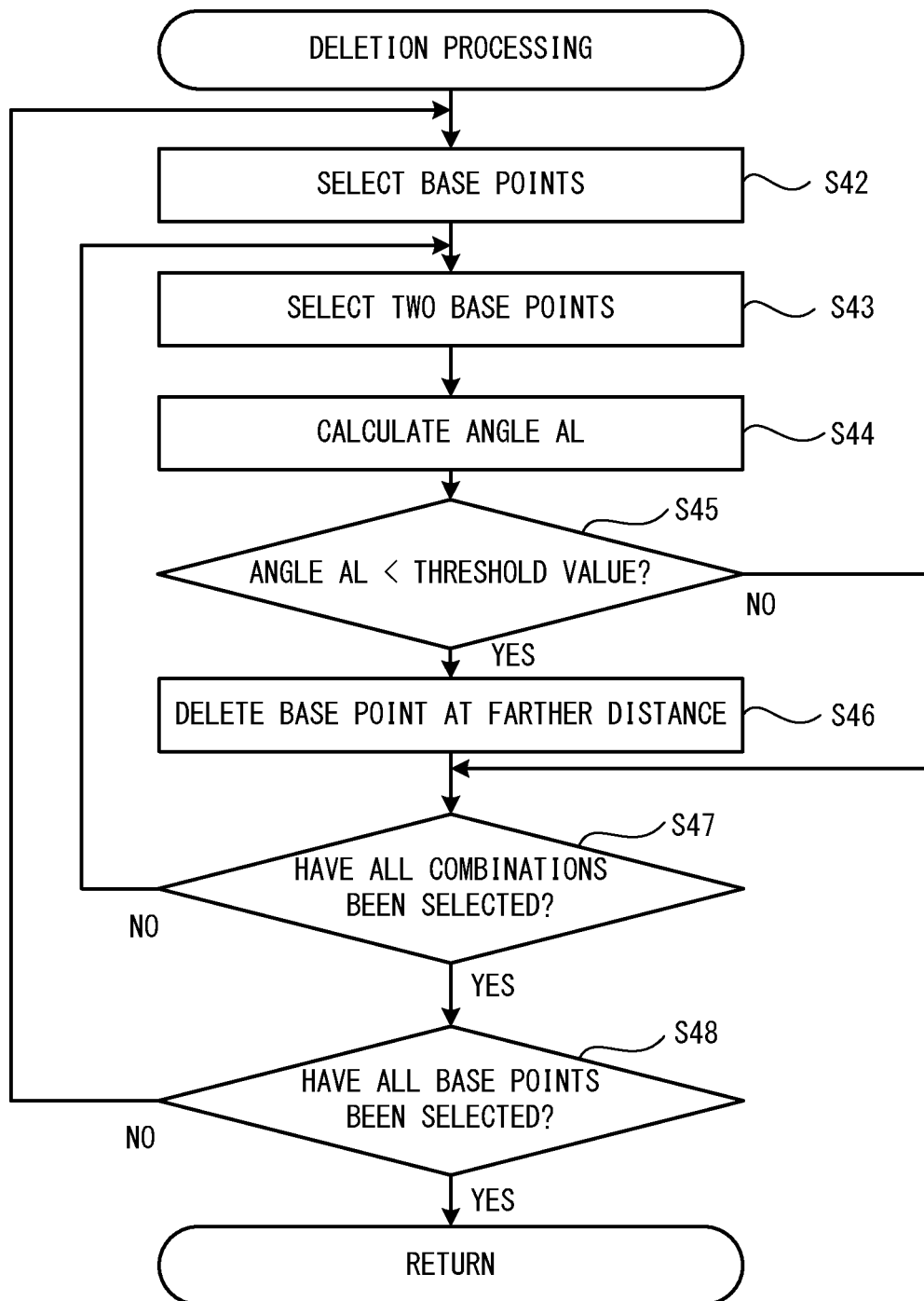
FIG. 12 is a flowchart of deletion processing that is performed in the connection information generation processing shown in FIG. 10.

As shown in FIG. 12, in the deletion processing, the CPU 1 selects the base point, for which two or more candidate base points PK are stored, from among the plurality of base points, as the target base point PT (S42). For example, the CPU 1 selects the base point P1 as the target base point PT. The CPU 1 selects two base points from among the two or more candidate base points PK for the target base point PT selected at S42 (S43). The CPU 1 selects the base points P2 and P3 as the two base points, for example. The CPU 1 calculates an angle AL, which is an angle formed between two line segments formed by connecting each of the two base points selected at S43 and the target base point PT (S44). For example, the CPU 1 calculates the angle AL formed between a first line segment connecting the base point P1 and the base point P2, and a second line segment connecting the base point P1 and the base point P3. The CPU 1 determines whether the angle AL calculated at S44 is smaller than a threshold value (S45). The threshold value at S45 is set while taking into account a bending range of the ridge and an interval between the sweat pores.

Figure 11:
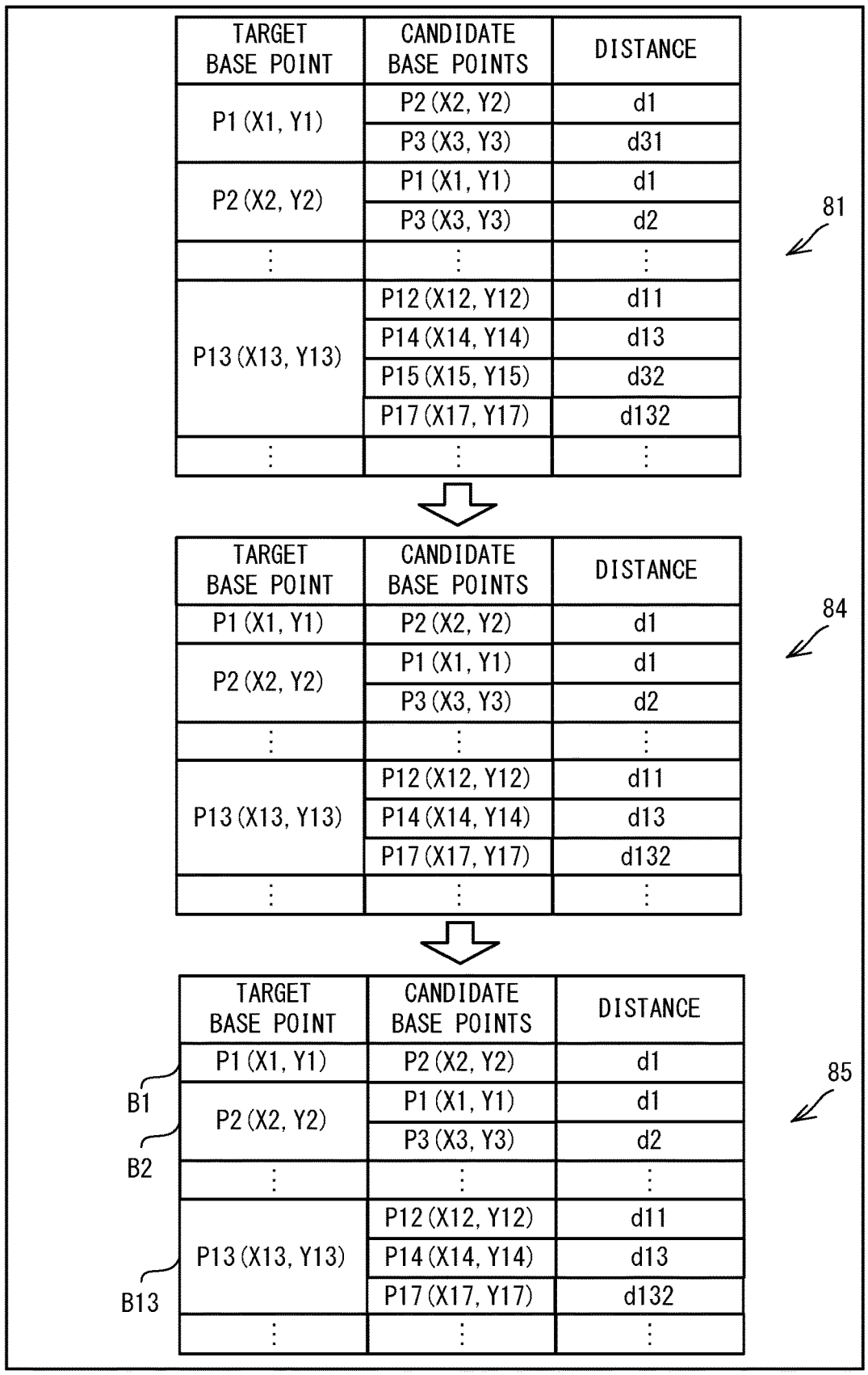
FIG. 11 is an explanatory diagram of a process that generates connection information.

In the specific example, it is determined that the angle AL formed between the first line segment and the second line segment is smaller than the threshold value (yes at S45), and, of the two base points P2 and P3 selected at S43, the base point P3 for which the distance from the base point P1 selected at S42 is farther is deleted from the list (S46). When the angle AL is not smaller than the threshold value (no at S45), or after the processing at S46, the CPU 1 determines whether all combinations of the two or more candidate base points PK stored for the target base point P1 have been selected (S47). When there is a combination that has not been selected at S43 (no at S47), the CPU 1 returns the processing to S43. For the base point P1, there are no combinations that have not been selected at S43 (yes at S47). In this case, the CPU 1 determines whether all of the base points for which the two or more candidate base points PK are stored have been selected as the target base point PT in the processing at S42 (S48). Of the base points for which the two or more candidate base points PK are stored, when there are the base points that have not been selected as the target base point PT in the processing at S42 (no at S48), the CPU 1 returns the processing to S42. When all of the base points for which the two or more candidate base points PK are stored have been selected as the target base point PT in the processing at S42 (yes at S48), the CPU 1 ends the deletion processing, and returns the processing to the connection information generation processing shown in FIG. 10. As a result of the deletion processing, some of the candidate base points PK stored in the list 81 shown in FIG. 11 are deleted and updated to a list 84.

Figure 13:
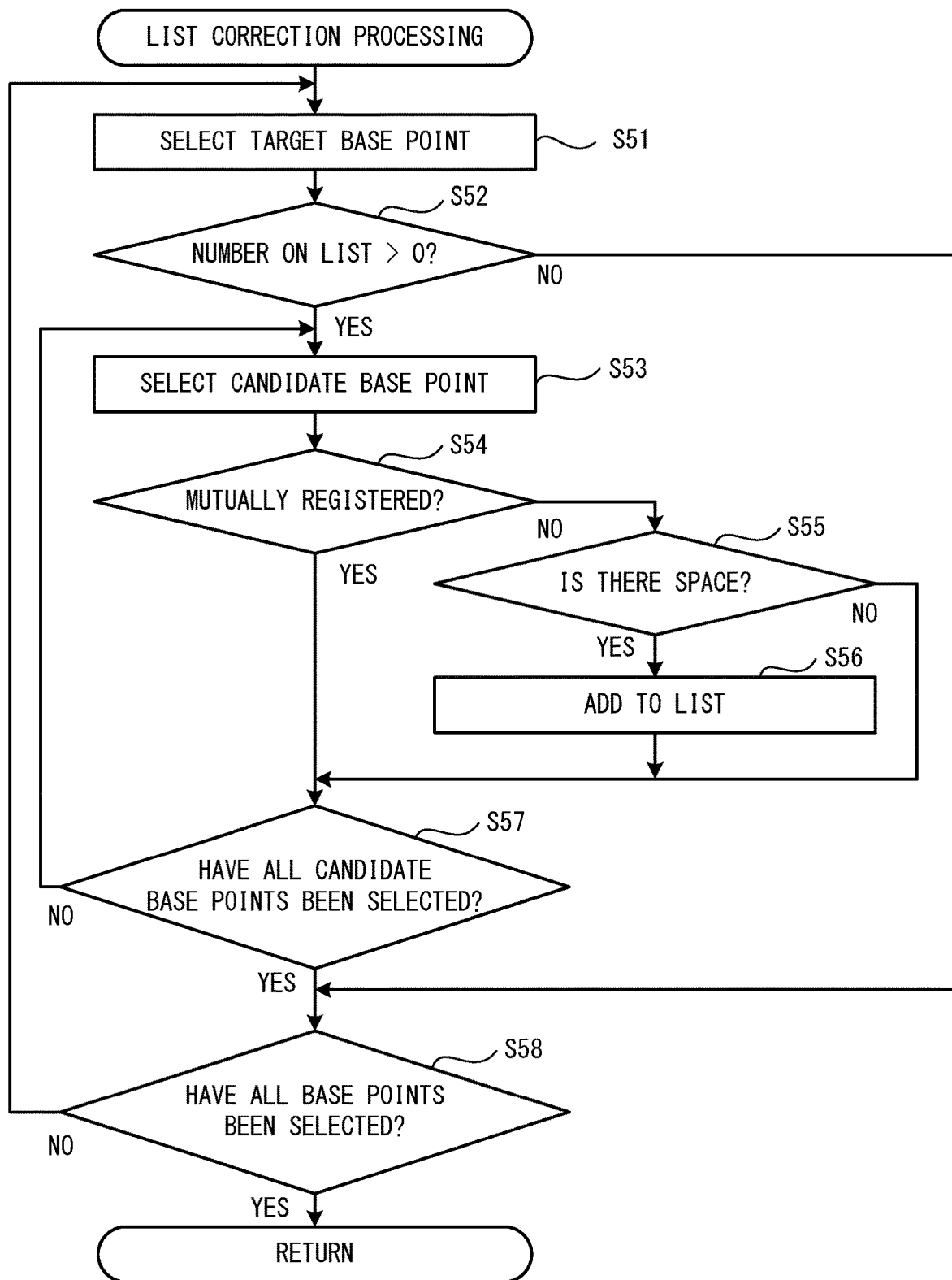
FIG. 13 is a flowchart of list correction processing that is performed in the connection information generation processing shown in FIG. 10.

As shown in FIG. 10, the CPU 1 performs list correction processing after the processing at S49 (S50). The list correction processing is processing to correct the list such that the target base point PT is stored as the candidate base point PK, when the candidate base point PK stored for the target base point PT is taken as the target base point PT. As shown in FIG. 13, in the list correction processing, the CPU 1 selects, from among the plurality of base points, one of the base points as the target base point PT (S51). For example, the CPU 1 selects the base point P1 as the target base point PT. The CPU 1 determines whether the number of the candidate base points PK stored for the target base point PT selected at S51 is greater than zero (S52). When the number of the candidate base points PK is not greater than zero (no at S52), the CPU 1 performs processing at S58 to be described later. The one candidate base point PK is stored for the target base point P1 (yes at S52), and thus the CPU 1 selects the one candidate base point PK for the target base point PT selected at S51, from the list (S53). The CPU 1 selects the base point P2 as the candidate base point PK for the base point P1. The CPU 1 determines whether the base point P1 selected at S51 is stored in the list as the candidate base point PK for the base point P2 selected at S53 (S54). When the base point selected at S51 is not stored as the candidate base point PK for the base point selected at S53 (no at S54), if there is a space in the list of the base points selected at S53 (yes at S55), the CPU 1 stores the base point selected at S51 as the candidate base point PK for the base point selected at S53 (S56). When there is no space in the list of the base points selected at S53 (no at S55), or after the processing at S56, the CPU 1 performs processing at S57.

The base point P1 is stored in the list as the candidate base point PK for the base point P2 (yes at S54). In this case, the CPU 1 determines whether all of the candidate base points PK for the target base point PT selected at S51 have been selected in the processing at S53 (S57). Of the candidate base points PK for the target base point PT, when there is the base point that has not been selected in the processing at S53 (no at S57), the CPU 1 returns the processing to S53. When all the candidate base points PK for the target base point PT have been selected in the processing at S53 (yes at S57), the CPU 1 determines whether all of the plurality of base points have been selected as the target base point PT in the processing at S51 (S58). When there is the base point that has not been selected as the target base point PT (no at S58), the CPU 1 returns the processing to S51. When all the base points have been selected as the target base point PT (yes at S58), the CPU 1 ends the list correction processing and returns the processing to the connection information generation processing shown in FIG. 10. After ending the list correction processing at S50, the CPU 1 ends the connection information generation processing and returns the processing to the image analysis processing shown in FIG. 9. The candidate base point PK resulting from the connection information generation processing is identified as the connection base point PB for the target base point PT, and the position information of the target base point PT and the position information of the connection base point PB are associated with each other and stored as connection information 85. As shown in FIG. 11, in the connection information 85, for example, the position information of the base point P1 and the position information of the base point P2 are associated with each other as connection information B1 for the base point P1. The position information of the base point P2, and the position information of the base points P1 and P3 are associated with each other as connection information B2 for the base point P2.

Figure 9:
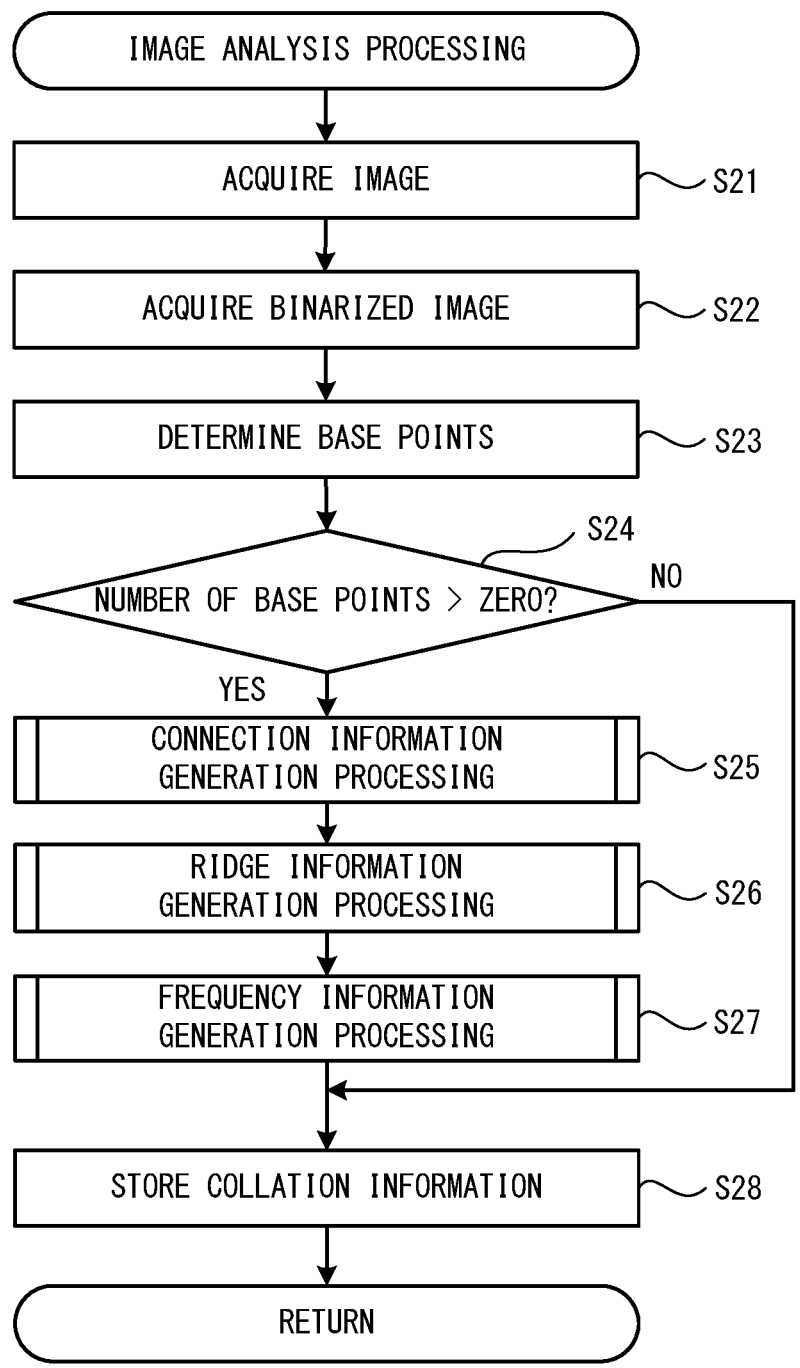
FIG. 9 is a flowchart of image analysis processing that is performed in the skin information processing shown in FIG. 8.
Figure 14:
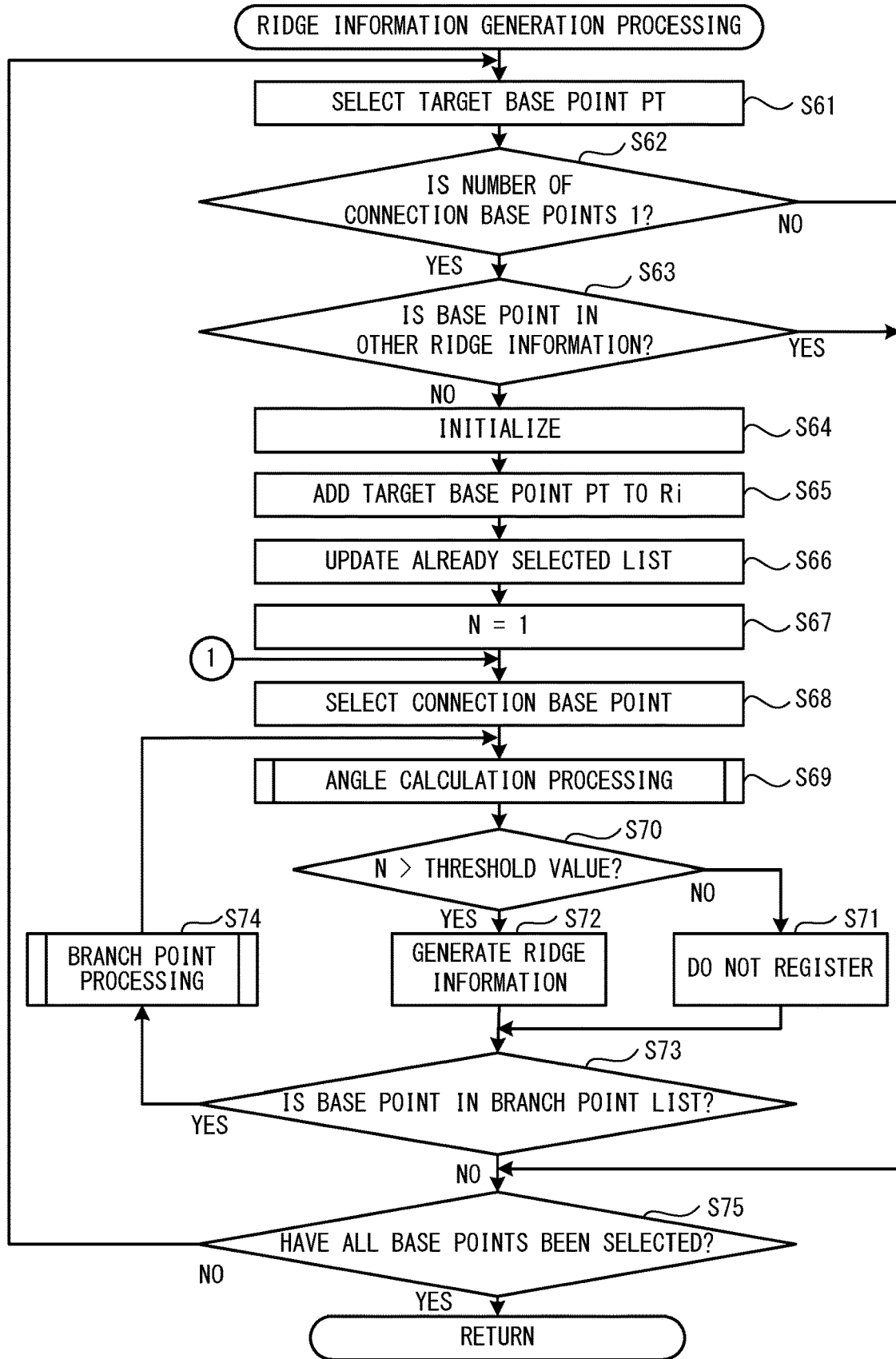
FIG. 14 is a flowchart of ridge information generation processing that is performed in the image analysis processing shown in FIG. 9.

As shown in FIG. 9, after the processing at S25, the CPU 1 performs ridge information generation processing (S26). As shown in FIG. 14, in the ridge information generation processing, the CPU 1 selects one of the base points from among the plurality of base points as the target base point PT (S61). For example, the CPU 1 selects the base point P1 shown in FIG. 15 as the target base point PT. The CPU 1 refers to the connection information 85 generated in the processing at S25, and determines whether the number of the connection base points PB stored for the target base point PT selected in the processing at S61 is 1 (S62). By the processing at S62, on the basis of the connection information, the CPU 1 identifies, among the plurality of base points, the base point for which a number of preceding and following base points in the arrangement order is 1, and identifies the first base point in the arrangement order as a start point and the last base point in the arrangement order as an end point. When the number of the connection base points PB is not 1 (no at S62), the CPU 1 performs processing at S75 to be described later. For the base point P1, the number of the connection base points PB is 1 (yes at S62). In this case, the CPU 1 refers to the already stored ridge information and determines whether the target base point PT selected in the processing at S61 is not stored as the base point of the other ridge information (S63). When the target base point PT selected in the processing at S61 is stored as the base point of the other ridge information, for example, for the base point for which the number of preceding and following base points in the arrangement order is 1, the target base point PT is identified as the last base point in the arrangement order in the other ridge information. When the target base point PT is stored as the base point of the other ridge information (yes at S63), the CPU 1 performs the processing at S75 to be described later. The base point P1 is not stored as the base point of the other ridge information (no at S63). In this case, the CPU 1 performs initialization processing relating to ridge information Ri (S64). In the initialization processing relating to the ridge information Ri, the CPU 1 initializes the i-th ridge information Ri, a branch point list, and an already selected list, and sets values to NULL. i is a natural number indicating a registration order of the ridge information. The initial value of i is 1, and is incremented in accordance with the number of the already registered ridge information. The CPU 1 adds the target base point PT to the ridge information Ri (S65). For example, as in a list 86 shown in FIG. 16, the CPU 1 adds the base point ID and the position information (X1, Y1) of the base point P1 to ridge information R1. By repeating the processing at S65, on the basis of the connection information generated in the processing at S25, the plurality of base points disposed on the same continuous ridge are extracted in order. The CPU 1 adds the base point P1 to the already selected list, and updates the already selected list (S66). The CPU 1 sets a various N to 1, the variable N indicating the number of the base points included in the ridge information Ri (S67).

Figure 17:
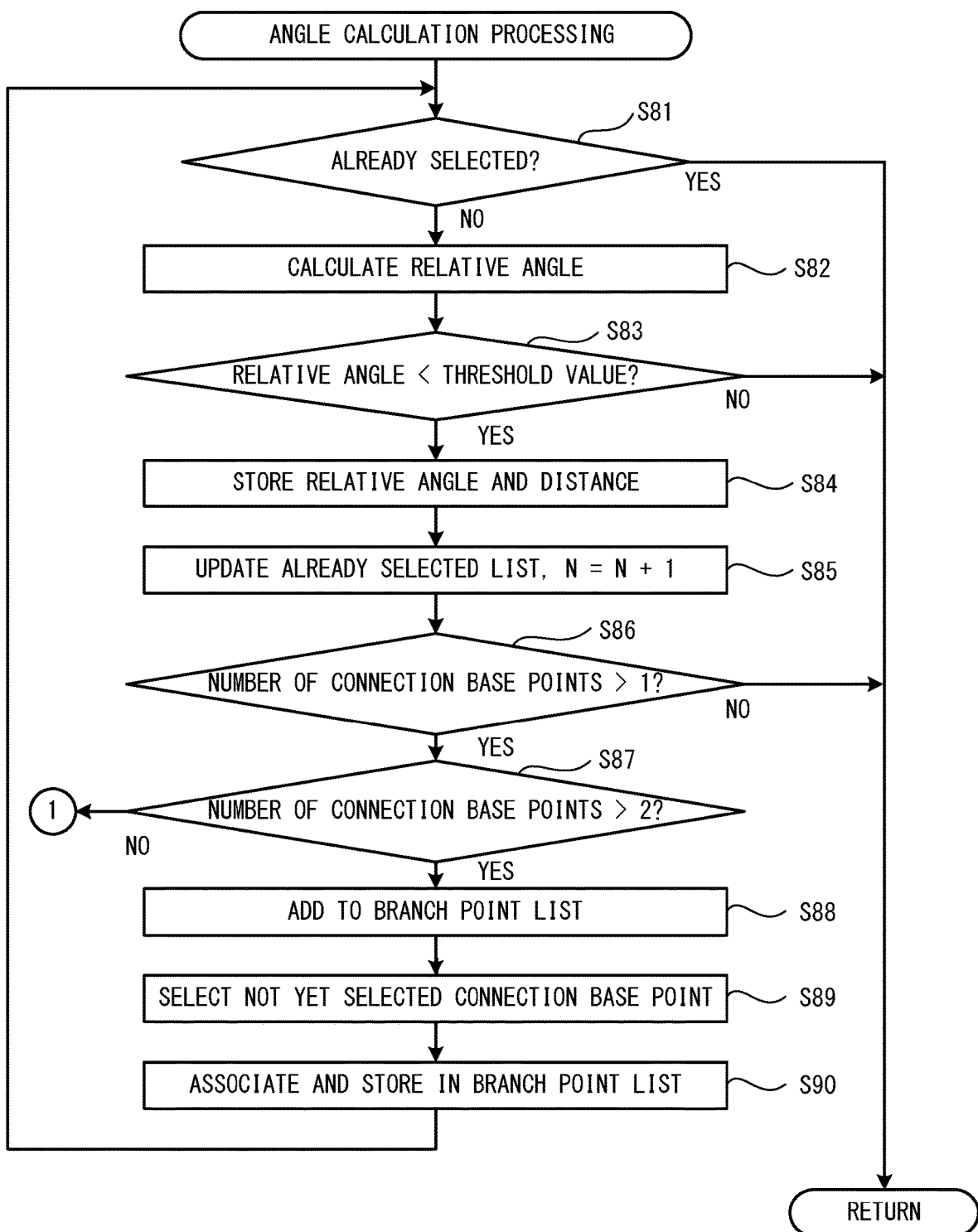
FIG. 17 is a flowchart of angle calculation processing that is performed in the ridge information generation processing shown in FIG. 14.

The CPU 1 refers to the connection information 85 generated in the processing at S25, and selects, as a selected base point, the connection base point PB stored for the target base point PT selected in the processing at S61 (S68). For example, the CPU 1 selects the base point P2 as the selected base point. The CPU 1 performs angle calculation processing (S69). As shown in FIG. 17, in the angle calculation processing, the CPU 1 determines whether the selected base point has already been stored as the base point of the other ridge information (S81). When the selected base point has been stored as the base point of the other ridge information (yes at S81), the CPU 1 ends the angle calculation processing and returns the processing to the ridge information generation processing shown in FIG. 14. As shown by the list 86 in FIG. 16, the base point P2 is not stored as the base point in the other ridge information (no at S81). In this case, the CPU 1 calculates a relative angle for the selected base point (S82). The relative angle is an angle of the second line segment connecting the N-th base point in the arrangement order and the (N+1)-th selected base point in the arrangement order with respect to the first line segment connecting the (N−1)-th base point in the arrangement order and the N-th base point in the arrangement order. In other words, the relative angle is the angle of the line segment connecting the N-th base point and the following base point in the arrangement order with respect to the line segment connecting the N-th base point and the preceding base point in the arrangement order. When N is 1, the CPU 1 sets the relative angle as zero. When N is 2 or more, the CPU 1 defines the first line segment and the second line segment and calculates the relative angle. In the present embodiment, an angle in the clockwise direction from the first line segment is taken as a positive angle, and an angle in the counterclockwise direction from the first line segment is taken as a negative angle, and the relative angle is represented by an angle from −180 degrees to 180 degrees. In the specific example, N is 1, and thus the CPU 1 sets the relative angle for the base point P1 as zero.

The CPU 1 determines whether the relative angle calculated at S82 is smaller than a threshold value (S83). When the relative angle is not smaller than the threshold value (no at S83), the CPU 1 ends the angle calculation processing and returns the processing to the ridge information generation processing shown in FIG. 14. When the relative angle is smaller than the threshold value (yes at S83), the CPU 1 adds the selected base point to the ridge information Ri (S84). The CPU 1 adds the base point ID and the position information of the selected base point, a relative angle AN calculated at S82, and the distance d between the target base point PT included in the connection information and the selected base point to the ridge information Ri. The CPU 1 adds the base point P2 to the ridge information R1, as shown in a list 87 in FIG. 16. The CPU 1 adds the selected base point to the already selected list and updates the already selected list. The CPU 1 increments N by 1 (S85).

The CPU 1 refers to the connection information 85 generated in the processing at S25 and determines whether the number of the connection base points PB stored for the selected base point is greater than 1 (S86). The selected base point for which the number of the connection base points PB is 1 is the other end of the ridge. When the number of the connection base points PB is not greater than 1 (no at S86), the CPU 1 ends the angle calculation processing and returns the processing to the ridge information generation processing shown in FIG. 14. When the number of the connection base points PB is greater than 1 (yes at S86), the CPU 1 determines whether the number of the connection base points PB is greater than 2 (S87). The processing at S87 is processing to identify, among the plurality of base points, the base point for which the number of preceding and following base points in the arrangement order is 3 or more, as the branch point of the ridge, on the basis of the connection information. Processing that is performed when the number of the connection base points PB is greater than 2 (yes at S87) will be described later. The number of the connection base points PB for the base point P2 is 2 (no at S87). In this case, the CPU 1 sets the selected base point as the target base point PT and returns the processing to S68 in FIG. 14. At S68 that is repeatedly performed, when the target base point PT is the base point P2, the CPU 1 selects the base point P3 as the connection base point (S68). In the angle calculation processing shown in FIG. 17, it is determined that the base point P3 has not yet been selected (yes at S81), and a relative angle AN2 is calculated (S82). It is determined that the relative angle AN2 is smaller than the threshold value (yes at S83), and the CPU 1 adds the base point P3 to the ridge information R1, as shown in a list 88 in FIG. 16 (S84). The CPU 1 adds the base point P3 to the already selected list and updates the already selected list. The CPU 1 increments N by 1 (S85). Since the number of the connection base points PB for the base point P3 is 1 (no at S86), the CPU 1 ends the angle calculation processing and returns the processing to the ridge information generation processing shown in FIG. 14. In this way, when the continuous ridge does not include the branch point, the CPU 1 defines the ridge having no bifurcations from the start point to the end point, extracts the plurality of base points disposed on the defined ridge, and generates the ridge information.

In the ridge information generation processing shown in FIG. 14, the CPU 1 determines whether or not the variable N is larger than a threshold value (S70). The processing at S70 is processing to generate only the ridge information including the number of base points greater than the threshold value. The threshold value is 2, for example. If the variable N is not larger than the threshold value (no at S70), the CPU 1 deletes the ridge information Ri without registering it (S71). For the ridge information R1, the variable N is 3 and is larger than the threshold value (yes at S70). In this case, the CPU 1 generates the ridge information R1 (S72). After step S72 or step S71, the CPU 1 determines whether the base point is included in the branch point list (S73). When the base point is included in the branch point list (yes at S73), the CPU 1 performs branch point processing (S74). When the base point is not included in the branch point list (no at S73), the CPU 1 performs the processing at S75 to be described later.

Figure 15:
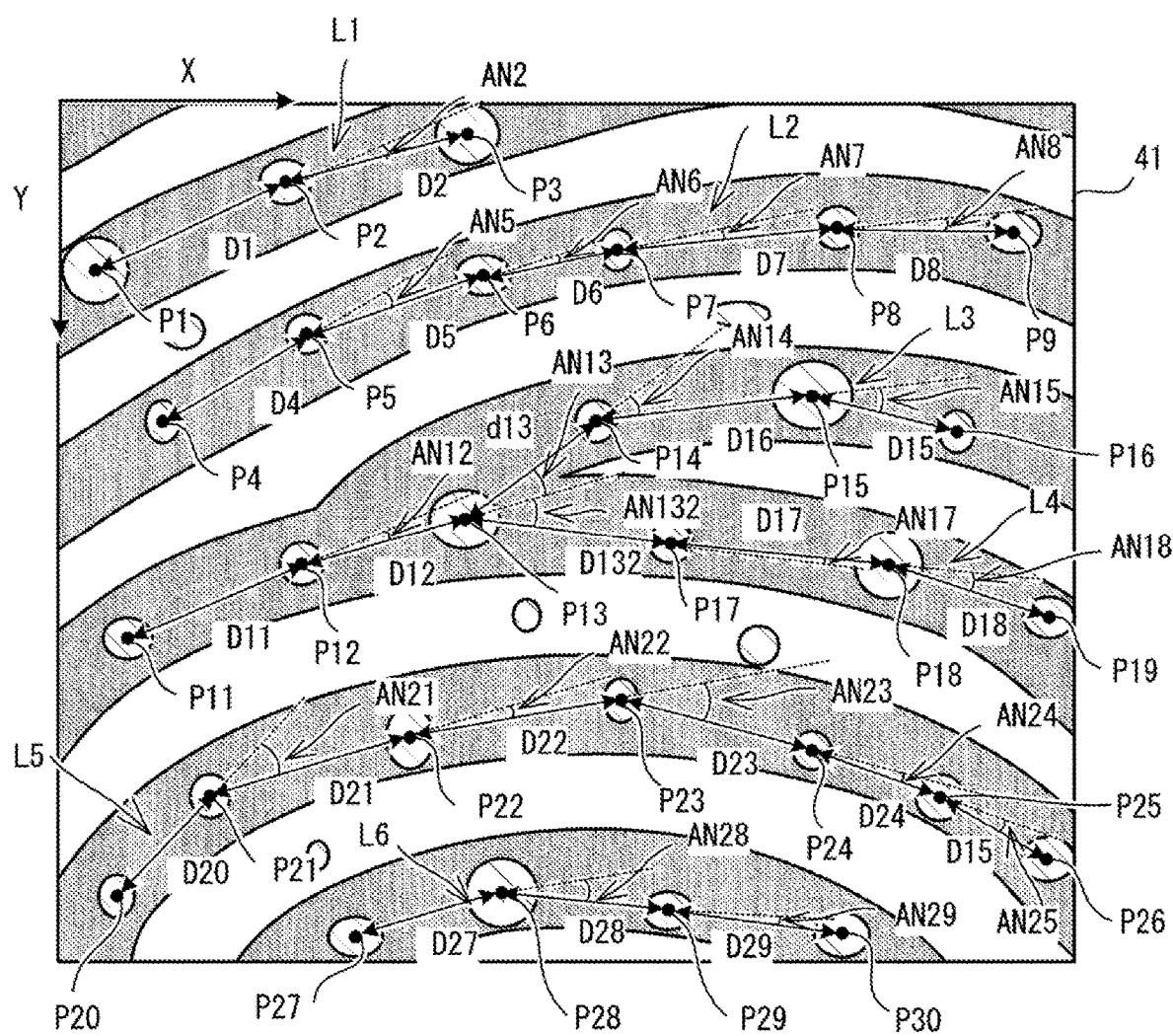
FIG. 15 is an explanatory diagram of the registration image.
Figure 16:
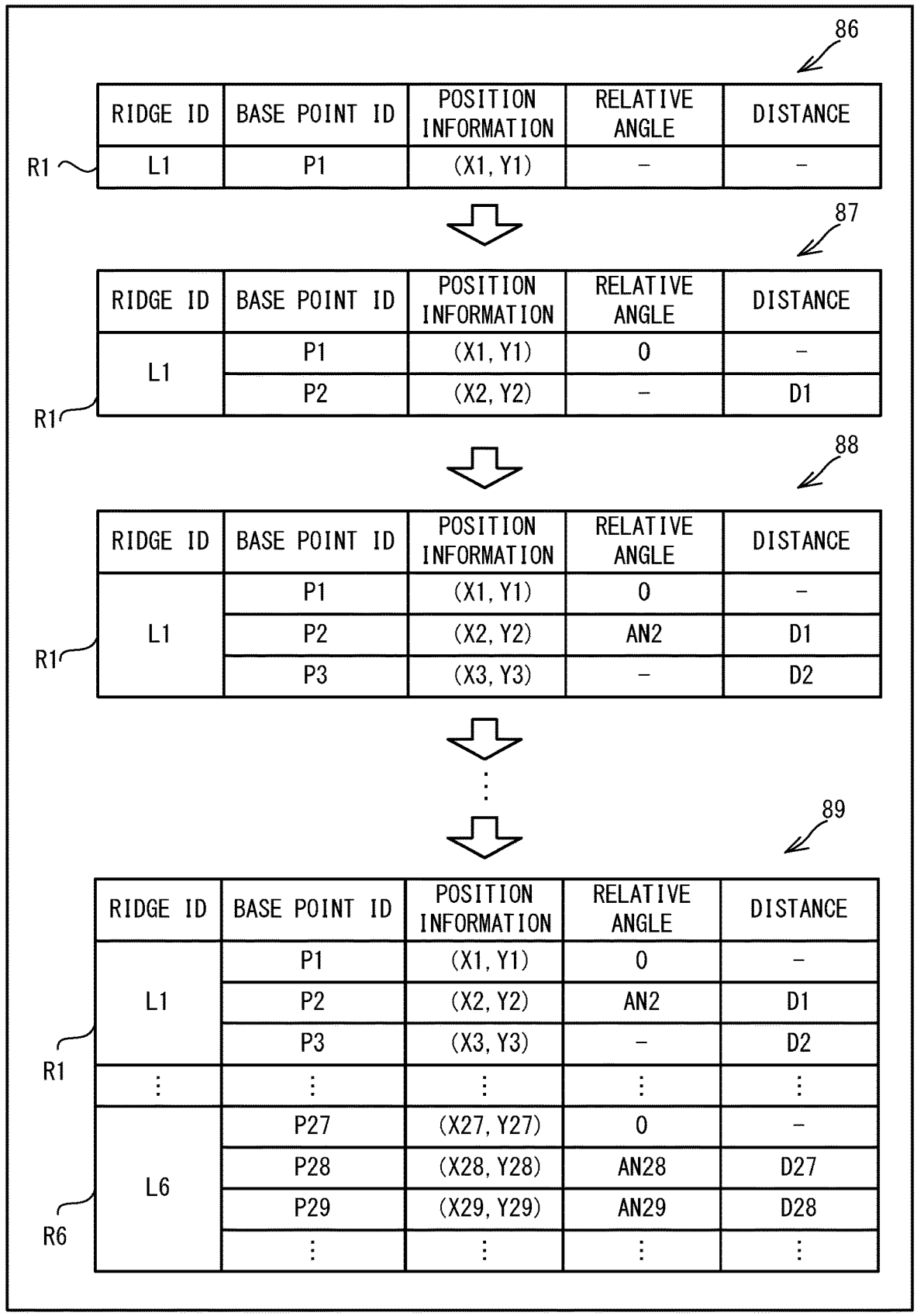
FIG. 16 is an explanatory diagram of a process that generates the ridge information.
Figure 18:
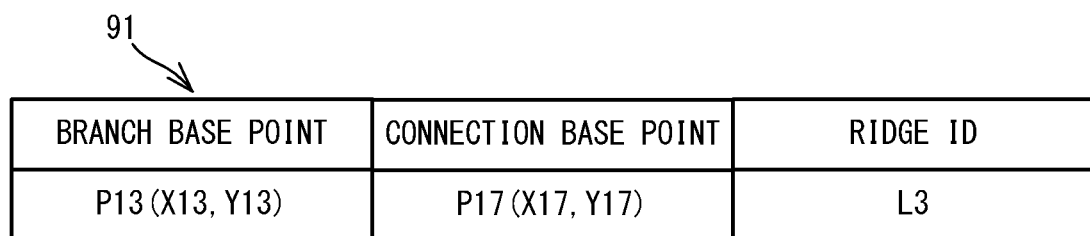
FIG. 18 is an explanatory diagram of a branch point list.

At S87, when a base point P13 shown in FIG. 15 is selected as a selected base point for ridge information R3, as shown in connection information B13 in FIG. 11, the number of the connection base points PB for the base point P13 is 3 and is thus greater than 2 (yes at S87). In this case, the CPU 1 adds the selected base point and the ridge information Ri to the branch point list (S88). As shown in FIG. 18, the CPU 1 stores the base point P13, and L3 that is the ridge ID of the ridge information R3 in a branch point list 91. The CPU 1 takes the selected base point as the target base point PT, and, from among the connection base points PB for the target base point PT, selects the base point that is not in the already selected list as the selected base point (S89). As shown in FIG. 18, from among the connection base points PB for the target base point PT, the CPU 1 stores the base point that has not already been selected as the selected base point in association with the ridge information Ri of the branch point list (S90). The CPU 1 refers to the connection information 85 shown in FIG. 11, and, from among the connection base points PB for the base point P13, adds the base point P17 that is not stored in the already selected list to the branch point list 91, in association with the base point P13. The CPU 1 returns the processing to S81. At S81, the CPU 1 determines whether the selected base point selected at S89 is stored as the base point of the other ridge information (S81).

Figure 19:
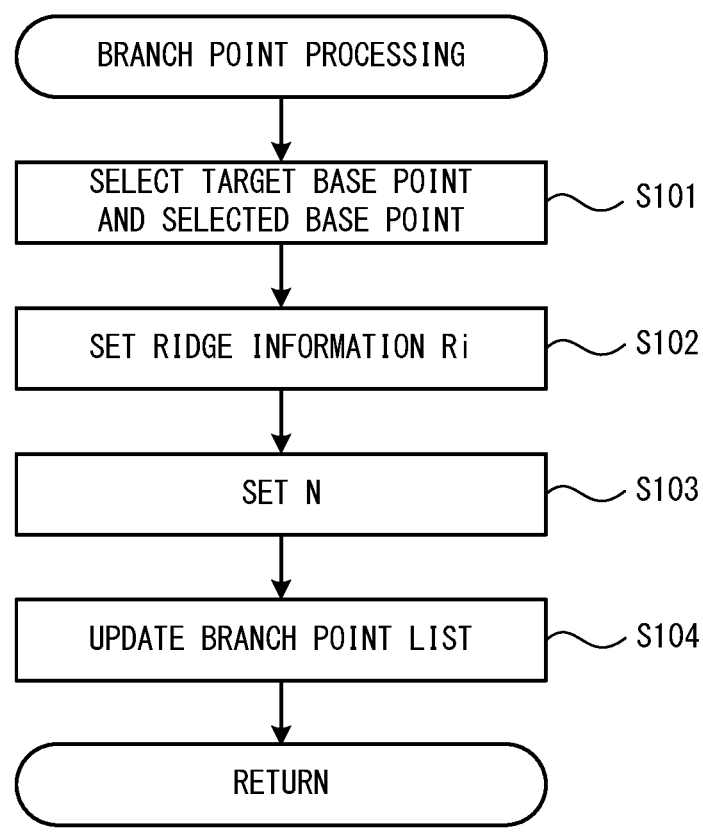
FIG. 19 is a flowchart of branch point processing that is performed in the ridge information generation processing shown in FIG. 14.

At S73 in relation to the ridge information R3, it is determined that the base point P13 is stored in the branch point list 91 shown in FIG. 18 (yes at S73). In this case, the CPU 1 performs the branch point processing (S74). As shown in FIG. 19, in the branch point processing, the CPU 1 selects the branch base point stored in the branch point list as the target base point PT, and selects the connection base point that is linked and stored with the branch base point as the selected base point (S101). The CPU 1 selects the base point P13 stored in the branch point list 91 as the target base point PT, and selects the base point P17 as the selected base point. The CPU 1 increments i by 1, and sets the new ridge information Ri (S102). The CPU 1 generates new ridge information R4. More specifically, the CPU 1 copies the ridge information from the start point of ridge information R (i−1) to the target base point PT into the ridge information Ri (S102). The CPU 1 copies the ridge information R3 from the base point P11 to the base point P13 into the ridge information R4. The CPU 1 sets the number of base points included in the ridge information Ri as the variable N (S103). The CPU 1 sets the variable N to 3 for the ridge information R4. The CPU 1 deletes the base point P13 that is the target base point PT from the branch point list (S104). The CPU 1 ends the branch point processing and returns the processing to the ridge information generation processing shown in FIG. 14. After the processing at S74, the CPU 1 returns the processing to S69. As described above, when the branch point is included in the continuous ridge, the CPU 1 defines the plurality of ridges having no bifurcations from the start point to the end point, including that branch point, such that the number of the bifurcating ridges corresponds to the number of bifurcations at the branch points. Then, the CPU 1 extracts the plurality of base points disposed on the same ridge for each of the defined plurality of ridges, and generates the ridge information.

At S75 shown in FIG. 14, the CPU 1 determines whether all of the base points have been selected as the target base point PT in the processing at S61 (S75). When at least one of the base points has not been selected as the target base point PT (no at S75), the CPU 1 returns the processing to S61. When all of the base points have been selected as the target base point PT (yes at S75), the CPU 1 ends the ridge information generation processing and returns the processing to the image analysis processing shown in FIG. 9. By the ridge information generation processing shown in FIG. 14, as shown in a list 89 in FIG. 16, the pieces of the ridge information R1 to ridge information R6 are generated corresponding to each of the ridges L1 to L6.

Figure 20:
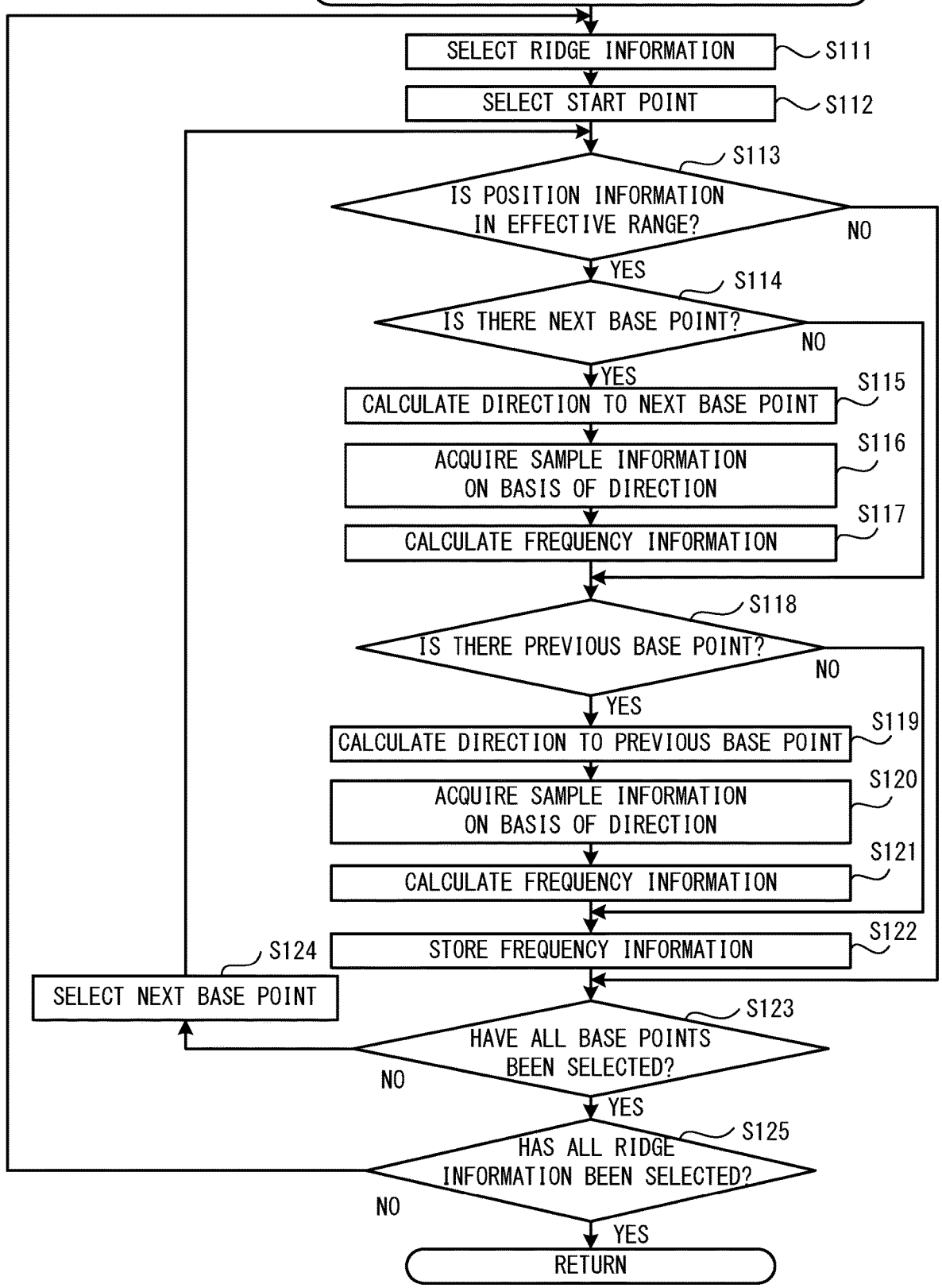
FIG. 20 is a flowchart of frequency information generation processing that is performed in the image analysis processing shown in FIG. 9.

The CPU 1 performs frequency information generation processing after the processing at S26 (S27). As shown in FIG. 20, in the frequency information generation processing, the CPU 1 selects one of the pieces of ridge information from among the plurality of pieces of ridge information generated by the processing at S26 (S111). For example, the CPU 1 selects the ridge information R1 from the list 89 shown in FIG. 16. From among the base points P1 to P3 included in the ridge information R1 selected at S111, the CPU 1 selects, as a start point, the base point P1 that is first in the arrangement order (S112). The CPU 1 determines whether or not the position information of the selected base point P1 is inside an effective range of the image acquired at S21 (S113). The effective range is a region in which the samples can be acquired and a region in which the biometric information can be acquired. There is a case in which the image representing the skin information is not acquired over the whole of an image capturable range of the skin information acquisition device 8, and, in the image capturable range, there is a region that is not touched by the finger of the user, for example. The skin information does not appear in the image of this type of region. For example, since the skin information does not appear in a white image region corresponding to the region that is not touched by the user's finger, the CPU 1 of the present embodiment does not extract the samples of points that are not in the effective range. Thus, for example, when a peak value of a power spectrum of a two-dimensional Fourier transform of color information of a specified range centering on the selected base point is equal to or greater than a constant value, the CPU 1 determines that the position information of the selected base point is in the effective range. In another example, when the sum of absolute values of values obtained by applying a differential filter to the color information of a predetermined range including the selected base point, or the sum of squares is equal to or greater than a constant value, the CPU 1 determines that the position information of the selected base point is in the effective range.

When the position information of the selected base point is not in the effective range (no at S113), the CPU 1 performs processing at S123 to be described later. When the position information of the selected base point is in the effective range (yes at S113), the CPU 1 refers to the ridge information R1 selected at S111, and determines whether, in the arrangement order, there is the base point after the selected base point P1 (S114). When there is no base point after the selected base point (no at S114), the CPU 1 performs processing at S118 to be described later. In the ridge information R1, the base point P2 is included that is after the base point P1 in the arrangement order (yes at S114). In this case, the CPU 1 calculates a direction U1 of a vector from the selected base point P1 toward the base point P2 that is next in the arrangement order (S115). The CPU 1 acquires the color information indicating the color around the selected base point P1, on the basis of the direction U1 calculated at S115 (S116).

Figure 21:
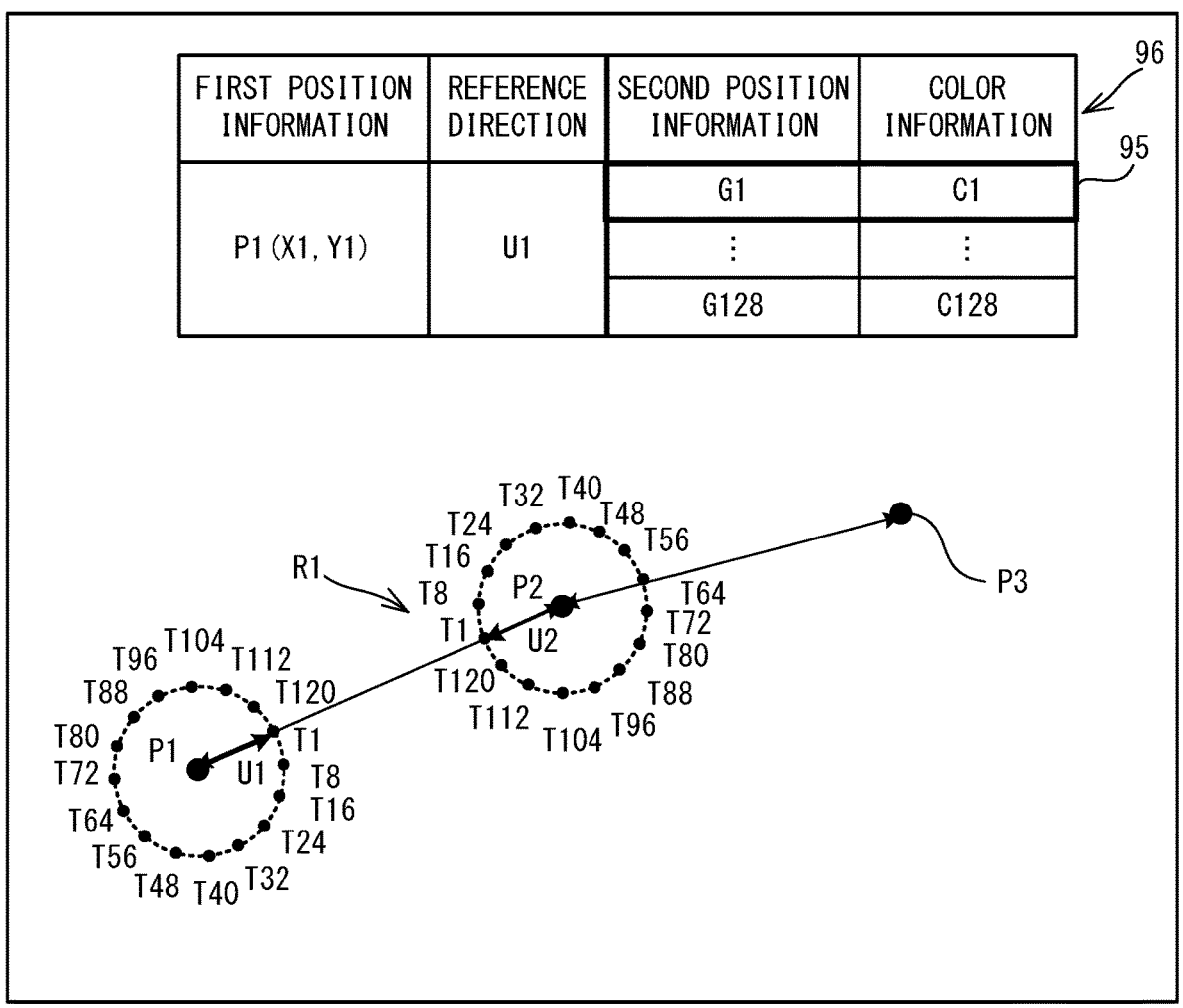
FIG. 21 is an explanatory diagram of a process to acquire samples.
Figure 22:
FIG. 22 is an explanatory diagram of the ridge information.

More specifically, the CPU 1 determines a point for which a distance from the selected base point P1 is a predetermined value, and which is in the direction U1 calculated at S115 with respect to the base point P1, as a starting point T1. The CPU 1 acquires a predetermined number of reference points in accordance with predetermined conditions. As shown in FIG. 21, for example, in accordance with the predetermined conditions, taking the starting point T1 as a reference, the CPU 1 sets 128 reference points Tm (m is an integer from 1 to 128) in order at equal intervals in the clockwise direction, on the circumference of a circle having a predetermined radius and centering on the selected base point P1. When the reference points Tm have coordinates in units of sub-pixels, the color information is acquired using known bilinear interpolation or bicubic interpolation. The CPU 1 acquires samples 95 that associate color information Cm corresponding to the reference points Tm with second position information. The samples 95 are associated with the first position information that indicates the position of the base point P1 on the image. It is sufficient that the first position information is information that defines the position of the base point P1 on the image. For example, the first position information may be absolute coordinates (for example, coordinates of the image coordinate system), relative coordinates, an acquisition order, or the like. The first position information of the present embodiment is represented by the coordinates of the image coordinate system. It is sufficient that the second position information is information that defines the positions of the reference points Tm in relation to the base point P1. For example, the second position information may be absolute coordinates (for example, coordinates of the image coordinate system), relative coordinates, an angle in relation to a reference, or the like. When the order of acquisition of the reference points is determined with respect to a point used as the reference (the starting point, for example), the second position information may be the order of acquisition of the reference points. In the present embodiment, the order of acquisition of the reference points Tm is acquired as the second position information. The order of acquisition of the reference points T1 to T128 is 1 to 128, respectively. The plurality of samples 95 are samples acquired for each of the plurality of reference points Tm whose positions are different from each other. The CPU 1 uses, as sample data 96, information that associates the plurality of samples 95 acquired for the single starting point T1 with the first position information.

The CPU 1 calculates frequency components of changes in the color information with respect to the second position information for the plurality of samples 95 (the sample data 96) acquired at S116, and generates frequency information (S117). The frequency components are, for example, a known LPC spectrum, an LPC cepstrum, a group delay spectrum, and the like. The frequency components are, for example, the group delay spectrum (GDS), and are defined as the frequency derivative of a phase spectrum in a power transfer function. The CPU 1 uses a linear prediction coefficient, which is calculated using the Yule-Walker method without multiplying a window function, to calculate the frequency information. Specifically, the CPU 1 uses the linear prediction coefficient calculated using the Yule-Walker method without multiplying the window function, and calculates the GDS by obtaining the phase derivative of a power spectrum obtained by performing a high-speed Fourier transform on a weighted LPC coefficient. The CPU 1 uses the calculated GDS as the frequency information.

The CPU 1 refers to the ridge information R1 selected at S111, and determines whether there is the base point that is before the selected base point P1 in the arrangement order (S118). There is no base point that is before the selected base point P1 in the arrangement order (no at S118). In this case, the CPU 1 performs processing at S122 to be described later. When there is the base point that is before the base point in the arrangement order (yes at S118), the CPU 1 calculates a direction U of a vector from a selected base point Pk toward the base point that is before the base point Pk in the arrangement order (S119). When the selected base point Pk is the base point P2 (yes at S118), using a similar procedure to the processing at S116, the CPU 1 acquires the color information indicating the color around the selected base point P2, on the basis of a direction U2 from the base point P2 toward the base point P1 (S120). Using a similar procedure to the processing at S117, the CPU 1 calculates the frequency components of the changes in the color information with respect to the second position information for the plurality of samples 95 (the sample data 96) acquired at S120 (S121). The CPU 1 stores the frequency information generated at at least one of S117 and S121 in association with the selected base point (S122). The CPU 1 determines whether the base points included in the ridge information selected at S111 have been selected by the processing at S112 or by processing at S124 (S123). When there is the base point that has not been selected (no at S123), the CPU 1 selects the next base point in the arrangement order (S124), and returns the processing to S113.

When all of the base points included in the ridge information selected at S111 have been selected (yes at S123), the CPU 1 determines whether all of the ridge information generated by the processing at S26 has been selected at S111 (S125). When there is the unselected ridge information (no at S125), the CPU 1 returns the processing to S111. When all of the ridge information has been selected by the processing at S111 (yes at S125), the CPU 1 ends the frequency information generation processing and returns the processing to the image analysis processing shown in FIG. 9. In the image analysis processing shown in FIG. 9, after S27, the CPU 1 associates the ridge information generated at S26 with the frequency information generated at S27, as shown in a list 98 in FIG. 22, and stores the associated information as the collation information used in the authentication of the skin information (S28). The CPU 1 ends the image analysis processing and returns the processing to the skin information processing shown in FIG. 8. After the processing at S11, the CPU 1 determines whether the collation information including the ridge information has been acquired at S11 (S12). When the collation information has not been acquired (no at S12), the CPU 1 performs error notification (S16). For example, the CPU 1 displays an error message on the display portion 6. When the collation information has been acquired (yes at S12), it is determined whether to register the collation information acquired at S11 in the DB 28 (refer to FIG. 2) as the collation information for registration (S13). The information indicating whether to perform the registration is included in the start command, for example. In the specific example, it is determined that the registration is to be performed (yes at S13), and the CPU 1 stores the collation information acquired at S11 in the DB 28 of the flash memory 4 (S14). When the collation information is not to be registered in the DB 28 (no at S13), the CPU 1 performs collation processing to set the collation information acquired at S11 that is a collation target as the collation information for collation (S15). After one of S14, S15, or S16, the CPU 1 ends the skin information processing.

2. Processing at Collation

Figure 23:
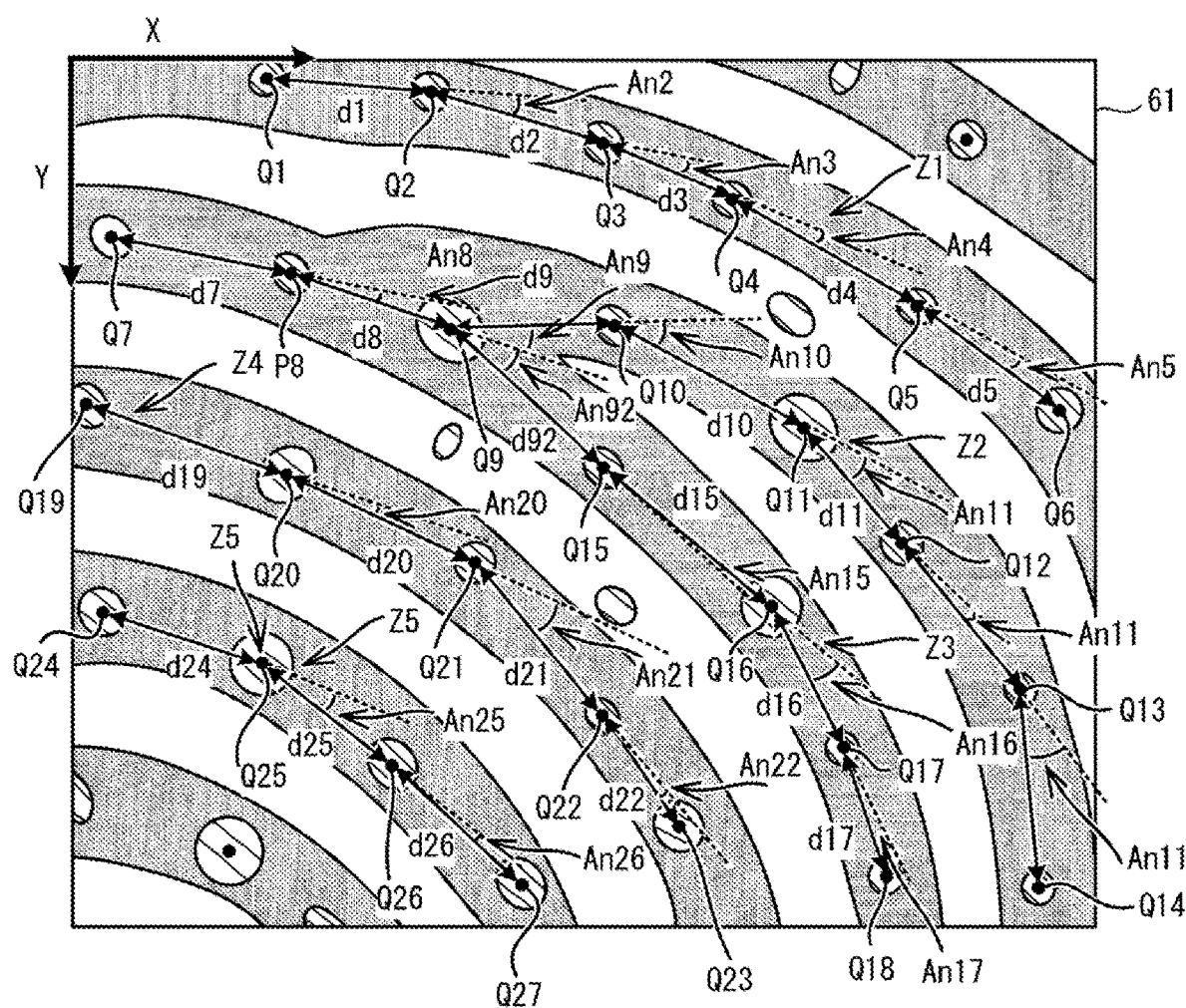
FIG. 23 is an explanatory diagram of a collation image.

The skin information processing at the time of collation will be explained taking a case as an example in which the pieces of ridge information R1 to R6 extracted from the image 41 shown in FIG. 15 is used as the collation information for registration, and an image 61 shown in FIG. 23 is acquired as a collation image that is the collation target. In the skin information processing at the time of collation, S11 is performed similarly to the skin information processing at the time of registration. For example, base points Q1 to Q27 shown in FIG. 23 are determined as the base points at S23 shown in FIG. 9. On the basis of the base points Q1 to Q27 shown in FIG. 23, the pieces of ridge information V1 to V5 shown in a list 92 in FIG. 24 are generated for ridges Z1 to Z5. In the following explanation, the ridge information for collation is denoted by ridge information Vn (where n is an integer), and the ridge information for registration is denoted by ridge information Rm (where m is an integer) and the two are thus distinguished from each other. The base point for collation is denoted by a base point Qj (where j is an integer) and the base point for registration is denoted by a base point Pk (where k is an integer), and the two are thus distinguished from each other.

At S12 shown in FIG. 8, it is determined that the collation information has been acquired (yes at S12), and it is determined on the basis of the start command that registration is not to be performed (no at S13). The CPU 1 performs the collation processing (S15). In the collation processing, the CPU 1 determines a correspondence between the ridge information Rm and the ridge information Vn. The CPU 1 calculates a similarity degree W for the determined correspondence, and performs the skin authentication.

Figure 25:
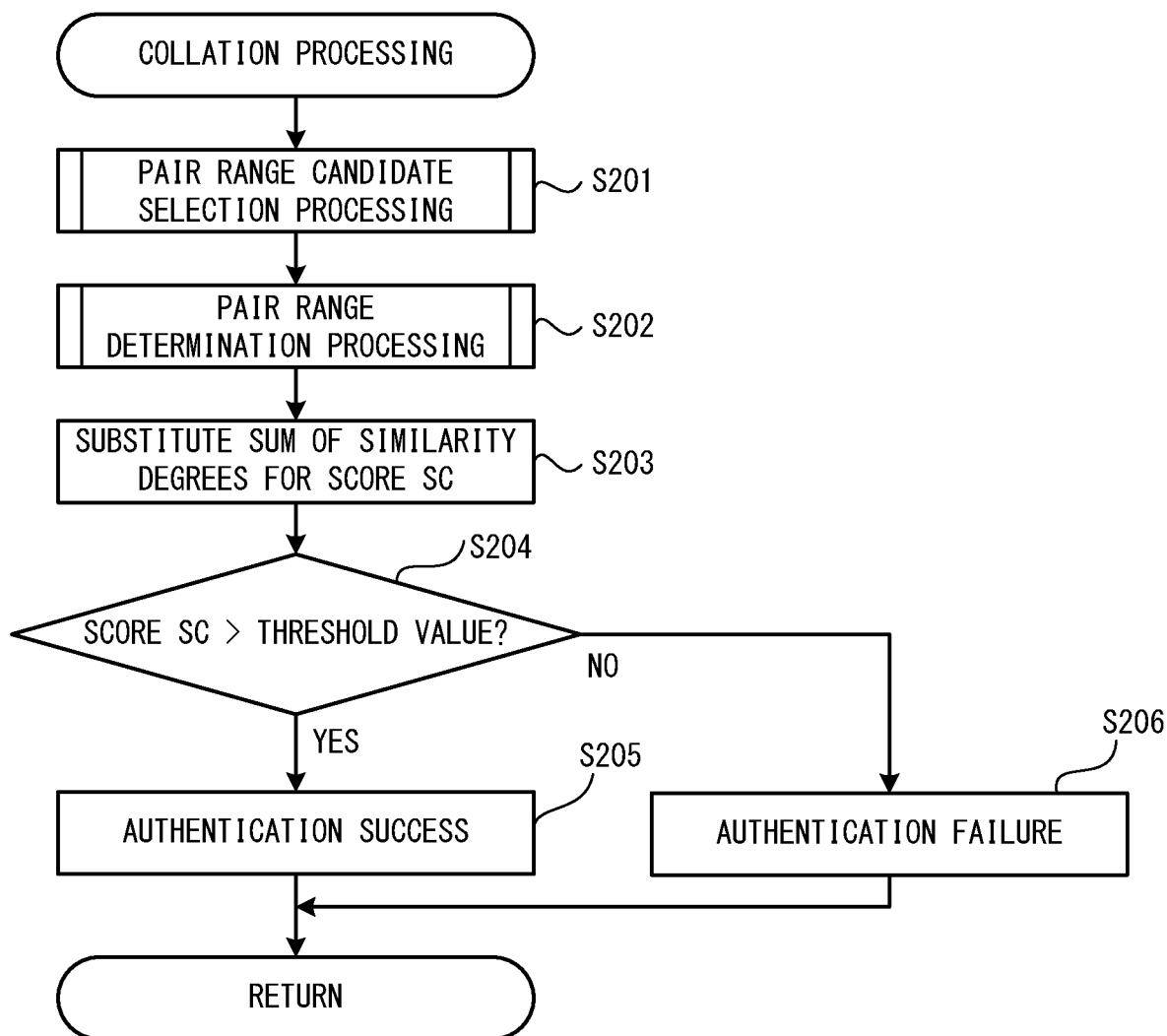
FIG. 25 is a flowchart of collation processing that is performed in the skin information processing shown in FIG. 8.
Figure 26:
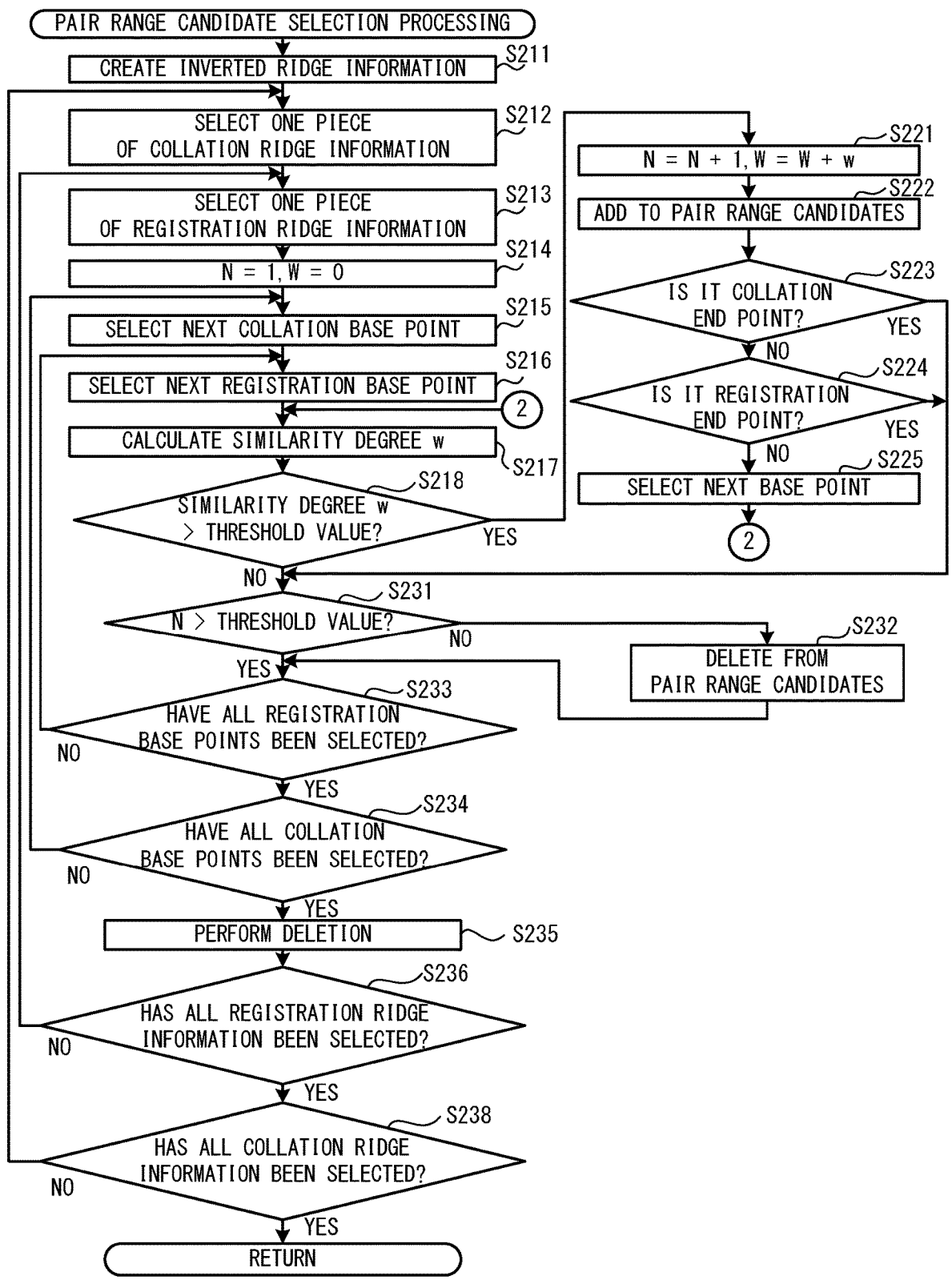
FIG. 26 is a flowchart of pair range candidate selection processing that is performed in the collation processing shown in FIG. 25.

In the collation processing, as shown in FIG. 25, the CPU 1 performs pair range candidate selection processing (S201). The pair range candidate selection processing is processing to select candidates for a pair range. The pair range is a range over which, among a plurality of combinations of the collation ridge information Vn and the registration ridge information Rm, a difference between the selected collation ridge information and the selected registration ridge information is equal to or lower than a threshold value for equal to or greater than a predetermined number of the continuous base points. In the pair range candidate selection processing, the CPU 1 selects candidates for a positional correspondence, which is a correspondence between the base point of the collation ridge information used in the skin authentication, and the base point of the registration ridge information stored in the storage portion. In the pair range candidate selection processing, as shown in FIG. 26, with respect to all of the ridge information V1 to V5 generated on the basis of the collation image 61, the CPU 1 generates pieces of ridge information v1 to v5 in which the start points and the end points have been inverted (S211). For each of all the pieces of ridge information V1 to V5 generated on the basis of the collation image 61 and shown in the list 92 in FIG. 24, the CPU 1 inverts the arrangement order of the base points and generates the pieces of ridge information v1 to v5. In the pieces of ridge information v1 to v5, for the position information and the distances, the values corresponding to the base points are used as they are. The relative angle is a value obtained by multiplying a relative angle AN by −1.

The CPU 1 selects one of the pieces of ridge information from the plurality of pieces of ridge information that include the pieces of ridge information V1 to V5 generated on the basis of the collation image 61 and the pieces of ridge information v1 to v5 generated at S211 (S212). For example, the CPU 1 selects the ridge information V1 for the ridge Z1. The CPU 1 selects one of the pieces of ridge information from the pieces of ridge information R1 to R6 generated on the basis of the registration image 41 (S213). The CPU 1 selects the ridge information R1 for the ridge L1.

The CPU 1 sets the variable N to 1, and sets the similarity degree W to zero (S214). The variable N indicates a number of pairs of the base points included in the pair range candidates. Among the combinations of the base point Pk included in the ridge information Rm and the base point Qj included in the ridge information Vn, the pair refers to a combination for which a similarity degree w calculated at S217 (to be described later) is equal to or lower than a threshold value. The CPU 1 selects the one base point that is next in the arrangement order from among the base points Qj included in the ridge information Vn (S215). For example, the CPU 1 selects the base point Q1 that is first in the arrangement order of the ridge information V1 shown in FIG. 24. The CPU 1 selects the one base point that is next in the arrangement order from among the base points Pk included in the ridge information Rm (S216). For example, the CPU 1 selects the base point P1 that is first in the arrangement order of the ridge information R1 shown in FIG. 16.

The CPU 1 compares the base point Qj selected at S215 and the base point Pk selected at S216 and calculates the similarity degree w (S217). The CPU 1 compares the relative angles and the distances of the base point Qj and the base point Pk, applies a comparison result to a predetermined array, and calculates the similarity degree w. Compared to when the similarity degree w is smaller, the larger the similarity degree w, the greater it is estimated that the base point Qj and the base point Pk are similar points. When at least one of the base point Qj selected at S215 and the base point Pk selected at S216 is the start point (the first point in the arrangement order) or the end point (the last point in the arrangement order) of a line segment group that is represented by the corresponding ridge information, the CPU 1 sets a constant as the similarity degree w. The constant is larger than the threshold value at S218 to be described later. Both the base point Q1 and the base point P1 are the start point of the line segment group represented by the ridge information, and the constant is set as the similarity degree w.

The CPU 1 determines whether the similarity degree w calculated at S217 is larger than the threshold value (S218). The similarity degree w of the specific example is larger than the threshold value (yes at S218). In this case, the CPU 1 increments the variable N by 1, adds the similarity degree w calculated in the processing at S217 to the similarity degree W, and updates the similarity degree W (S221). As shown in a list 71 in FIG. 28, the CPU 1 adds the base point Q1 selected at S215 and the base point P1 selected at S216 to the pair range candidates relating to the ridge information V1 selected at S212 and the ridge information R1 selected at S213 (S222). The CPU 1 determines whether the base point Q1 selected at S215 is the end point of the ridge information V1 selected at S212 (S223). When the base point Qj selected at S215 is the end point of the ridge information Vn selected at S212 (yes at S223), the CPU 1 performs processing at S231 to be described later. The base point Q1 is not the end point of the ridge information V1 (no at S223). In this case, the CPU 1 determines whether the base point P1 selected at S216 is the end point of the ridge information R1 selected at S213 (S224). When the base point Pk selected at S216 is the end point of the ridge information Rm selected at S213 (yes at S224), the CPU 1 performs the processing at S231 to be described later. The base point P1 is not the end point of the ridge information R1 (no at S224). In this case, the CPU 1 selects the one base point that is next in the arrangement order, for each of the ridge information V1 selected at S212 and the ridge information R1 selected at S213 (S225). The CPU 1 selects the base point Q2 as the base point that is next in the arrangement order of the ridge information V1, after the base point Q1. The CPU 1 selects the base point P2 as the base point that is next in the arrangement order of the ridge information R1, after the base point P1.

The CPU 1 returns the processing to S217, and calculates the similarity degree w between the base point Q2 and the base point P2 (S217). It is determined that the similarity degree w between the base point Q2 and the base point P2 is not larger than the threshold value (no at S218), and the CPU 1 determines whether N is larger than a threshold value or not (S231). The processing at S231 is processing to extract, as the pair range candidates, the pairs of the line segment group for which the number of pairs is larger than a threshold value. The threshold value is 3, for example. In the specific example, N is 2 (no at S231), and, of the pairs relating to the ridge information V1 stored at S222 and selected at S212 and the ridge information R1 selected at S213, the CPU 1 deletes a pair for which the start point is the base point Q1 selected at S215 and the base point P1 selected at S216, from the pair range candidates (S232).

When the variable N is larger than the threshold value (yes at S231), or after S232, the CPU 1 determines whether all of the base points of the ridge information R1 selected at S213 have been selected by the processing at S216 (S233). When the base point Pk selected at S216 is the last base point in the arrangement order of the plurality of base points included in the ridge information R1 selected at S213, the CPU 1 determines that all the base points of the ridge information R1 selected at S213 have been selected by the processing at S216 (yes at S233). The base point P1 selected by the processing at S216 is not the last base point in the ridge information R1 (no at S233). In this case, the CPU 1 selects the base point P2 that is the next base point after the base point P1 in the arrangement order, from the ridge information R1 selected by the processing at S213. When all of the base points of the ridge information R1 selected at S213 have been selected by the processing at S216 (yes at S233), the CPU 1 determines whether all the base points of the ridge information V1 selected at S212 have been selected by the processing at S215 (S234). When the base point Qj selected at S215 is the last base point in the arrangement order of the plurality of base points included in the ridge information V1 selected at S212, the CPU 1 determines that all of the base points of the ridge information V1 selected at S212 have been selected by the processing at S215 (yes at S234). When the base point Q selected by the processing at S215 is the base point Q1, this is not the last base point in the collation ridge information selected at S212 (no at S234).

In this case, the CPU 1 returns the processing to S215, and, of the ridge information Vn selected at S212, selects the next base point in the arrangement order after the base point Qj selected in the previous processing at S215 (S215). At S216 after the processing at S215, of the registration ridge information selected at S213, the first base point in the arrangement order is selected. When all the base points of the ridge information Vn selected at S212 have been selected by the processing at S215 (yes at S234), of the pair range candidates relating to the ridge information Vn selected at S212 and the ridge information Rm selected at S213, the CPU 1 leaves only the pair range candidates for which the similarity degree W added up at S221 is the largest, and deletes the other pair range candidates (S235). The CPU 1 determines whether or not, in relation to the ridge information Vn selected at S212, all of the pieces of ridge information Rm have been selected by the processing at S213 (S236). When, in relation to the ridge information Vn selected at S212, the ridge information Rm is remaining that has not been selected at S213 (no at S236), the CPU 1 returns the processing to S213, and selects the ridge information Rm that has not yet been selected (S213). When the ridge information V1 is selected at S212, the ridge information R2 is selected at S213, the base point Q1 is selected at S215, and the base point P4 is selected at S215, by the processing at S222 that is repeatedly performed, six pairs of the base points are stored in a list 72 shown in FIG. 28, as the pair range candidates. At S223, the base point Q6 is determined to be the end point (yes at S223), and the variable N is 7, and is determined to be larger than the threshold value (yes at S231). By the same processing, when the ridge information V1 is selected at S212, the ridge information R2 is selected at S213, the base point Q2 is selected at S215, and the base point P5 is selected at S215, by the processing at S222 that is repeatedly performed, five pairs of the base points are stored in a list 73 shown in FIG. 28, as the pair range candidates. When the ridge information V1 is selected at S212 and the ridge information R2 is selected at S213, at S235, as the pair range candidate relating to the ridge information V1 and the ridge information R2, only the base points of the six pairs shown in the list 72 for which the similarity degree W is largest are left and the other pair range candidates are deleted.

When all the pieces of ridge information Rm in relation to the ridge information Vn selected at S212 have been selected at S213 (yes at S236), the CPU 1 determines whether or not all the pieces of ridge information Vn have been selected in the processing at S212 (S238). When there is the ridge information Vn that has not been selected at S212 (no at S238), the CPU 1 returns the processing to S212, and selects the ridge information Vn that has not yet been selected (S212). When all the pieces of ridge information Vn have been selected at S212 (yes at S238), the CPU 1 ends the pair range candidate selection processing and returns the processing to the collation processing shown in FIG. 25. As a result of the pair range candidate selection processing shown in FIG. 26, the pair range candidates shown in FIG. 29 are selected. As shown in FIG. 29, with respect to the ridge information V1 for the ridge Z1, and the ridge information R2 for the ridge L2, the six pairs of the base points are stored as the pair range candidates. With respect to the ridge information V2 for the ridge Z2, and the ridge information R3 for the ridge L3, the six pairs of the base points are stored as the pair range candidates. With respect to the ridge information V3 for the ridge Z3, and the ridge information R4 for the ridge L4, the six pairs of the base points are stored as the pair range candidates. With respect to the ridge information V4 for the ridge Z4, and the ridge information R5 for the ridge L5, the five pairs of base points are stored as the pair range candidates. With respect to the ridge information V5 for the ridge Z5, and the ridge information R6 for the ridge L6, the four pairs of base points are stored as the pair range candidates. With respect to the ridge information V5 and the ridge information R5 for the ridge L5, the four pairs of base points are stored as the pair range candidates. There is a case in which, as with the ridge information V5, a specified range of the one piece of ridge information Vn and a specified range of a plurality of the pieces of ridge information Rm are used as the candidates for the pair range. By the processing at S201, the determined plurality of sets of registration line segment information and collation line segment information are acquired as the combinations used in the calculation of the similarity degree.

Figure 30:
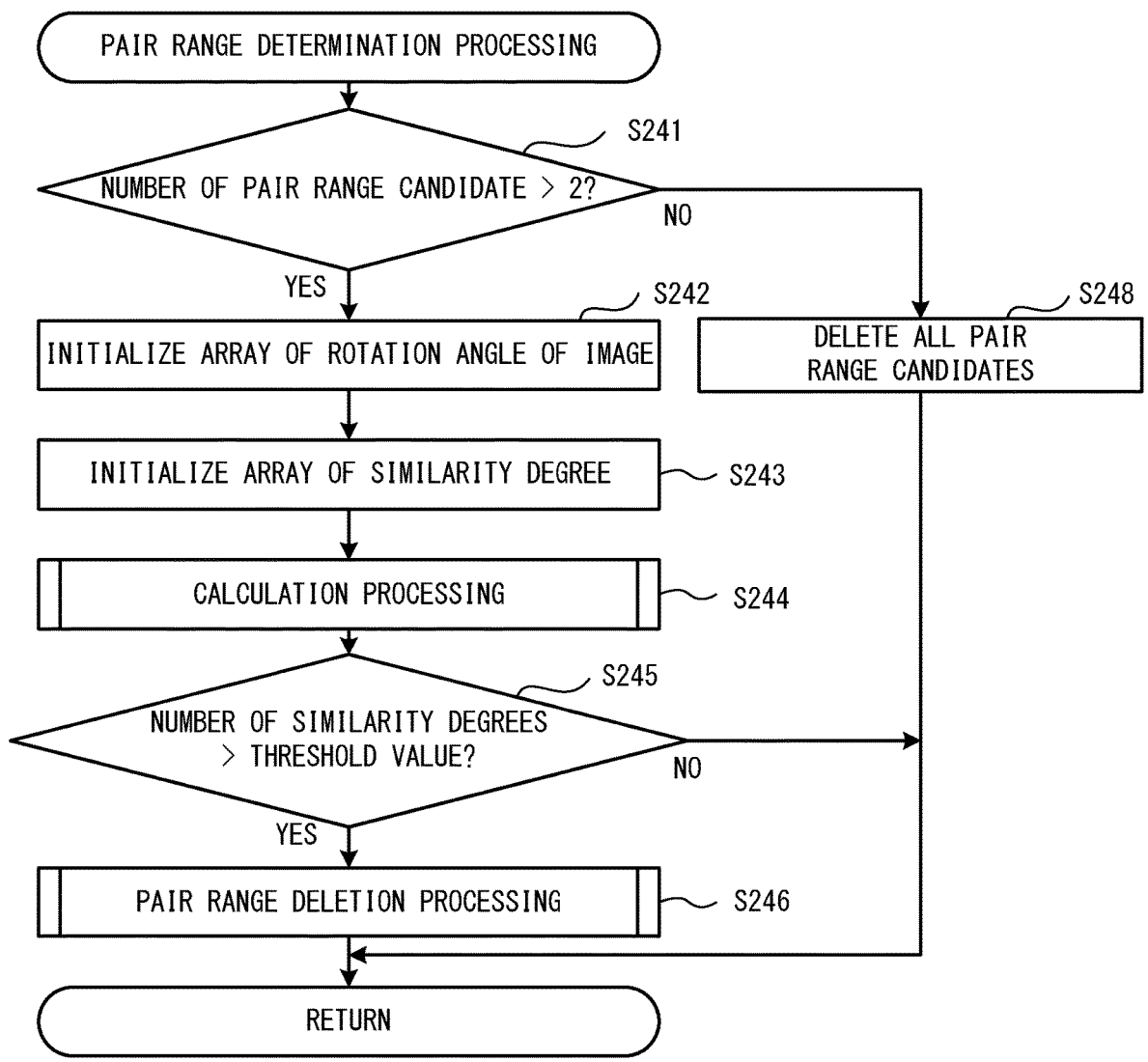
FIG. 30 is flowchart of pair range determination processing that is performed in the collation processing shown in FIG. 25.

After the processing at S201 shown in FIG. 25, the CPU 1 performs pair range determination processing (S202). In the pair range determination processing, the CPU 1 determines the pair range on the basis of the pair range candidates selected at S201, and calculates a similarity degree WR between the collation ridge information and the registration ridge information, on the basis of the determined positional correspondence. As shown in FIG. 30, in the pair range determination processing, the CPU 1 determines whether or not the number of pair range candidates created in the processing at S201 is greater than 2 (S241). When the number of pair range candidates is not larger than 2 (no at S241), the CPU 1 deletes all the pair range candidates (S248), ends the pair range determination processing, and returns the processing to the collation processing shown in FIG. 25. As shown in a list 74 in FIG. 29, in the specific example, the six pairs of the pair range candidates are created (yes at S241). In this case, the CPU 1 initializes an array of a rotation angle of the image (S242). The CPU 1 initializes an array of the similarity degree (S243). The CPU 1 performs calculation processing (S244). In the calculation processing, the CPU 1 selects the two sets of the collation ridge information Vn and the registration ridge information Rm for which the pair range candidate is identified, and identifies, for each of the selected two sets of collation ridge information and registration ridge information, both of ends when a plurality of base points inside the pair range candidate are connected using a line segment in accordance with the arrangement order. The CPU 1 compares relative positions of both ends corresponding to each of the two pieces of collation ridge information and both ends corresponding to each of the two pieces of registration ridge information, and calculates the similarity degree WR.

Figure 31:
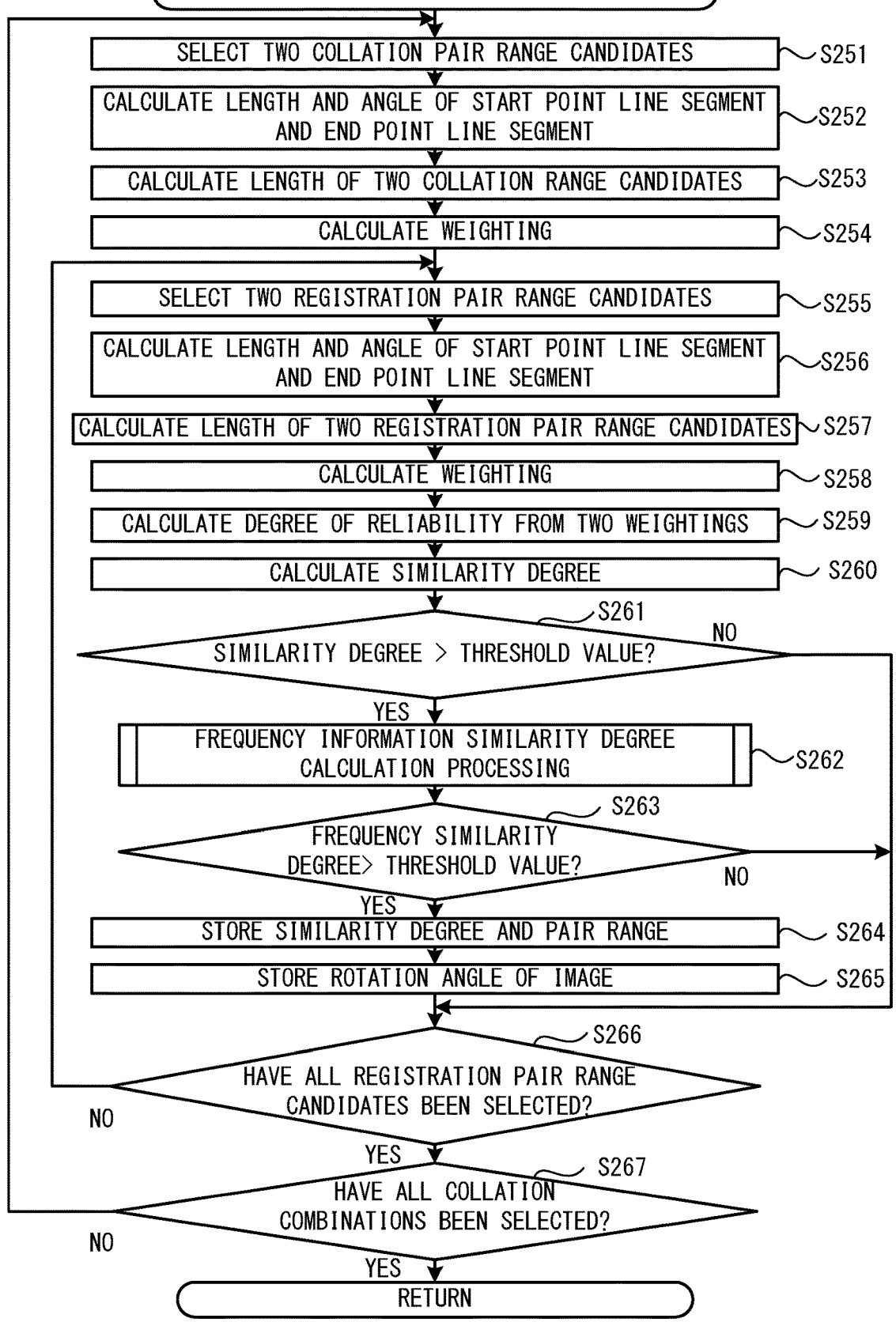
FIG. 31 is a flowchart of calculation processing that is performed in the pair range determination processing shown in FIG. 30.

As shown in FIG. 31, in the calculation processing, from among the pair range candidates stored in the list 74 in FIG. 29 by the pair range candidate selection processing at S201, the CPU 1 selects two sets of the collation pair range candidates (S251). The CPU 1 selects the pair range candidates that include the six pairs of the base points Q1 to Q6 in the ridge information V1 (the ridge Z1), and the pair range candidates that include the five pairs of the base points in the ridge information V4 (the ridge Z4). For the two sets of collation ridge information Vn selected by the processing at S251, the CPU 1 identifies both the ends when the plurality of base points inside the pair range candidate are connected in accordance with the arrangement order, and calculates a length and angle of a start point line segment and an end point line segment when one of the ends is the start point and the other end is the end point (S252). More specifically, of the base points Q1 to Q6 included in the pair range candidates of the ridge information V1 for the ridge Z1 shown in the image 67 in FIG. 27 and in the list 74 in FIG. 29, the CPU 1 takes the base point Q1 as the start point and takes the base point Q6 as the end point. Of the base points Q19 to Q23 included in the pair range candidates of the ridge information V4 for the ridge Z4, the CPU 1 takes the base point Q19 as the start point and takes the base point Q23 as the end point. For a start point line segment LS1 connecting the base point Q1 and the base point Q19, the CPU 1 calculates a length thereof, and an angle AS1 of the start point line segment LS1 with respect to a line segment parallel to the X axis. For an end point line segment LS2 that connects the base point Q6 and the base point Q23, the CPU 1 calculates a length thereof, and an angle AS2 of the end point line segment LS2 with respect to a line segment parallel to the X axis.

For the two sets of collation ridge information Vn selected at S251, the CPU 1 calculates the length of a line segment obtained when the plurality of base points inside the pair range candidate are connected in accordance with the arrangement order (S253). The length of a line segment obtained when the base points Q1 to Q6 are connected in order is the sum of distances d1 to d5. The length of a line segment obtained when the base points Q19 to Q23 are connected in order is the sum of distances d19 to d22. The CPU 1 calculates a weighting, on the basis of the lengths of the start point line segment LS1 and the end point line segment LS2 calculated at S252, and the length of the line segment inside the pair range candidate calculated at S253 (S254). For example, the CPU 1 calculates, as the weighting, a value obtained by dividing the length calculated at S253 by the sum of the length of the start point line segment LS1 and the length of the end point line segment LS2 obtained in the processing at S252. When the calculated weighting is equal to or greater than a predetermined value, the CPU 1 may substitute the predetermined value for the weighting.

The CPU 1 refers to the list 74 shown in FIG. 29 and selects two sets of the registration pair range candidates corresponding to the two sets of collation pair range candidates selected at S251 (S255). By the processing at S251 and the processing at S255, the CPU 1 selects the two sets of registration ridge information and collation ridge information. Corresponding to the pair range candidate that includes the six pairs of the base points Q1 to Q6 in the ridge information V1 (the ridge Z1), the CPU 1 selects the pair range candidate that includes the six pairs of the base points P4 to P9 in the ridge information R2 (the ridge L2). Corresponding to the pair range candidate that includes the five pairs of the base points in the ridge information V4 (the ridge Z4), the CPU 1 selects the pair range candidate that includes the five pairs of the base points P21 to P25 in the ridge information R5 (the ridge L5). Similarly to S252, for the two sets of the registration ridge information Rm selected by the processing at S256, the CPU 1 identifies both the ends when the plurality of base points inside the pair range are connected in accordance with the arrangement order, and calculates a length and angle of the start point line segment and the end point line segment when one of the ends is taken as the start point and the other is taken as the end point (S256). Of the base points P4 to P9 included in the pair range candidates of the ridge information R2 for the ridge L2, the base point P4 is the start point and the base point P9 is the end point. Of the base points P21 to P25 included in the pair range candidates of the ridge information R5 for the ridge L5, the CPU 1 takes the base point P21 as the start point and takes the base point P25 as the end point. For a start point line segment LT1 connecting the base point P4 and the base point P21, the CPU 1 calculates a length thereof, and an angle AT1 of the start point line segment LT1 with respect to a line segment parallel to the X axis. For an end point line segment LT2 connecting the base point P9 and the base point P25, the CPU 1 calculates a length thereof, and an angle AT2 of the end point line segment LT2 with respect to a line segment parallel to the X axis. Similarly to S253, for the two sets of registration ridge information Rm selected at S255, the CPU 1 calculates the length of a line segment obtained when the plurality of base points inside the pair range candidate are connected in accordance with the arrangement order (S257). The length of a line segment obtained when the base points P4 to P9 are connected in order is the sum of distances D4 to D8. The length of a line segment obtained when the base points P21 to P25 are connected in order is the sum of distances D21 to D24. The CPU 1 calculates a weighting, on the basis of the lengths of the start point line segment LT1 and the end point line segment LT2 calculated at S256, and the length of the line segment inside the pair range candidate calculated at S257 (S258). For example, the CPU 1 calculates, as the weighting, a value obtained by dividing the length calculated at S257 by the sum of the length of the start point line segment LT1 and the length of the end point line segment LT2 obtained in the processing at S256. When the calculated weighting is equal to or greater than a predetermined value, the CPU 1 may substitute the predetermined value for the weighting.

Figure 27:
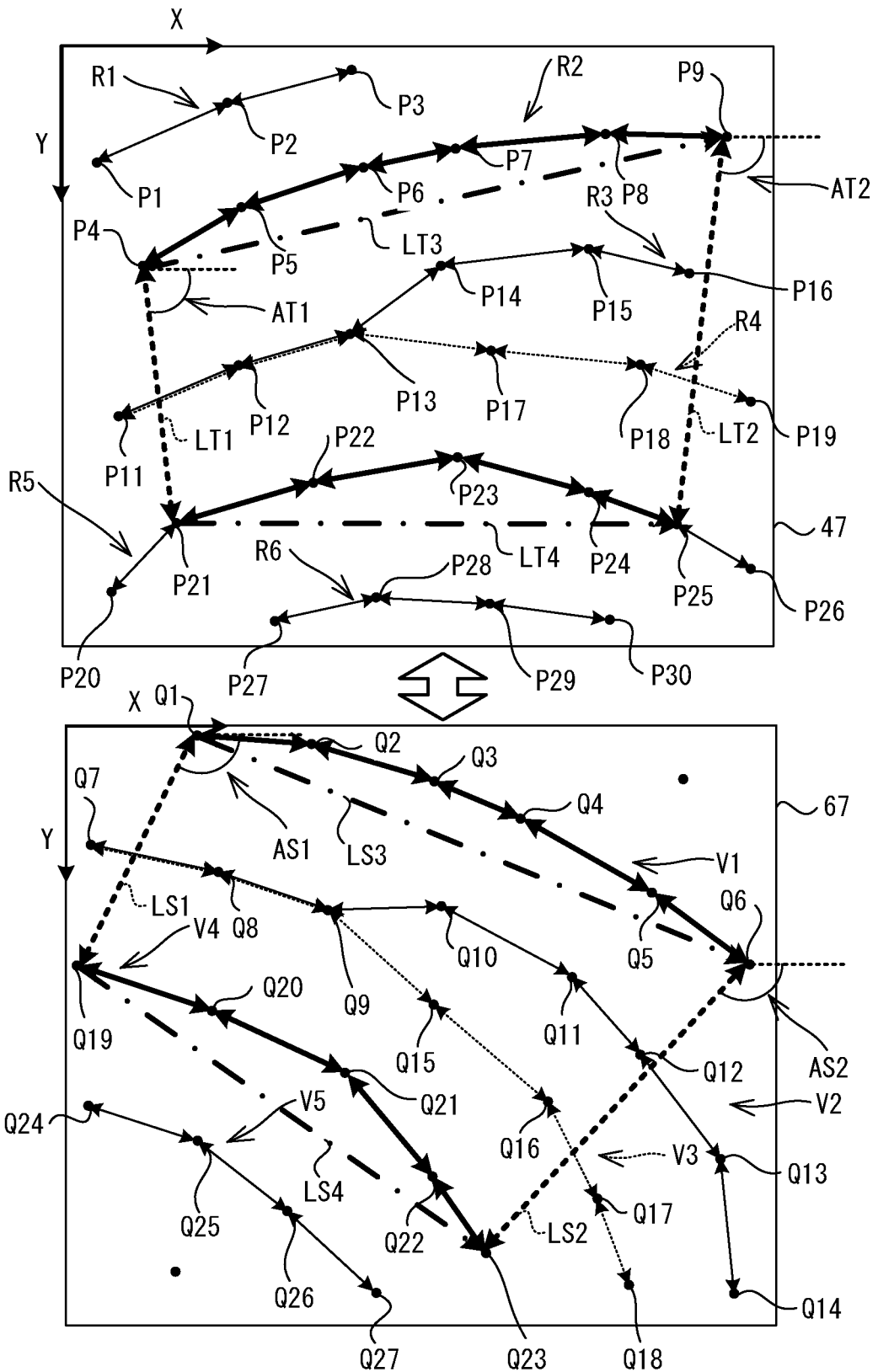
FIG. 27 is an explanatory diagram of an image represented by registration ridge information, and an image represented by collation ridge information.
Figure 28:
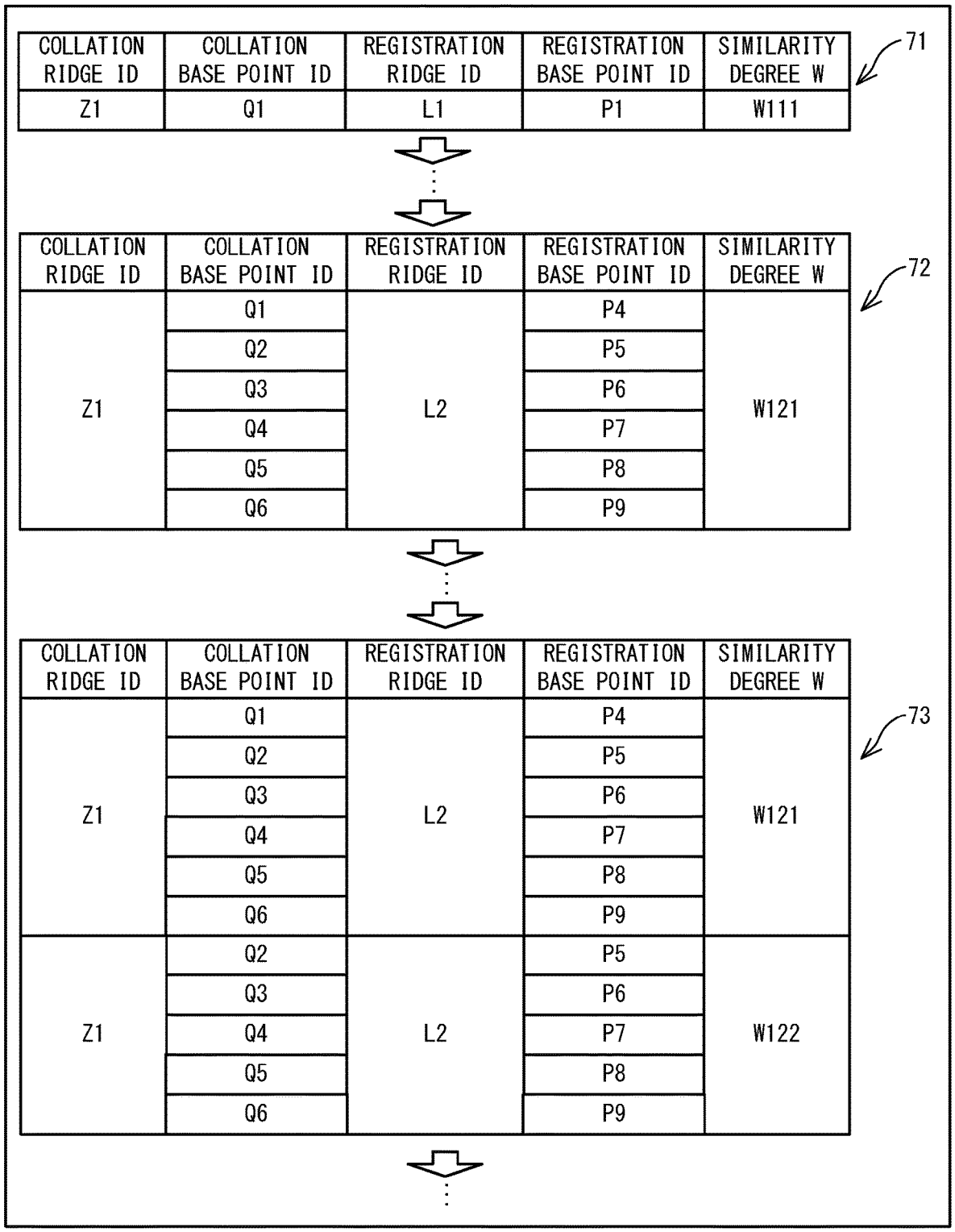
FIG. 28 is an explanatory diagram of a process that selects pair range candidates.

The CPU 1 calculates a degree of reliability, from the weighting calculated by the processing at S254, and the weighting calculated at S258 (S259). When, among the selected two sets of the collation ridge information Vn and the registration ridge information Rm, for at least one of the two pieces of collation ridge information and the two pieces of registration ridge information, one of the two pieces of ridge information is designated as first ridge information and the other is designated as second ridge information, the CPU 1 calculates the degree of reliability using the length of one or more comparison line segments obtained by connecting at least one of the endpoints of both ends of the first ridge information and at least one of the endpoints of both ends of the second ridge information. The CPU 1 of the present embodiment calculates, as the degree of reliability, the product of the weighting calculated by the processing at S254 and the weighting calculated at S258. Using differences in distances, a difference in angle and the degree of reliability calculated at S259, the CPU 1 calculates the similarity degree WR (S260). The differences in distances are a difference in the lengths of the collation start point line segment calculated at S253 and the length of the registration start point line segment calculated at S256, and a difference in the lengths of the collation end point line segment calculated at S253 and the registration end point line segment calculated at S256. Specifically, the differences in distances are the difference between the lengths of the line segments LS1 and LT1, and the difference between the lengths of the line segments LS2 and LT2. The difference in angle is a difference between an angle F1 and an angle F2. The angle F1 is a difference in angle between a collation first line segment and a registration first line segment. The angle F2 is a difference in angle between a collation second line segment and a registration second line segment. In FIG. 27, of the pair range candidates selected at S251, a line segment LS3 that connects the start point and the end point of one of the pair range candidates is the collation first line segment, and a line segment LS4 that connects the start point and the end point of the other pair range candidate is the collation second line segment. Of the pair range candidates selected at S255, a line segment LT3 that connects the start point and the end point of one of the pair range candidates is the registration first line segment, and a line segment LT4 that connects the start point and the end point of the other pair range candidate is the registration second line segment. For example, the CPU 1 calculates the similarity degree WR that is calculated on the basis of the ridge information, by substituting the differences in distances, the difference in angle, and the degree of reliability calculated at S259 into a predetermined formula. The similarity degree WR calculated at S258 indicates a greater degree of similarity the larger the value, and a lesser degree of similarity the smaller the value.

Figure 32:
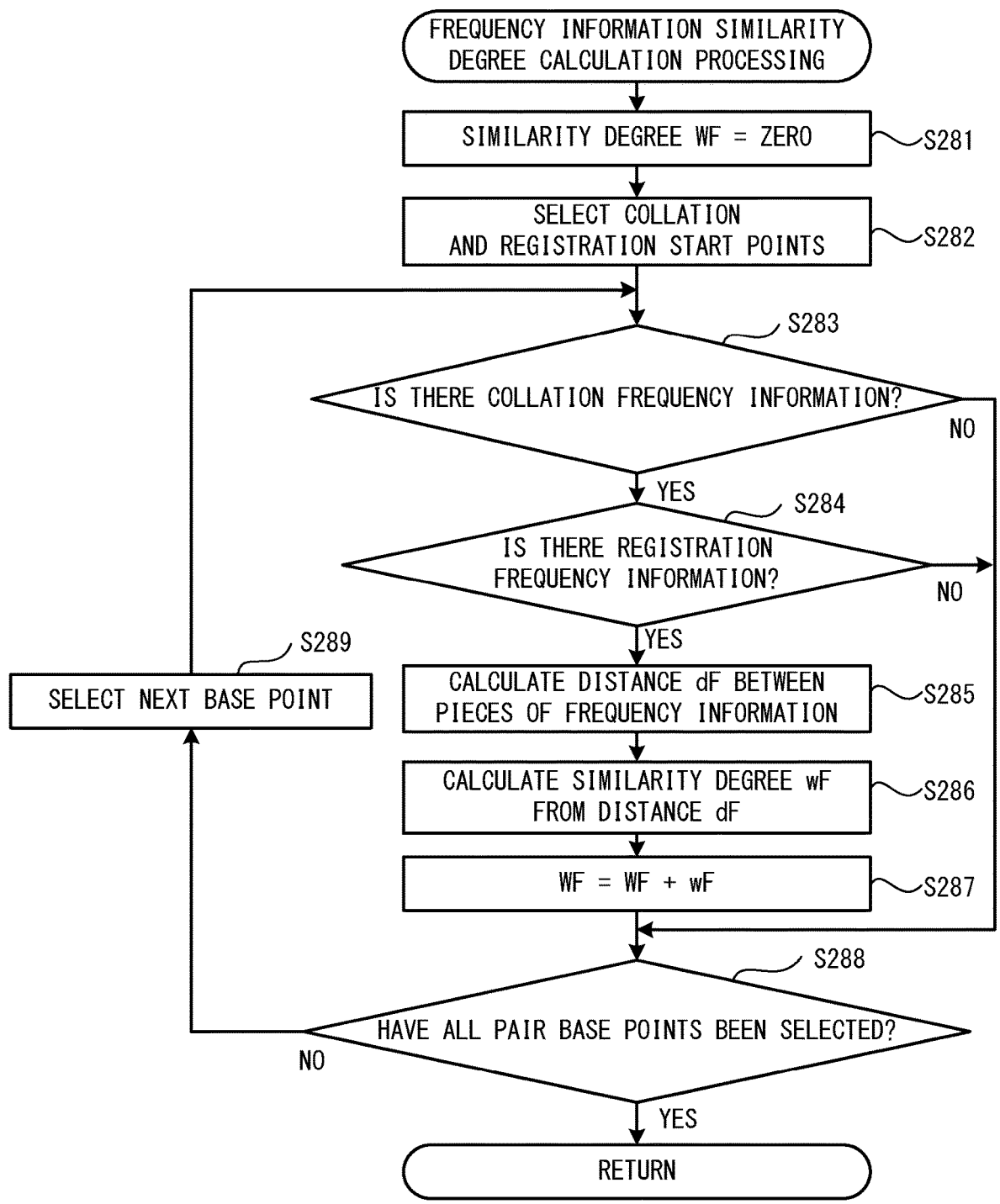
FIG. 32 is a flowchart of frequency information similarity degree calculation processing that is performed in the calculation processing shown in FIG. 31.
Figure 33:
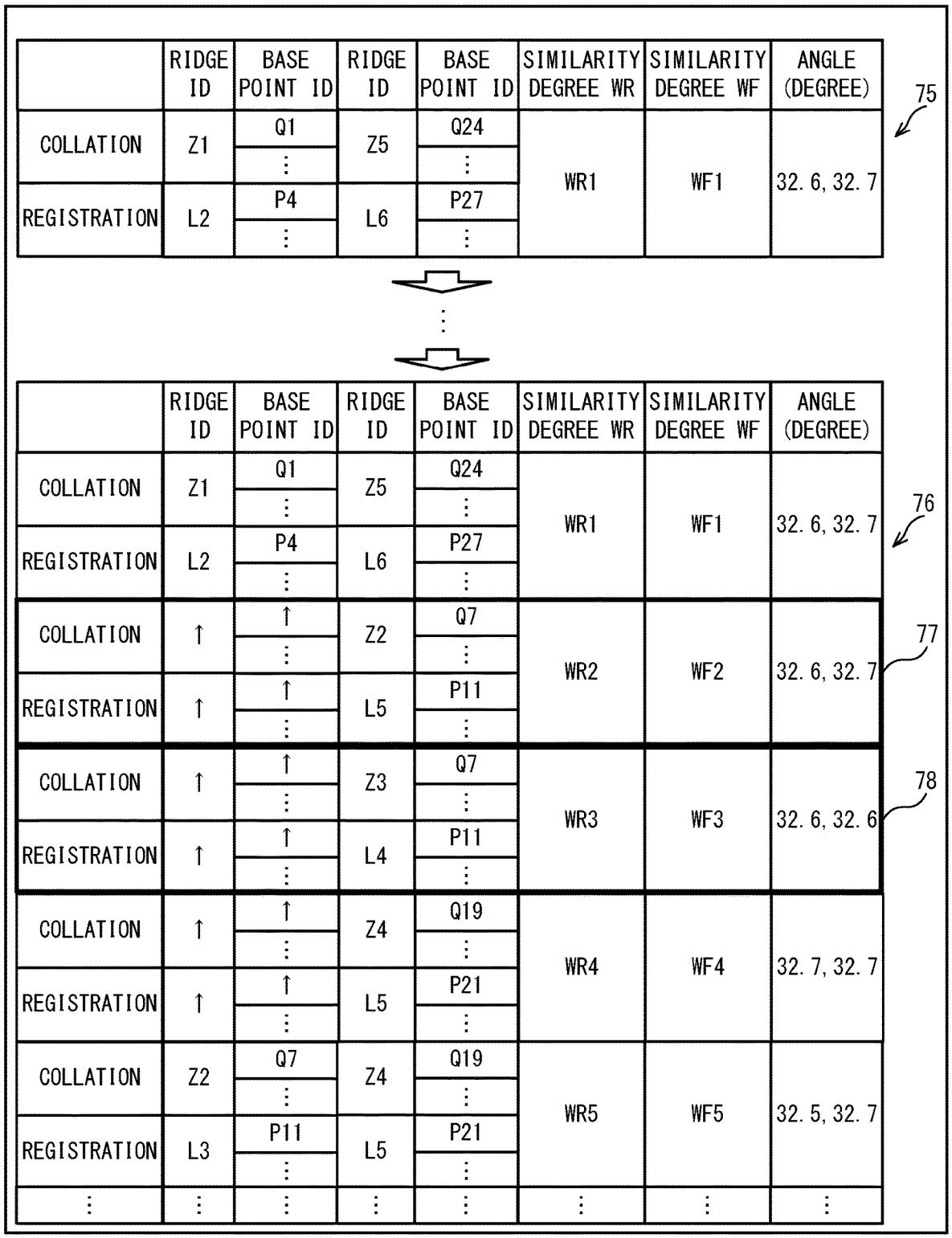
FIG. 33 is an explanatory diagram of a process that stores similarity degree calculation pairs, similarity degrees, and angles.

The CPU 1 determines whether the similarity degree WR calculated by the processing at S260 is larger than a threshold value (S261). When the similarity degree WR is not larger than the threshold value (no at S261), the CPU 1 performs processing at S266 to be described later. When the similarity degree WR calculated at S260 is larger than the threshold value (yes at S261), the CPU 1 performs similarity degree calculation processing of the frequency information (S262). As shown in FIG. 32, in the similarity degree calculation processing of the frequency information, the CPU 1 sets the similarity degree WF of the frequency information to zero (S281). The CPU 1 selects the start point of the selected collation pair range candidate and the start point of the selected registration pair range candidate (S282). The CPU 1 selects the base point Q1 of the ridge information V1 (the ridge Z1), the base point Q24 of the ridge information V5 (the ridge Z5), the base point P4 of the ridge information R2 (the ridge L2), and the base point P27 of the ridge information R6 (the ridge L6), as shown in FIG. 33. The CPU 1 determines whether the frequency information is stored for the selected collation base points Q1 and Q24 (S283). When the frequency information is not stored for at least one of the two collation base points (no at S283), the CPU 1 performs processing at S288 to be described later.

The frequency information is stored for both the collation base points Q1 and Q24 (yes at S283). In this case, the CPU 1 refers to the list 98 shown in FIG. 22 and determines whether the frequency information is stored for the selected registration base points P4 and P27 (S284).

When the frequency information is not stored for at least one of the two registration base points (no at S284), the CPU 1 performs the processing at S288 to be described later. The frequency information is stored for both the registration base points P4 and P27 (yes at S284). In this case, the CPU 1 calculates a distances dF of the frequency information, using the selected collation base points Q1 and Q24 and the selected registration base points P4 and P27 (S285). The CPU 1 calculates the distance dF on the basis of a distance between the base point Q1 and the base point P4, and a distance between the base point Q24 and the base point P27. The CPU 1 calculates a similarity degree wF from the distance dF calculated by the processing at S285 (S286). For example, the CPU 1 calculates the similarity degree wF, by substituting the distances dF into a predetermined formula. The CPU 1 adds the similarity degree wF calculated at S286 to the similarity degree WF of the frequency information, and updates the similarity degree WF of the frequency information (S287). The CPU 1 determines whether all of the base points of the selected pair range candidate have been selected by the processing at S282 or processing at S289 (S288). When there is the unselected base point (no at S288), the CPU 1 selects the next base point in the arrangement_order (S289), and returns the processing to S283. When all of the base points of the selected pair range candidate have been selected (yes at S288), the CPU 1 ends the similarity degree calculation processing of the frequency information, and returns the processing to the calculation processing shown in FIG. 31.

After S262 shown in FIG. 31, the CPU 1 determines whether the similarity degree WF of the frequency information calculated at S262 is larger than a threshold value (S263). When the similarity degree WF is not larger than the threshold value (no at S263), the CPU 1 performs processing that is similar to that of S266 of the third embodiment. When the similarity degree WF is larger than the threshold value (yes at S263), in an array of the similarity degrees, the CPU 1 stores each of the two collation pair range candidates selected at S251 and the two registration pair range candidates selected at S255, as similarity degree calculation pairs (S264). As shown in a list 75 in FIG. 33, the CPU 1 adds, to an array, the pair range candidates that include the six pairs of the base points Q1 to Q6 in the ridge information V1 (the ridge Z1), the pair range candidates that include the six pairs of the base points P4 to P9 in the ridge information R2 (the ridge L2), the pair range candidates that include the five pairs of the base points Q19 to Q23 in the ridge information V4 (the ridge Z4), the pair range candidates that include the five pairs of the base points P21 to P25 in the ridge information R5 (the ridge L5), and the similarity degrees WR and the similarity degrees WF of the frequency information calculated on the basis of these pair range candidates. In the array of the rotation angles of the image, the CPU 1 stores a rotation angle of the image calculated from the collation start point line segment and end point line segment calculated at S252, and the registration start point line segment and end point line segment calculated at S256 (S265). As shown in the list 75 in FIG. 33, the CPU 1 adds, to the array of the rotation angle of the image, each of the difference between the registration start point line segment LT1 and the collation start point line segment LS1 and the difference between the registration end point line segment LT2 and the collation end point line segment LS2.

The CPU 1 determines whether or not all of the registration pair range candidates corresponding to the two collation pair range candidates selected at S251 have been selected at S255 (S266). The processing at S266 is processing that takes into account a case in which the single pair range candidate is associated with a plurality of the pair range candidates, as in the case of the pair range candidates for the ridge information V5 (the ridge Z5) in the list 74 in FIG. 29. When some of the registration pair range candidates corresponding to the two collation pair range candidates selected at S251 have not been selected at S255 (no at S266), the CPU 1 returns the processing to S255. When all of the registration pair range candidates corresponding to the two collation pair range candidates selected at S251 have been selected at S255 (yes at S266), the CPU 1 determines whether all of the combinations of the collation pair range candidates selected by the processing at S201 have been selected in the processing at S251 (S267). In the specific example, when, on the basis of the list 74 in FIG. 29, all of the ten combinations of the five collation pair range candidates have not been selected in the processing at S251 (no at S267), the CPU 1 returns the processing to S251. When all of the ten combinations of the five collation pair range candidates have been selected in the processing at S251 (yes at S267), the CPU 1 ends the calculation processing and returns the processing to the pair range determination processing shown in FIG. 30. As a result of the calculation processing shown in FIG. 31, the similarity degrees and the angles are stored for a plurality of similarity degree pairs, as in a list 76 shown in FIG. 33.

Figure 34:
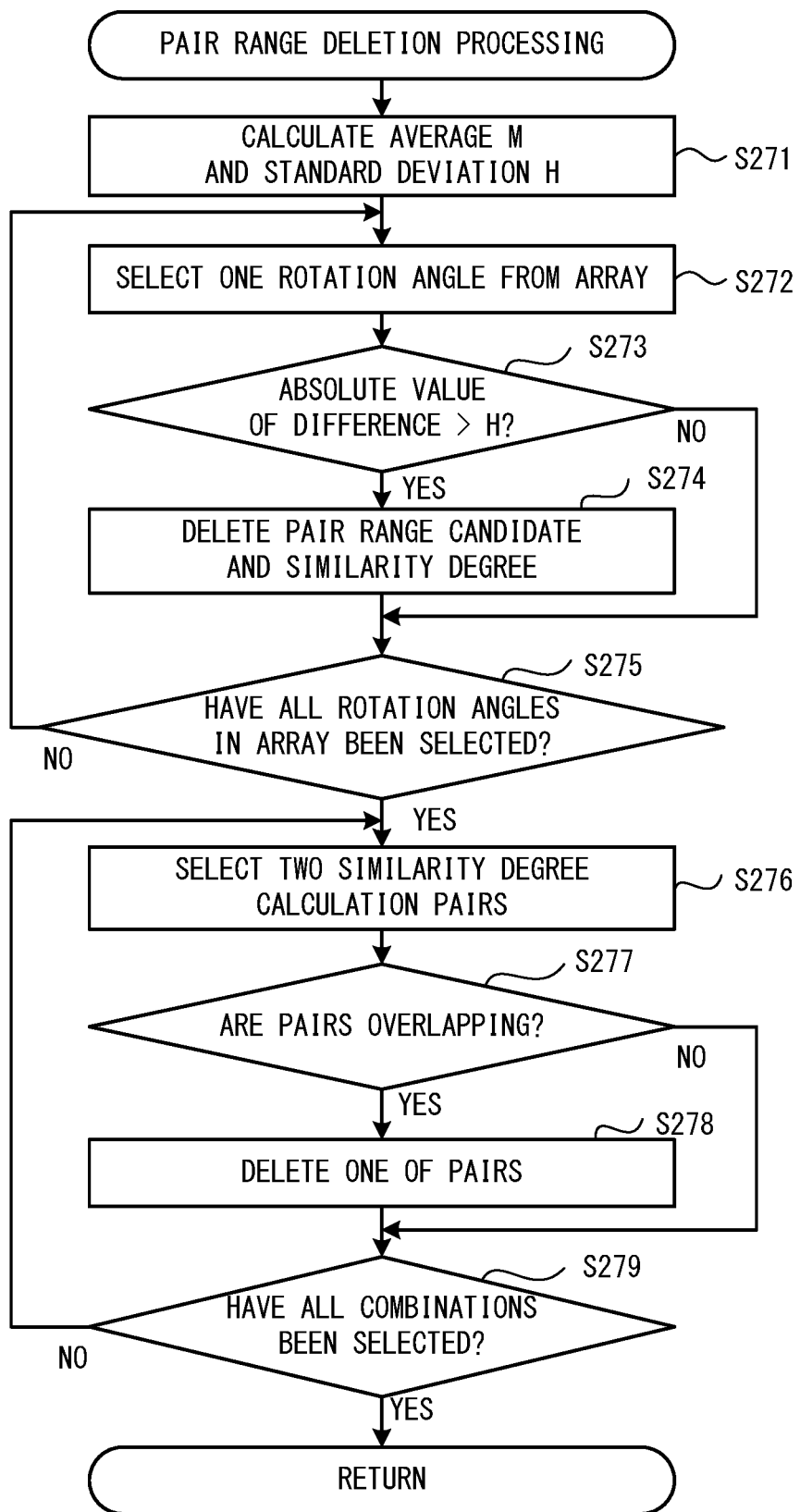
FIG. 34 is a flowchart of pair range deletion processing that is performed in the pair range determination processing shown in FIG. 30.

After S244 in FIG. 30, the CPU 1 determines whether a number of the similarity degrees WR (a number of the similarity degree pairs) added to the array by the processing at S264 in FIG. 31 is larger than a threshold value (S245). When the number of the similarity degrees WR is not larger than the threshold value (no at S245), the CPU 1 ends the pair range determination processing, and returns the processing to the collation processing shown in FIG. 25. When the number of similarity degrees WR is larger than the threshold value (yes at S245), the CPU 1 performs pair range deletion processing (S246). The pair range deletion processing is processing that determines the pair range to be used in calculation of a similarity degree of pair ranges that satisfy predetermined conditions, by deleting the similarity degree calculation pairs that do not satisfy the predetermined conditions from among the similarity degree calculation pairs selected by the pair range candidate selection processing at S201 and stored at S264 of the calculation processing at S244. Specifically, as shown in FIG. 34, in the pair range deletion processing, the CPU 1 calculates an average value M and a standard deviation H of the angles added to the array by the processing at S265 in FIG. 31 (S271). The CPU 1 selects one of the angles among the angles stored at S265 (S272). The CPU 1 determines whether an absolute value of a difference between the angle selected at S272 and the average value M of the angles calculated at S271 is larger than the standard deviation H (S273). When the absolute value of the difference with the average value M of the angles calculated at S271 is larger than the standard deviation H (yes at S273), the CPU 1 deletes the pair range candidate, the similarity degree WR and the angle corresponding to the angle selected at S272, from the array (S274). When the absolute value of the difference with the average value M of the angles calculated at S271 is not larger than the standard deviation H (no at S273), or after the processing at S274, the CPU 1 determines whether all the angles added to the array at S265 have been selected by the processing at S272 (S275). When there is the angle that has not been selected by the processing at S272 (no at S275), the CPU 1 returns the processing to S272. When all of the angles have been selected by the processing at S272 (yes at S275), and when, of the similarity degree calculation pairs stored by the processing at S264, a plurality of pair range candidates are stored for one of the two sets of collation pair range candidates or the two sets of registration pair range candidates, the CPU 1 selects the two sets of pair range candidates from the plurality of pair range candidates (S276). For example, as shown in the list 76 in FIG. 33, with respect to the pair range candidates set in the collation ridge information V1 (the ridge Z1), the similarity degrees WR are calculated taking the pair range candidates set in each of the collation ridge information V2 to V5 as similarity degree calculation pairs. For example, from among the pair range candidates set in each of the collation ridge information V2 to V5, the CPU 1 selects the pair range candidate set in the ridge information V2 of a similarity degree calculation pair 77 and the pair range candidate set in the ridge information V3 of a similarity degree calculation pair 78.

Of the similarity degree calculation pairs selected by the processing at S276, the CPU 1 determines whether line segments obtained when the plurality of base points are connected in accordance with the arrangement order are partially overlapping (S277). In the case of the pair range candidate set in the ridge information V2, and the pair range candidate set in the ridge information V3, line segments from the base points Q7 to Q9 are overlapping (yes at S277). In this case, of the similarity degree calculation pairs 77 and 78, the CPU 1 deletes the pair for which the similarity degree is smaller (S278). When the similarity degree calculation pairs selected at S276 are not overlapping (no at S277), or after S278, the CPU 1 determines whether all of the similarity degree calculation pairs have been selected by the processing at S276 (S279). When one of the combinations has not been selected by the processing at S276 (no at S279), the CPU 1 returns the processing to S276. When all of the combinations of the similarity degree calculation pairs have been selected by the processing at S276 (yes at S279), the CPU 1 ends the pair range deletion processing, and returns the processing to the pair range determination processing shown in FIG. 30. After the processing at S246, the CPU 1 ends the pair range determination processing, and returns the processing to the collation processing shown in FIG. 25.

After S202 shown in FIG. 25, the CPU 1 calculates a score SC, using the sum of the similarity degrees WR calculated at S260 that have not been deleted by the pair range deletion processing shown in FIG. 34 and the sum of the similarity degrees WF frequency information of the (S203). The score SC indicates a similarity degree between the collation ridge information and frequency information, and the registration ridge information and frequency information. For example, the CPU 1 calculates the score SC by substituting the sum of the similarity degree WR and a similarity degree WF into a predetermined formula. The score SC of the present embodiment indicates a greater similarity degree between the collation ridge information Vn and the frequency information, and the registration ridge information Rm and the frequency information the larger the value, and indicates a lesser similarity degree the smaller the value. The CPU 1 determines whether the score SC calculated at S203 is larger than a threshold value (S204). When the score SC is larger than the threshold value (yes at S204), the CPU 1 sets "Success" as an authentication result of the skin authentication (S205). When the score SC is not larger than the threshold value (no at S204), the CPU 1 sets "Failure" as the authentication result of the skin authentication (S206). In the processing at S205 and S206, the CPU 1 may perform notification as necessary by displaying the authentication result on the display portion 6 or the like. The CPU 1 ends the collation processing and returns the processing to the skin authentication processing shown in FIG. 8. After S15 in FIG. 8, the CPU 1 ends the skin authentication processing.

Evaluation Test

Figure 35:
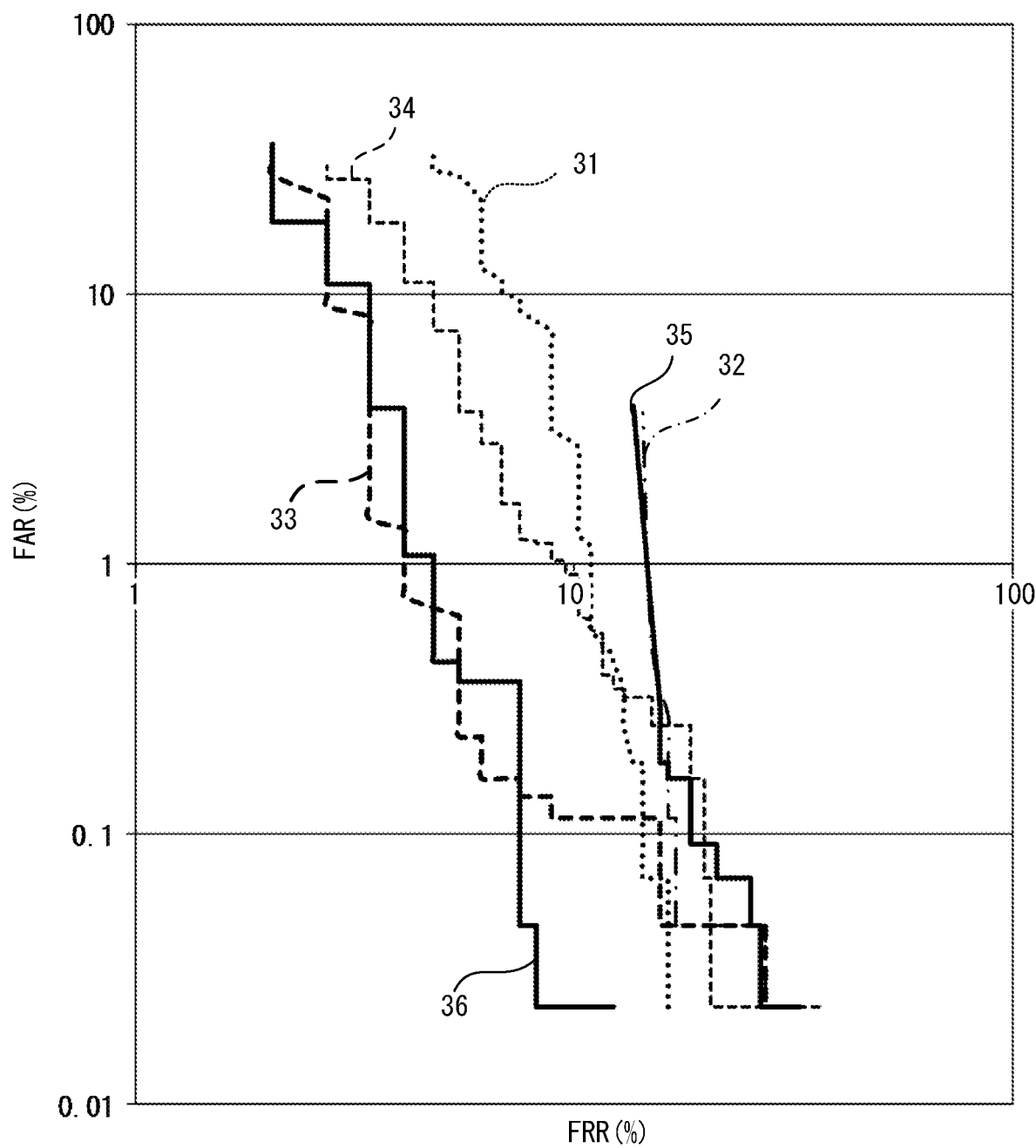
FIG. 35 is a graph showing authentication test results.

An evaluation test was conducted, using the ridge information for the skin authentication, to verify whether the authentication performance improves. For each of conditions 1 to 6 to be described below, an optical touch sensor was used to acquire 5 to 10 images per finger of 31 fingers, each being an image of 2000 dpi having 480 pixels in the horizontal direction and 800 pixels in the vertical direction. One of the images was used as a registration image and another of the images was used as a collation image, and receiver operating characteristics (ROC) were calculated. Condition 1 is a condition to perform the skin authentication using a known minutia method. Condition 2 is a condition to perform the skin authentication using the ridge information of the third embodiment. Condition 3 is a condition to perform the skin authentication using both the minutia method and the ridge information. Condition 4 is a condition to perform the skin authentication using the frequency information showing the changes in color around a feature point extracted using the minutia method. Condition 5 is a condition to perform the skin authentication using the frequency information showing an area surrounding the base point representing the sweat pore. Condition 6 is a condition to perform the skin authentication by combining Condition 5 and Condition 6. Each of Conditions 1 to 6 are shown by results 31 to 36 in FIG. 35. As shown in FIG. 35, when Conditions 1 to 3 are compared, in comparison to Condition 1, Condition 3 shows a superior authentication performance. From this, it was verified that the ridge information can improve the authentication performance of a known authentication method. In comparison to Condition 4, Condition 6 shows a superior authentication performance. From this, it was verified that the frequency information showing the changes in the color surrounding the sweat pore can improve the authentication performance of the known authentication method.

The skin information processing device 10 can generate the frequency information showing the changes in color around the base point, when the sweat pore on the ridge of the skin in the image is used as the base point. The arrangement of sweat pores on the ridges of the skin is unique, in the same way as a fingerprint or a voiceprint, and is said not to change over the period of a whole lifetime. Even when the size of the image that represents the skin information is smaller than in the related art, and the branch points and endpoints of the ridges are not included in the image, there is a possibility that a plurality of the sweat pores can be acquired. The skin information processing device 10 can generate the frequency information that is able to cancel out an influence of the base point rotating or moving with respect to a reference, when using the base point representing the characteristic sweat pore as the biometric information. In other words, even when the size of the image representing the skin information is smaller than in the related art, the skin information processing device 10 can generate the information that is not easily influenced by acquisition conditions of the biometric information, The skin information processing device 10 extracts the plurality of base points arranged on the same continuous ridge, from among the plurality of base points determined by the processing at S23 (S65), and generates the position information of each of the extracted plurality of base points, and the ridge information that includes the arrangement order of the plurality of identified base points on the ridge (S72). The skin information processing device 10 associates the ridge information generated at S72 with the frequency information, and stores the associated information in the RAM 3 (the storage portion) as the information to be used in the skin authentication (S28). Thus, the skin information processing device 10 can generate the ridge information and store the ridge information and the frequency information in association with each other. The ridge information includes the position information indicating the position, in the image, of each of the plurality of base points arranged on the same continuous ridge, and the arrangement order of the plurality of base points on the ridge. The base point represents the sweat pore on the ridge. When the plurality of base points are connected by the line segment in order in accordance with the arrangement order, a plurality of the line segments connecting the plurality of base points form the shape of the ridge as a whole. A length of each of the line segments represents a distance between the adjacent base points arranged on the same continuous ridge. Specifically, the ridge information is information representing the shape of the ridge using the arrangement of the sweat pores, and it can be said that it is information that emphasizes characteristic sections of the biometric information represented by the image. Thus, in addition to the frequency information generated on the basis of the base points, the skin information processing device 10 can generate the ridge information that is the information used in the skin authentication and that contributes to an improvement in authentication performance, in comparison to the related art.

For each of the plurality of base points extracted by the processing at S65, the skin information processing device 10 calculates the relative angle of the line segment connecting the base point with the preceding base point in the arrangement order on the ridge with respect to the line segment connecting the base point with the next base point in the arrangement order (S116). For the plurality of reference points on the circumference of the circle whose center is the base point determined by the processing at S23 and whose radius is the predetermined value, the skin information processing device 10 takes, as the starting point, the point determined on the basis of the base point and the relative angles calculated at S115 and S119 with respect to the base point. Then, for each of the plurality of reference points acquired in order in accordance with the predetermined conditions, the skin information processing device 10 acquires, as the sample information, information that associates the color information corresponding to the reference point with reference position information corresponding to the position of the reference point on the image (S116). The skin information processing device 10 calculates the frequency components of the changes in the color information with respect to the reference position information acquired at S116 and S120, respectively, using a linear prediction coefficient which is calculated without multiplying a window function, and generates the frequency information (S117, S121). The skin information processing device 10 generates the ridge information that includes the position information of each of the plurality of base points, the arrangement order of the plurality of identified base points on the ridge, and the relative angles. Thus, at S116 and S120, the skin information processing device 10 can determine the acquisition starting point using the arrangement of the base points on the same continuous ridge. The skin information processing device 10 can generate the ridge information that includes the relative angles. Since the ridge information includes the relative angles, when performing the skin authentication using the ridge information, the skin information processing device 10 does not need to newly calculate the relative angles between the base points. In other words, the skin information processing device 10 can shorten an authentication time when performing the skin authentication. By generating the ridge information that includes the relative angles, the skin information processing device 10 can calculate the similarity degree while taking into account an influence of angle in a case in which, when the skin authentication is performed, an image is acquired under an angle condition different from that at the time of registration.

The skin information processing device 10 determines the positional correspondence that is the correspondence between the base point of the collation ridge information used in the skin authentication at S201 and S202, and the base point of the registration ridge information stored in the DB 28. On the basis of the determined positional correspondence, the skin information processing device 10 calculates the score SC that is the similarity degree between the collation ridge information and frequency information, and the registration ridge information and frequency information (S262). The skin information processing device 10 can compare the frequency information for collation and the frequency information for registration, and calculate the similarity degree between them, while taking into account an influence of the information represented by the image rotating or moving with respect to the reference, when using the base point representing the characteristic sweat pore as the skin information. In other words, when the skin information processing program is executed, a computer can appropriately calculate the score SC on the basis of collation information that is not easily influenced by the acquisition conditions of the skin information, even when the size of the image representing the skin information is smaller than in the related art.

The skin information processing device 10 determines the area centroid of the sweat pore in the image as the base point, and uses the area centroid as the position information of the base point. The skin information processing device 10 can determine the area centroid of the sweat pore, which represents features of the shape and size of the sweat pore, as the base point, and can generate the ridge information.

The skin information processing device 10 calculates the distance from the base point to the next base point in the arrangement order (S34), and generates the ridge information that includes the position information of each of the plurality of base points on the same continuous ridge, and the arrangement order and distances of the identified base points on the ridge (S72). The skin information processing device 10 can generate the ridge information that includes the distance to the next base point in the arrangement order. The ridge information includes the distance to the next base point in the arrangement order, and thus, when the ridge information is used to perform the skin authentication, with respect to the registration ridge information, it is not necessary to newly calculate the distances between the base points. The skin information processing device 10 can generate the ridge information that includes the distance to the next base point in the arrangement order, and thus, the similarity degree can be calculated while taking into account an influence of position, in a case in which, when the skin authentication is performed, an image is acquired under a position condition that is different from that at the time of registration.

The skin information processing device 10 calculates, for each of the plurality of base points on the same continuous ridge, the relative angle between the line segment connecting the base point with the preceding base point in the arrangement order and the line segment connecting the base point with the next base point in the arrangement order (S82). For each of the plurality of base points on the same continuous ridge, the skin information processing device 10 generates the ridge information that includes the position information, and the arrangement order and the relative angles of the identified base points on the ridge (S72). The skin information processing device 10 generates the ridge information that includes the relative angles, and thus, when the ridge information is used to perform the skin authentication, a computer does not need to newly calculate the relative angles between the base points. The skin information processing device 10 can shorten an authentication time at the time of the skin authentication. By generating the ridge information that includes the relative angles, the skin information processing device 10 can calculate the similarity degree while taking into account an influence of angle in a case in which, when the skin authentication is performed, an image is acquired under an angle condition that is different from that at the time of registration.

When each of the plurality of base points is taken as the target base point, the skin information processing device 10 generates, as the connection information, the information that associates the position information of the target base point with the position information of the connection base point, which is the base point that is disposed on the same continuous ridge as the target base point, and that precedes or follows the target base point in the arrangement order on the same continuous ridge (S25). On the basis of the connection information generated at S25, the skin information processing device 10 extracts the plurality of base points arranged on the same continuous ridge (S65). In comparison to when the processing at S25 is not performed, the skin information processing device 10 can more appropriately generate the ridge information through simpler processing.

On the basis of the connection information generated by the processing at S25, the skin information processing device 10 identifies, of the plurality of base points, the base point for which the number of preceding or following base points in the arrangement order is 1, as the start point that is the first base point in the arrangement order or as the end point that is the last base point in the arrangement order. The skin information processing device 10 identifies, of the plurality of base points, the base point for which the number of preceding and following base points is three or more, as the branch point of the ridge. When the continuous ridge does not include the branch point, the skin information processing device 10 defines the ridge that does not have the bifurcation from the start point to the end point, extracts the plurality of base points arranged on the defined ridge, and generates the ridge information. When the continuous ridge includes the branch point, the skin information processing device 10 defines the plurality of ridges without the bifurcation from the start point to the end point including the branch point, the number of ridges corresponding to the number of bifurcations at the branch point. For each of the defined plurality of ridges, the plurality of base points arranged on the same ridge are extracted and the ridge information is generated. Thus, when the branch point is included on the same continuous ridge, the skin information processing device 10 defines the plurality of ridges without the bifurcation from the start point to the end point, from the same continuous ridge that includes the branch point, and thus, the ridge information can be generated in which all of the ridges can be treated as the ridges that do not include the branch point.

The skin information processing device 10 determines the positional correspondence that is the correspondence between the base point of the collation ridge information used in the skin authentication, and the base point of the registration ridge information stored in the DB 28 (S201 and S202 in FIG. 25). On the basis of the determined positional correspondence, the skin information processing device 10 calculates the similarity degree WR between the collation ridge information and the registration ridge information (S260), and calculates the score SC using the calculated similarity degree WR (S203). Thus, the skin information processing device 10 uses the ridge information which represents the shape of the ridge using the arrangement of the sweat pores and in which the feature points of the biometric information represented by the image are emphasized. Thus, in comparison to a case in which the relative positions of the sweat pores are simply compared, the processing can be performed with a higher degree of reliability in the determination of the positional correspondence and the calculation of the similarity degree.

In the processing at S201 and S202 shown in FIG. 25, from the plurality of combinations of the collation ridge information and registration ridge information, the skin information processing device 10 identifies the pair ranges for which the difference between the selected collation ridge information and the selected registration ridge information is equal to or less than the threshold value for the base points over a predetermined continuous number of base points, and then determines the positional correspondence. Thus, the skin information processing device 10 can determine the positional correspondence using relatively simple processing.

The skin information processing device 10 selects two sets of the collation ridge information and registration ridge information for which the pair range candidate has been identified (S251, S255). For each of the two selected sets of the collation ridge information and registration ridge information, the skin information processing device 10 identifies both the ends of the line segment obtained by connecting the plurality of base points in the pair range in accordance with the arrangement order, compares both the ends respectively corresponding to the two pieces of collation ridge information with both the ends respectively corresponding to the two pieces of registration ridge information, and calculates the score SC (S254, S258, S259, S260, and S203). By comparing both the ends of the ridge information in the pair ranges, the skin information processing device 10 can efficiently compare the collation ridge information and the registration ridge information and calculate the similarity degree.

When, among the two sets of the collation ridge information and the registration ridge information selected by the processing at S251 and S255, for at least one of the two pieces of collation ridge information and the two pieces of registration ridge information, one of the two pieces of ridge information is designated as the first ridge information and the other is designated as the second ridge information, the skin information processing device 10 calculates the degree of reliability using the length of one or more of the comparison line segments obtained by connecting at least one of the endpoints of both ends of the first ridge information and at least one of the endpoints of both ends of the second ridge information (S259). The skin information processing device 10 calculates the similarity degree WR by multiplying a comparison result of the relative positions by the degree of reliability, and calculates the score SC using the calculated similarity degree WR (S260). In comparison to a case in which the similarity degree WR is calculated without using the degree of reliability, the skin information processing device 10 can calculate the similarity degree offering a high degree of authentication accuracy.

The skin information processing device and the non-transitory computer-readable medium according to the present disclosure is not limited to the embodiments described above, and various types of modifications may be made insofar as they are within the scope of the present disclosure. For example, the modifications (A) to (C) described below may be made as desired.

(A) The configuration of the skin information processing device 10 may be changed as appropriate. For example, the skin information processing device 10 is not limited to a smart phone, and may be a mobile device, such as a notebook PC, a tablet PC or a mobile telephone, for example, or may be a device such as an automated teller machine (ATM) or an entrance and exit management device. The skin information acquisition device 8 may be provided separately from the skin information processing device 10. In this case, the skin information acquisition device 8 and the skin information processing device 10 may be connected by a connection cable, or may be wirelessly connected, such as with Bluetooth (registered trademark) or near field communication (NFC). The detection method of the skin information acquisition device 8 is not limited to the capacitance method, and may be another method (for example, an electric field method, a pressure method, or an optical method). The skin information acquisition device 8 is not limited to the surface type, and may be a linear type. The size, the color information and the resolution of the image generated by the skin information acquisition device 8 may be changed as appropriate. Therefore, for example, the color information may be information corresponding to a color image, as well as information corresponding to a white and black image.

(B) The skin information processing program may be stored in a storage device of the skin information processing device 10 before the skin information processing device 10 executes the programs. Therefore, the methods by which the information processing programs are acquired, the routes by which they are acquired, and the device in which the programs are stored may each be modified as desired. The skin information processing programs, which are executed by the processor of the skin information processing device 10, may be received from another device through one of a cable and wireless communications, and they may be stored in a storage device such as a flash memory or the like. The other device may be, for example, a personal computer (PC) or a server that is connected through a network.

(C) The individual steps in the skin information processing may not necessarily be performed by the CPU 1, and some or all of the steps may also be performed by another electronic device (for example, an ASIC). The individual steps of the skin information processing may also be performed by distributed processing among a plurality of electronic devices (for example, a plurality of CPUs). The order of the individual steps in the collation information processing can be modified as necessary, and steps can be omitted and added. A case in which an operating system (OS) or the like that is operating in the skin information processing device 10 performs some or all of the actual processing, based on commands from the CPU 1 of the skin information processing device 10, and the functions of the embodiment that is described above are implemented by that processing, falls within the scope of the present disclosure. The modifications hereinafter described in paragraphs (C-1) to (C-8) may also be applied to the main processing as desired.

(C-1) Pre-processing may be performed, as appropriate, on the image acquired at S11. For example, filtering processing may be performed in order to remove high frequency components of the image as noise. As a result of performing the filtering processing, gradation changes in edge portions of the image become moderate. One of a known low pass filter, a Gaussian filter, a moving average filter, a median filter and an averaging filter may be used as a filter used for the filtering processing. In another example, the filtering processing to extract specific frequency band components only may be performed on the image acquired at S11. A band including a ridge and trough period of the fingerprint may be selected as the specific frequency band. In this case, a known band-pass filter can be taken as an example of the filter used for the filtering processing.

(C-2) As long as the base point is a point that represents the sweat pore, the base point need not necessarily be the area centroid of the sweat pore. It is sufficient that the ridge information include at least the position information of the base points and the arrangement order of the base points on the ridge. The arrangement order may be indicated by a storage order of the position information. The ridge information may include, as the angle of the base point, the orientation of the vector from the base point toward the preceding base point in the arrangement order, and the orientation of the vector from the base point to the following base point in the arrangement order. The ridge information need not necessarily define the ridge without the bifurcation, when the branch point is included in the base points on the same continuous ridge. For example, the ridge information including the bifurcation, as shown in the ridge information R3 in FIG. 27, may be defined. The ridge information need not necessarily be generated on the basis of the connection information. The processing to generate the connection information may be omitted as necessary.

(C-3) When determining the positional correspondence that is the correspondence between the base points of the collation ridge information used in the skin authentication, and the base points of the registration ridge information stored in the DB 28, the skin information processing device may determine the positional correspondence while taking partially missing sweat pores into account. For example, a case is assumed in which, when comparing the registration ridge information R1 to R5 shown in the image 47 and the collation ridge information V1 to V4 shown in the image 67 in FIG. 27, the base point P26 in the collation ridge information V4 is missing. In this case, in the processing of the above-described embodiments, after comparing the base point Q25 of the ridge information V4 and a base point P28 of the ridge information R5, the base point Q27 of the ridge information V4 and a base point P29 of the ridge information R5 are compared. Even if it is determined, on the basis of the distances and relative angles, that the base point Q27 and the base point P29 are not similar, if it is determined that the base point Q27 is similar to the base point P28, on the basis of the distance of the base point P30, which follows the base point P27 in the arrangement order, from the base point P28 and the relative angle, the pair range may be set while passing over the base point P29.

(C-4) The calculation method of the degree of reliability may be changed as appropriate. The degree of reliability may be calculated by identifying, for each of the two sets of collation ridge information and registration ridge information for which the pair range is identified, both the ends of the line segment obtained when the plurality of base points in the pair range are connected in accordance with the arrangement order, and comparing both the ends respectively corresponding to the two pieces of collation ridge information with both the ends respectively corresponding to the two pieces of registration ridge information. Thus, the degree of reliability may be calculated using the following procedure, for example. From the two pieces of collation ridge information, a first line segment and a second line segment are defined that are obtained when the base points in the set pair range are connected in accordance with the arrangement order. Both ends of the first line segment are a first start point and a first end point, and both ends of the second line segment are a second start point and a second end point. A line segment obtained when the first start pint and the second start point are connected is a first comparison line segment. A line segment obtained when the first end point and the second end point are connected is a second comparison line segment. A line segment obtained when the first start point and the second end point are connected is a third comparison line segment. A line segment obtained when the first end point and the second start point are connected is a fourth comparison line segment. The degree of reliability may be calculated on the basis of at least one of the first to fourth comparison line segments. For example, the degree of reliability may be calculated using only the first comparison line segment, or the degree of reliability may be calculated using the first to fourth comparison line segments in combination.

(C-5) The collation information including at least one of the generated connection information and the ridge information need not necessarily be used in the processing to calculate the information similarity degree. The skin authentication may be performed in combination with known collation information. For example, a final determination may be made by combining a collation result from a known minutia method and a collation result using the collation information method of the present disclosure. If this is done, the collation is performed from diverse viewpoints, and it is expected that the collation accuracy will improve. Further, a configuration may be adopted in which the collation method can be automatically set or set by the user, from among a plurality of types of collation method, while taking account of processing time and authentication accuracy and the like.

(C-6) It is sufficient that the frequency information be information showing changes in the color around the base point. For example, the frequency components are not limited to the one-dimensional group delay spectrum. For example, other known frequency components, such as an LPC spectrum, a group delay spectrum, an LPC cepstrum, a cepstrum, an autocorrelation function, a cross correlation function and the like may be used as the frequency components. The frequency information need not necessarily be associated with the ridge information. The frequency information may be associated with the connection information. The processing to calculate the frequency information may be omitted.

(C-7) The calculation method of the frequency information may be changed as appropriate. For example, when the one-dimensional group delay spectrum is used as the frequency components as in the above-described embodiments, noise components sometimes appear strongly in high frequency components. Taking this type of case into account, the frequency information may be selected on the basis of frequency information that includes a predetermined number of components selected while prioritizing lower order components. The predetermined number may be set in advance while taking into account a number of samples, authentication accuracy and the like. For example, when the number of samples N acquired for a single first reference point is 128, the predetermined number is set to a value from 10 to 63. Preferably, the predetermined number is set to be a value between 12 to 20. When the number of samples is N, the predetermined number is preferably set to a value from (number of samples N/10) to (number of samples N/5). For example, the frequency information may be calculated using a window function.

(C-8) The acquisition method of the samples may be changed as appropriate. The samples may be acquired using a direction indicating a feature in the changes in the color information around the base point. A curvature of the changes in the color information around the base point may be calculated as part or all of a reference direction. The curvature refers to an amount indicating a degree of curvature of a curved line. Various setting values set in the collation information processing, threshold values, and the like may be changed as appropriate. For the various setting values, threshold values, and the like, a plurality of types may be set depending on acquisition conditions of the base point (a number, a surface area, and a shape of the sweat pores, and so on).

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A skin information processing method for a skin information processing device comprising a storage portion, the skin information processing method comprising:
   acquiring an image;
   determining a base point representing a sweat pore on a ridge of skin, from the acquired image and acquiring position information corresponding to a position of the base point on the image;
   acquiring sample information indicating changes in color information around the determined base point;
   generating, as frequency information, information associating frequency components of the acquired sample information with the position information; and
   causing the storage portion to store information including the generated frequency information and the position information of the base point, as information used in skin authentication.

2. The skin information processing method according to claim 1, further comprising:
   extracting, from among a plurality of the base points, a plurality of the base points disposed on a same continuous ridge; and
   generating ridge information including the position information of each of the plurality of extracted base points, and an arrangement order of the plurality of extracted base points on the ridge, and wherein the causing the storage portion to store information includes causing the storage portion to store the generated ridge information and the frequency information, in association with each other, as the information used in the skin authentication.

3. The skin information processing method according to claim 2, further comprising:

calculating, for each of the plurality of extracted base points, a relative angle of a line segment connecting the base point and a following base point in the arrangement order with respect to a line segment connecting the base point and a preceding base point in the arrangement order, and wherein:

the acquiring the sample information includes acquiring, as the sample information, information associating color information corresponding to a reference point with reference position information corresponding to a position of the reference point on the image, for each of a plurality of the reference points, the plurality of reference points being on a circumference of a circle whose center is the determined base point and whose radius is a predetermined value, and the plurality of reference points being acquired sequentially in accordance with a predetermined condition from a starting point determined on the basis of the base point and the calculated relative angle, the generating the frequency information includes calculating frequency components of changes in the color information with respect to the reference position information for the acquired sample information, using a linear prediction coefficient calculated without multiplying a window function, and generating the frequency information, and the generating the ridge information includes generating the position information of each of the plurality of extracted base points, the arrangement order of the extracted plurality of base points on the ridge, and the relative angle.

4. The skin information processing method according to claim 1, further comprising:

determining a positional correspondence, which is a correspondence between the base point of the ridge information for collation that is used in the skin authentication and the base point of the ridge information for registration that is stored in the storage portion; and calculating, on the basis of the positional correspondence determined in the correspondence determining, an information similarity degree, the information similarity degree being a similarity degree between the ridge information and the frequency information for collation and the ridge information and the frequency information for registration.

5. A skin information processing device, comprising:

a processor;

a storage portion; and a memory configured to store computer-readable instructions that, when executed by the processor, instruct the processor to perform processes comprising:

acquiring an image;

determining a base point that represents a sweat pore on a ridge of skin, from the acquired image and acquiring position information corresponding to a position of the base point on the image;

acquiring sample information indicating changes in color information around the determined base point;

generating, as frequency information, information associating frequency components of the acquired sample information with the position information; and causing the storage portion to store information including the generated frequency information and the position information of the base point, as information used in skin authentication.

6. The skin information processing device according to claim 5, wherein the computer-readable instructions further instruct the processor to perform processes comprising:

extracting, from among a plurality of the base points, a plurality of the base points disposed on a same continuous ridge; and generating ridge information including the position information of each of the plurality of extracting base points, and an arrangement order of the plurality of extracted base points on the ridge, and the causing the storage portion to store information includes causing the storage portion to store the generated ridge information and the frequency information, in association with each other, as the information used in the skin authentication.

7. The skin information processing device according to claim 6, wherein the computer-readable instructions further instruct the processor to perform a process comprising:

calculating, for each of the plurality of extracted base points, a relative angle of a line segment connecting the base point and a following base point in the arrangement order with respect to a line segment connecting the base point and a preceding base point in the arrangement order, the acquiring the sample information includes acquiring, as the sample information, information associating color information corresponding to a reference point with reference position information corresponding to a position of the reference point on the image, for each of a plurality of the reference points, the plurality of reference points being on a circumference of a circle whose center is the determined base point and whose radius is a predetermined value, and the plurality of reference points being acquired sequentially in accordance with a predetermined condition from a starting point determined on the basis of the base point and the calculated relative angle, the generating the frequency information includes calculating frequency components of changes in the color information with respect to the reference position information for the acquired sample information, using a linear prediction coefficient calculated without multiplying a window function, and generating the frequency information, and the generating the ridge information includes generating the position information of each of the plurality of extracted base points, the arrangement order of the extracted plurality of base points on the ridge, and the relative angle.

8. The skin information processing device according to claim 5, wherein the computer-readable instructions further instruct the processor to perform processes comprising:

determining a positional correspondence, which is a correspondence between the base point of the ridge information for collation that is used in the skin authentication and the base point of the ridge information for registration that is stored in the storage portion; and calculating, on the basis of the positional correspondence determined in the correspondence determining, an information similarity degree, the information similarity degree being a similarity degree between the ridge information and the frequency information for collation and the ridge information and the frequency information for registration.

9. A non-transitory computer-readable medium storing computer-readable instructions that are executed by a processor provided in a skin information processing device comprising a storage portion, the computer-readable instructions, when executed, instructing the processor to perform processes comprising:

acquiring an image;

determining a base point representing a sweat pore on a ridge of skin, from the acquired image and acquiring position information corresponding to a position of the base point on the image;

acquiring sample information indicating changes in color information around the determined base point;

generating, as frequency information, information associating frequency components of the acquired sample information with the position information; and causing the storage portion to store information including the generated frequency information and the position information of the base point, as information used in skin authentication.

10. The non-transitory computer-readable medium according to claim 9, wherein the computer-readable instructions further instruct the processor to perform processes comprising:

extracting, from among a plurality of the base points, a plurality of the base points disposed on a same continuous ridge; and generating ridge information including the position information of each of the plurality of extracted base points, and an arrangement order of the plurality of extracted base points on the ridge, and the causing the storage portion to store information includes causing the storage portion to store the generated ridge information and the frequency information, in association with each other, as the information used in the skin authentication.

11. The non-transitory computer-readable medium according to claim 10, wherein the computer-readable instructions further instruct the processor to perform a process comprising:

calculating, for each of the plurality of extracted base points, a relative angle of a line segment connecting the base point and a following base point in the arrangement order with respect to a line segment connecting the base point and a preceding base point in the arrangement order, the acquiring the sample information includes acquiring, as the sample information, information associating color information corresponding to a reference point with reference position information corresponding to a position of the reference point on the image, for each of a plurality of the reference points, the plurality of reference points being on a circumference of a circle whose center is the determined base point and whose radius is a predetermined value, and the plurality of reference points being acquired sequentially in accordance with a predetermined condition from a starting point determined on the basis of the base point and the calculated relative angle, the generating the frequency information includes calculating frequency components of changes in the color information with respect to the reference position information for the acquired sample information, using a linear prediction coefficient calculated without multiplying a window function, and generating the frequency information, and the generating the ridge information includes generating the position information of each of the plurality of extracted base points, the arrangement order of the extracted plurality of base points on the ridge, and the relative angle.

12. The non-transitory computer-readable medium according to claim 9, wherein the computer-readable instructions further instruct the processor to perform processes comprising:

determining a positional correspondence, which is a correspondence between the base point of the ridge information for collation that is used in the skin authentication and the base point of the ridge information for registration that is stored in the storage portion; and calculating, on the basis of the positional correspondence determined in the correspondence determining, an information similarity degree, the information similarity degree being a similarity degree between the ridge information and the frequency information for collation and the ridge information and the frequency information for registration.

* * * * *